US007906628B2

(12) United States Patent
Hung et al.

(10) Patent No.: US 7,906,628 B2
(45) Date of Patent: Mar. 15, 2011

(54) TARGETING PROTEINS TO DELIVER THERAPEUTIC OR DIAGNOSTIC REAGENTS

(75) Inventors: Mien-Chie Hung, Houston, TX (US);
Keng-Li Lan, Houston, TX (US);
Keng-Hsin Lan, Taipei (TW);
Jaw-Ching Liu, Houston, TX (US); Fu Ou Yang, Taipei (TW)

(73) Assignee: The Board of Regents, The University of Texas System, Austin, TX (US)

( * ) Notice: Subject to any disclaimer, the term of this patent is extended or adjusted under 35 U.S.C. 154(b) by 731 days.

(21) Appl. No.: 11/672,799

(22) Filed: Feb. 8, 2007

(65) Prior Publication Data

US 2007/0134206 A1 Jun. 14, 2007

Related U.S. Application Data

(63) Continuation of application No. 10/430,503, filed on May 6, 2003.

(60) Provisional application No. 60/380,063, filed on May 6, 2002.

(51) Int. Cl.
*C07K 19/00* (2006.01)
(52) U.S. Cl. ........................... 530/402; 530/350
(58) Field of Classification Search ............... 530/402, 530/350
See application file for complete search history.

(56) References Cited

U.S. PATENT DOCUMENTS

| 5,994,104 | A | 11/1999 | Anderson et al. |
| 6,413,513 | B1 | 7/2002 | Holaday et al. |
| 6,537,554 | B1 | 3/2003 | Shimkets et al. |
| 6,552,005 | B1 | 4/2003 | Buchsbaum et al. |
| 2002/0090374 | A1 | 7/2002 | Yarkoni et al. |

FOREIGN PATENT DOCUMENTS

| WO | WO-99/16889 A1 | 4/1999 |
| WO | WO-9930741 A2 | 6/1999 |
| WO | WO-99/39741 A2 | 8/1999 |
| WO | WO-9947690 A2 | 9/1999 |
| WO | WO-9965515 A2 | 12/1999 |
| WO | WO-0011033 | 3/2000 |
| WO | WO-0071078 A2 | 11/2000 |
| WO | WO-0074629 A2 | 12/2000 |
| WO | WO-0105826 | 1/2001 |
| WO | WO-0151523 | 7/2001 |
| WO | WO-01/87348 A2 | 11/2001 |
| WO | WO-0244328 | 6/2002 |

OTHER PUBLICATIONS

Helfrich et al. (2000) J. Immun. Methods, vol. 237, pp. 131-145.*
Azar et al. (2000) Apoptosis, vol. 5, 531-542.*
Verma et al. (2001) J. Biol. Chem, vol. 276 (7), 4671-4676.*
Chen et al. (1999) Cancer Research, vol. 59, pp. 3308-3312.*
Scappaticci et al. (2001) Angiogenesis, vol. 4, 263-268.*
Gyorffy et al.. (2001) J. Immunology, vol. 166, 6212-6217.*
Bowie et al (1990) Science, vol. 247, 1306-1310.*
Niethammer, Andreas G., et al.; Targeted Interleukin 2 Therapy Enhances Protective Immunity Induced by an Autologous Oral DNA Vaccine against Murine Melanoma; Cancer Research 61:6178-6184, Aug. 15, 2001.
Dreier, Torsten, et al.; Recombinant Immunocytokines Targeting the Mouse Transferrin Receptor: Construction and Biological Activities; Bioconjugate Chem. 9:482-489, 1998.
Ruehlmann, J. Michael, et al.; MIG (CXCL9) Chemokine Gene Therapy Combines with Antibody-Cytokine Fusion Protein to Suppress Growth and Dissemination of Murine Colon Carcinoma; Cancer Research 61:8498-8503, Dec. 1, 2001.
Lode, Holger N., et al.; Synergy between an antiangiogenic integrin av antagonist and an antibody—cytokine fusion protein eradicates spontaneous tumor metastases; Proc. Natl. Acad. Sci. USA (Medical Sciences) 96:1591-1596, Feb. 1999.
Penichet, Manuel L., et al.; Antibody—cytokine fusion proteins for the therapy of cancer; Journal of Immunological Methods 248:91-101, 2001.
Kreitman, Robert J.; Immunotoxins in cancer therapy; Current Opinion in Immunology 11:590-578,1999.
Holz, Hubert G., et al.; Specific Targeting of Tumor Vasculature by Diphtheria Toxin-Vascular Endothelial Growth Factor Fusion Protein Reduces Angiogenesis and Growth of Pancreatic Cancer; J. Gastrointest Surg 6:159-166, 2002.
Veenendaal, Liesbeth M., et al.; In vitro and in vivo studies of a VEGF121/rGelonin chimeric fusion toxin targeting the neovasculature of solid tumors; PNAS 99(12):7866-7871, Jun. 11, 2002.
Scappaticci, Frank A., et al.; Statin-AE: A n ovel angiostatin-endostatin fusion protein with enhanced antiangiogenic and antitumor activity; Angiogenesis 4:263-268, 2001.
Camemolla, Barbara, et al.; Enhancement of the antitumor properties of interleukin-2 by its targeted delivery to the tumor blood vessel extracellular matrix; Blood 99:1659-1665, 2002.
Halin, C., et al.; Enhancement of the antitumor activity of interleukin-12 by targeted delivery to neovasculature; Nature Biotechnology 20:264-269, Mar. 2002.
Kirsch, Matthias, et al.; Angiogenesis, metastasis, and endogenous inhibition; Journal of Neuro-Oncology 50:173-180, 2000.
Cao, Yihai; Endogenous angiogenesis inhibitors and their therapeutic implications; The International Journal of Biochemistry & Cell Biology 33:357-369, 2001.
Herbst, Roy S., et al.; Phase I Study of Recombinant Human Endostatin in Patients With Advanced Solid Tumors; J Clin Oncol 20(18):1-12, Sep. 15, 2002.
Eder, Jr., Joseph P., et al.; Phase I Clinical Trial of Recombinant Human Endostatin Administered as a Short Intravenous Infusion Repeated Daily; J Clin Oncol 20(18):1-13, Sep. 15, 2002.
Thomas, James P., et al.; Phase I Pharmacokinetic and Pharmacodynamic Study of Recombinant Human Endostatin in Patients with Advanced Solid Tumors; J Clin Oncol 21(2):223-231, Jan. 15, 2003.

(Continued)

*Primary Examiner* — Anne Marie S Wehbe
(74) *Attorney, Agent, or Firm* — Fulbright & Jaworski L.L.P.

(57) ABSTRACT

The present invention is directed to compositions comprising an angiogenesis inhibitor coupled to a therapeutic or diagnostic agent. In a specific embodiment, the composition is a fusion gene or fusion gene product encoding the angiogenesis inhibitor coupled to a therapeutic or diagnostic agent. In a particular embodiment, the composition is used for methods to treat angiogenesis-related diseases, such as cancer.

4 Claims, 8 Drawing Sheets

OTHER PUBLICATIONS

Tarabolette, Giulia, et al.; Antiangiogenic and antivascular therapy for cancer; Current Opinion in Pharmacology 1:378-384, 2001.

Boehm, Thomas, et al.; Antiangiogenic therapy of experimental cancer does not induce acquired drug resistance; Nature 390:404-407, Nov. 1997.

Burke, Patricia A., et al.; Antiangiogenic agents and their promising potential in combined therapy; Critical Reviews in Oncology/Hematology 39:155-171, 2001.

Kerbel, Robert S.; Clinical Trials of Antiangiogenic Drugs: Opportunities, Problems, and Assessment of Initial Results; Journal of Clinical Oncology 19(18s):45s- 51s, Sep. 15 Supplement, 2001.

Turner, Richard; Gastric cancer gets the run-around; Nature Medicine 8(5):449, May 2002.

Brem, Steven; Angiogenesis and Cancer Control: From Concept to Therapeutic Trial; Cancer Control 6(5):436-458, 1999.

Huang, Xianming, et al.; Tumor Infarctin in Mice by Antibody-Directed Targeting of Tissue Factor to Tumor Vasculature; Science 275:547-550, Jan. 24, 1997.

Molema, Grietje, et al.; The use of bispecific antibodies in tumor cell and tumor vasculature directed immunotherapy; Journal of Controlled Release 64:229-239, 2000.

Lode, Holger N., et al.; Synergy between an antiangiogenic integrin av antagonist and an antibody-cytokine fusion protein eradicates spontaneous tumor metastases; Proc. Nati, Acad. Sci. USA (Medical Sciences) 96:1591-1596, Feb. 1999.

Arora, Naveen, et al.; Vascular Endothelial Growth Factor Chimeric Toxin is Highly Active against Endothelial Cells; Cancer Research 59:183-188, Jan. 1, 1999.

Yang, David J., et al.; Assessment of Antiangiogenic Effect Using 99mTc-EC-Endostatin; Cancer Biotherapy & Radiopharmaceuticals 17(2):233-248, 2002 (date of mailing was May 9, 2002).

Yukihiro, Masashi, et al.; Assessment of angiogenesis using 99mTc-labeled endostatin and angiestatin; Abstract No. 4456, American Association for Cancer Research 2002 Meeting, San Francisco, CA; Abstract available online early Mar. 2002.

Aqueilan, R. S., et al.; Interleukin 2-Bax: A novel prototype of human chimeric proteins for targeted therapy. FEBS Lett, (1999) vol. 457, No. 2, pp. 271-276.

Azar, Y., et al.; GnRH-Bik/Bax/Bak chimeric proteins target and kill adenocarcinoma cells; the general use of pro-apoptotic proteins of the Bcl-2 family as novel killing components of targeting chimeric proteins. Apoptosis (2000) vol. 5, No. 6, pp. 531-542.

Gillies, S.D., et al.; Antibody-IL-12 fusion proteins are effective in SCID mouse models of prostate and colon carcinoma metastases. J. Immunol. (1998), vol. 160, No. 12, pp. 6195-6203.

Lode, H. N., et al. Immunocytokines: a promising approach to cancer immunotherapy. Pharmacol Ther. (1998), vol. 80, No. 3, pp. 277-292.

Henschke et al., "CT screening for lung cancer: update 2005", Surg Oncol Clin N Am., 2005; 761-76, vol. 14(4).

Johnson-Saliba et al., "Gene therapy: optimising DNA delivery to the nucleus", Curr Drug Targets, Dec. 2001; 371-99; vol. 2(4).

Niculescu-Duvaz et al., "Recent developments in gene-directed enzyme prodrug therapy (GDEPT) for cancer", Curr Opin Mol Ther, 1999, 480-6, vol. 1.

Pfeifer et al., "Gene therapy: promises and problems", Annu Rev Genomics Hum Genet. 2001; 177-211, vol. 2.

Sauter et al., "Adenovirus-mediated gene transfer of endostatin in vivo results in high level of transgene expression and inhibition of tumor growth and metastases", Apr. 25, 2000, 4802-4807, vol. 97(9).

Shoji et al., "Current Status of Delivery Systems to Improve Target Efficacy of Oligonucleotides", Curr Pharm Des, 2004, pp. 785-796, vol. 10.

Bowie et al., "Deciphering the message in protein sequences: tolerance to amino acid substitutions." Science. Mar. 16, 1990;247(4948):1306-10.

Chen et al., "Liposomes complexed to plasmids encoding angiostatin and endostatin inhibit breast cancer in nude mice," Cancer Res. Jul. 15, 1999;59(14):3308-12.

Claesson-Welsh et al., "Angiostatin induces endothelial cell apoptosis and activation of focal adhesion kinase independently of the integrin-binding motif RGD," Proc Natl Acad Sci U S A. May 12, 1998;95(10):5579-83.

Communication pursuant to Article 96(2) EPC re European Application No. 03733952.0-2404, issued Sep. 27, 2007.

Dickson et al., "Angiogenesis in acute and chronic leukemias," Leuk Lymphoma. Sep.-Oct. 2001;42(5):847-53.

EP Communication Pursuant to Article 94(3) EPC issued Oct. 9, 2008, during the prosecution of EA Application No. 03 733 952.0-2404.

Guhaniyogi et al., "Regulation of mRNA stability in mammalian cells." Gene. Mar. 7, 2001;265(1-2):11-23.

Gyorffy et al., Combined treatment of a murine breast cancer model with type 5 adenovirus vectors expressing murine angiostatin and IL-12: a role for combined anti-angiogenesis and immunotherapy, J Immunol. May 15, 2001;166(10):6212-7.

Helfrich et al., "A rapid and versatile method for harnessing scFv antibody fragments with various biological effector functions, " J Immunol Methods. Apr. 3, 2000;237(1-2):131-45.

Henschke, "CT screening for lung cancer: update 2005," Surg Oncol Clin N Am. Oct. 2005;14(4):761-76. Review.

Johnson-Saliba et al., "Gene therapy: optimising DNA delivery to the nucleus," Curr Drug Targets. Dec. 2001;2(4):371-99.

Kuo et al., "Comparative evaluation of the antitumor activity of antiangiogenic proteins delivered by gene transfer," Proc Natl Acad Sci U S A. Apr. 10, 2001;98(8):4605-10. Epub Mar. 27, 2001.

Marshall, "Gene therapy's growing pains," Science. Aug. 25, 1995;269(5227):1050-1055.

Ninck et al, "Expression profiles of angiogenic growth factors in squamous cell carcinomas of the head and neck," Int J Cancer. Aug. 10, 2003;106(1):34-44.

Orkin et al., "Report and recommendations of the panel to assess the NIH investment research on gene therapy," Dec. 7, 1995. National Institute of Health. Accessed on internet Dec. 3, 2008: http://www.nih.gov/news/panelrep.html.

Pfeifer et al., "Gene therapy: promises and problems," Annu Rev Genomics Hum Genet. 2001;2:177-211. Review.

Shoji et al., "Current status of delivery systems to improve target efficacy of oligonucleotides," Curr Pharm Des. 2004;10(7):785-96. Review.

Strieter et al., "CXC chemokines in angiogenesis related to pulmonary fibrosis," Chest. Dec. 2002;122(6 Suppl):298S-301S.

Supplementary European Search Report re European Application No. 03733592, issued Apr. 26, 2007.

Verma et al., "Gene therapy—promises, problems and prospects," Nature. Sep. 18, 1997;389(6648):239-42.

Communication of the Patent Office of the State Intellectual Property Office of the People's Republic of China issued Sep. 19, 2008, during the prosecution of Japanese Application No. 03816004.8.

Notice for Reasons for Rejection (Translation) issued Jun. 8, 2009 during the prosecution of Japanese Application No. 2004-501442.

Ou-Yang et al., "Endostatin-cytosine deaminase fusion protein suppresses tumor growth by targeting neovascular endothelial cells"; Cancer research; 2006, vol. 66(1), pp. 378-384.

* cited by examiner

TARGETING PROTEINS TO DELIVER THERAPEUTIC OR DIAGNOSTIC REAGENTS

This application claims priority to U.S. Provisional Patent Application 60/383,063, filed May 6, 2002, which is incorporated by reference herein in its entirety.

FIELD OF THE INVENTION

The present invention is directed to the fields of cell biology, molecular biology, cancer biology, and medicine. More particularly, the present invention relates to compositions comprising an angiogenesis inhibitor coupled to a therapeutic or diagnostic agent, and the use of such compositions in therapeutics and cancer therapy.

BACKGROUND OF THE INVENTION

A growing body of evidence reveals that many diseases ranging from age-related macular degeneration, artherosclerosis, rheumatoid arthritis, to cancer are related to angiogenesis, the formation of new blood vessels (Folkman, 2001). Among these angiogenesis-dependent diseases, cancer is the most targeted disease (Brem, 1999; Ferrara and Alitalo, 1999; Keshet and Ben-Sasson, 1999; Carmeliet and Jain, 2000). There are tens of new therapeutic reagents under development based on the theory of antiangiogenesis. In the seminal publication by Folkman, the growth of tumors in both the primary and metastatic sites relies on angiogenesis to support both nutrients and oxygen to tumors (Folkman, 1971). In the following three decades, it has become increasingly convincing that angiogenesis plays a pivotal role in the malignant phenotype. New blood vessel formation has been demonstrated as a critical prognostic factor as well as a therapeutic target in many tumors.

The understanding that tumor growth and metastasis closely relate to the extent of angiogenesis has prompted research laboratories and pharmaceuticals to develop strategies to inhibit angiogenesis, thereby cutting off the blood supply to tumors (Brem, 1999; Ferrara and Alitalo, 1999; Keshet and Ben-Sasson, 1999; Kerbel, 2001; Risau, 1998; Klohs and Hamby, 1999; Rosen, 2000; Burke and DeNardo, 2001; Taraboletti and Margosio, 2001; Glaspy, 2002). Despite the promise of the scientific rationales and scores of experimental drugs being studied in clinical trials, researchers have yet to see significantly positive results from these studies, given the exciting anticancer effects that were demonstrated in the preclinical animal experiments.

Two of the most followed clinical studies involved two endogenous angiogenesis inhibitors, endostatin and angiostatin. These proteins have been shown to be cancer-angiogenesis specific and have no effects on normal blood vessel growth. They have been shown to inhibit cancer growth in animal studies without significant side effects and induction of drug resistance. (Boehm et al., 1997). However, the results from human cancer clinical trials did not match the stunning outcome from the preclinical test (Thomas et al., 2003; Herbst et al., 2002; Eder et al., 2002). Tumor responses in these trials are extremely rare. If there are tumor responses, the rate of the tumor regression is very slow. In some cases, it took more than one year for a patient to see a tumor regress more than 25%. So far, no rapid tumor shrinkage has been demonstrated in clinical trial using these angiogenesis inhibitors. Although tumor responses were not commonly demonstrated in these clinical studies, these endogenous angiogenesis inhibitors did show a very favorable safety profile.

As opposed to the tumor-specific angiogenesis seen in the animal model, tumor-specific blood vessels have been developed for a considerably longer period of time. Therefore, the blood vessels in human tumors are more mature than those in mice tumors. In some embodiments, it will require a longer time of angiogenesis inhibition for these endogenous inhibitors to block the blood flow to tumor to the extent that apoptosis of cancer cells are triggered. These angiogenesis inhibitors exert their function by inhibiting the growth of cancer cells instead of killing the cancer cells. The mechanism of their effect is so called "cytostatic" instead of "cytotoxic". As opposed to cytotoxic reagents such as chemotherapy drugs, these cytostatic angiogenesis inhibitors can not efficiently attack well-established tumor blood vessels often seen in late stage tumor. Thus, these reagents so far did not demonstrate dramatic anticancer effect in clinical trials where most of the patients enrolled are in late stage and exhausted most of the available treatments In contrast to the relatively non-toxic yet less potent anti-angiogenic proteins, described elsewhere herein, various potent therapeutic proteins or polypeptides, and the nucleic acids encoding them, have been used in attempts to treat cancers (not necessarily just kill cancer cells) or were suggested for such use. These include, for example, suicidal proteins, apoptosis-inducing proteins, cytokines, interleukines, TNF family proteins, and nucleic acids encoding them. Specific examples include: GM-CSF, Interferon Alpha, Interferon beta, Interferon gamma, Interleukin-1 Beta, Interleukin-2, Interleukin-4, Interleukin-5, Interleukin-6, Interleukin-8, Interleukin-10, Interleukin-12, Interleukin-13, Interleukin-14, Interleukin-16, Interleukin-18, Interleukin-23, Interleukin-24, Tumor Necrosis Factor SuperFamily member 14, Tumor Necrosis Factor SuperFamily member 13B, Tumor Necrosis Factor Alpha, Tumor Necrosis Factor SuperFamily member 12, Intercellular Adhesion Molecule-1, Lymphocyte Function-Associated antigen-3, Co-Stimulatory Molecule B7-1, Co-Stimulatory Molecule B7-2, FMS-related tyrosine kinase 3 ligand, CD40 Ligand, Surface antigen CD70, T-cell activation cell surface glycoprotein ligand, Co-Stimulatory Molecule OX-40 ligand, TNF-related activation-induced cytokine, Tumor Necrosis Factor SuperFamily member 11, TNF-related activation-induced cytokine, Tumor Necrosis Factor SuperFamily member 11, Cytosine deaminase, HSV Thymidine Kinase, Fas ligand, Caspase 3, TGF-α1, TGF-α2, TRAIL, Bax, Bak, Bik, Bok, Noxa, a Bcl-2 family protein, Granulysin (NKG5), Granzyme A, Granzyme B, and Perforin.

For example, IL2 and Interferon-α (Glaspy, 2002) have been used in the treatment for renal cell carcinoma and melanoma. However, significant systemic toxicity is usually seen in the cancer patients, thereby limiting the increase of dose and their clinical effects. IL12 has demonstrated potent and broad anticancer effects (Trinchieri, 2003). However, unacceptable side effects have manifested in some clinical trials (Leonard et al., 1997), which hamper its promise as an anticancer reagent.

To minimize the systemic side effects of cytokines, such as interleukin, as well as those therapeutic proteins listed in Table 1, many proteins have been used to target these otherwise considerably toxic therapeutic proteins to tumor-specific blood vessel. In addition, small molecules have been also utilized for tumor imaging while coupled to proteins specific for targeting tumor angiogenic blood vessels. Some of these approaches are summarized in Table 1.

TABLE 1

| Targeting Tool | Therapeutic/Diagnostic Agent | Comments |
|---|---|---|
| Endostatin (Yang et al., 2002) | 99mTc | Small molecule 99mTC was used as imaging molecule. The inventors used proteins as fused molecule, which could be utilized in gene therapy without having to purify proteins. |
| antibody fragment specific to ED-B domain of fibronectin (Halin et al, 2002) | IL-12 | The targeting antibody fragment is specific to one of angiogenesis markers, ED-B domain of fibronectin. However, it does not possess antiangiogenic activity. |
| antibody fragment specific to ED-B domain of fibronectin (Carnemolla et al., 2002) | IL-2 | Similar approach as (Halin et al., 2002) |
| angiostatin-endostatin (Scappaticci et al., 2001) | Angiostatin-Endostatin | Two antiangiogenic proteins were fused together and demonstrated better antiangiogenic effect than single molecule. The new fusion protein still cytostatic, but not cytotoxic. |
| VEGF (Veenendaal et al., 2002; Arora et al., 1999; Hotz et al., 2002) | Gelonin diphtheria (Veenendaal et al., 2002) Toxin (Arora et al., 1999; Hotz et al., 2002) | VEGF is specific to VEGF receptors, which are expressed abundantly in tumor vasculatures. It can trigger the angiogenic pathway. VEGF is not an antiangiogenic protein. |
| antibody B21-2 to target I-A$^d$, a marker of tumor specific blood vessel (Huang et al., 1997) | truncated form of tissue factor (tTF) | This approach again uses an antibody specific for tumor blood vessel as targeting tool without intrinsic antiangiogenic property. tTF induces thrombosis, thereby blocking blood flow. |

Additional targeting strategies have involved the preparation of immunotoxins (Kreitman, 1999) by coupling antibodies specific to markers of tumor (CD20 of B-cell lymphoma, Her-2/neu of breast cancers, EGFR of colon, head and neck etc.) or tumor-specific blood vessels (ED-B domain of fibronectin, integrin αvβ3, VEGF receptors, etc.) to therapeutic reagents, such as interleukins, cytokines, gelonin, diphtheria toxin, radio-isotopes, etc. However, most of the immunotoxin strategies have yet to enjoy clinical success, except very few have been approved, such as Zevalin™ (ibritumomab tiuxetan) (IDEC Pharmaceuticals; San Diego, Calif.) and Baxxar (Corixa; Seattle, Wash.).

WO 99/16889 describes fusion proteins having an angiostatin amino acid sequence linked to a second moiety having different or complementary activity. In particular embodiments, the second moiety is selected from endostatin, human type I interferon, thrombospondin, interferon-inducible protein 10 (IP-10) and platelet factor 4. In other particular embodiments, the fusion proteins are used for anti-tumor treatment.

In view of the above, there is a need for compositions and methods that overcome the problems in the art and allow for the treatment of angiogenesis-dependent diseases.

BRIEF SUMMARY OF THE INVENTION

The current invention overcomes the problems listed above and results in compounds and therapies that allow for the diagnosis and treatment of angiogenesis-dependent diseases.

In the context of the invention, angiogenesis inhibitors are coupled to therapeutic or diagnostic agents. In many embodiments, the angiogenesis inhibitors are anti-angiogenesis proteins or polypeptides. Given their affinities to new cancer blood vessels, but not to normal blood vessels, these protein and polypeptides can be used as targeting proteins to deliver therapeutic or diagnostic reagents to the vicinity of diseased cells and/or tissues.

Therapeutic proteins/reagents linked to angiogenesis inhibitors have significantly enhanced therapeutic effects, as compared with angiogenesis inhibitors or therapeutic proteins/reagents used alone. Using angiogenesis inhibitors as a delivery (home-in) protein or agent brings the therapeutic reagents to the vicinity of cancer cells and/or tissues, because the angiogenesis inhibitors associate with and/or bind with angiogenesis-specific disease-specific blood vessels. The therapeutic effects of these therapeutic agents are enhanced as a result of the increased local concentrations.

In addition, angiogenesis inhibitors may also be coupled to diagnostic reagents. For example, they may be coupled to green fluorescent proteins, luciferase, radioisotopes, or combinations thereof. These angiogenesis inhibitor-diagnostic reagent conjugates will facilitate diagnosis of patients.

In broad embodiments, the invention related to compositions comprising an angiogenesis inhibitor coupled to a therapeutic or diagnostic agent. Some preferred aspects of the invention related to fusion proteins comprising an antiangiogenesis polypeptide region linked to a therapeutic protein or polypeptide region or a diagnostic protein or polypeptide region and to nucleic acids encoding such fusion proteins. However, in other embodiments, an angiogenesis inhibitor can be chemically cross-linked to a therapeutic or diagnostic agent.

Those of ordinary skill will understand, in view of this specification that any antiangiogenesis protein currently know, or in the future discocere, that allows for the aims of the invention to be achieved, will be of use in the contents of the invention. Specific antiangiogenesis proteins or polypeptides employed in the context of the invention are discussed in greater detail in other portions of this specification. Some specific examples, which are presently preferred, include endostatin, tumstatin, angiostatin, and a soluble portion of VEGF Receptor 2.

Therapeutic agents useful in the context of the invention will be well understood by those of skill in the art in view of this specification. In some cases, the therapeutic agent is a therapeutic protein or polypeptide. However small molecules, chemotherapeutic drugs, toxins, radioactive compounds, and any other form of therapeutic agent that may be employed in the invention to achieve a therapeutic benefit are also within the scope of the invention.

As described in greater detail in other portions of this specification, exemplary therapeutic proteins and polypeptides of the invention include, but are in no way limited to, those of the classes of suicidal proteins, apoptosis-inducing proteins, cytokines, interleukins, and TNF family proteins. Exemplary diagnostic proteins or peptides, include for example, a green fluorescent protein and luciferase. The above are only examples of therapeutic proteins that might be fused with an antiangiogenic sequence. One skilled in the art would appreciate that other therapeutic and diagnostic proteins may be used.

In some preferred embodiments of the invention, the angiogenesis inhibitor is an antiangiogenesis polypeptide, such as described elsewhere in this specification. Some preferred embodiments involve endostatin, tumstatin, angiostatin, or a soluble VEGF Receptor 2, as the antiangiogenesis polypeptide. Some preferred therapeutic embodiments of the invention involve, as a therapeutic protein or polypeptide, an interleukin protein or polypeptide, such as, for example, an interleukin-12, a suicide protein, such as, for example, a cytosine deaminase, or an apoptosis-inducing protein, such as, for example, a native or mutant bik protein. Some preferred diagnostic embodiments of the invention involve, as a diagnostic protein or polypeptide, a green flourescent protein or luciferase. Some specifically preferred therapeutic embodiments include: endostatin/interleukin-12, angiostatin/interleukin-12, tumstatin/interleukin-12, soluble VEGF Receptor 2/interleukin-12, endostatin/cytosine deaminase, angiostatin/cytosine deaminase, tumstatin/cytosine deaminase, soluble VEGF Receptor 2/cytosine deaminase, endostatin/mutant bik, angiostatin/mutant bik, tumstatin/mutant bik, and soluble VEGF Receptor 2/mutant bik. While some specifically preferred diagnostic embodiments include: endostatin/green flourescent protein, angiostatin/green flourescent protein, tumstatin/green flourescent protein, soluble VEGF Receptor 2/green flourescent protein, endostatin/luciferase, angiostatin/luciferase, tumstatin/luciferase, and soluble VEGF Receptor 2/luciferase.

While the simplest embodiments of the invention relate to one angiogenesis inhibitor coupled to one therapeutic or diagnostic agent, there is no reason why more elaborated compositions may not be constructed according to the invention. For example, it is possible to couple two or more angiogenesis inhibitors to a single therapeutic or diagnostic agent, a single angiogenesis inhibitor to two or more therapeutic or diagnostic agents; or even two or more angiogenesis inhibitors to two or more therapeutic or diagnostic agents. In some cases, multiple angiogenesis inhibitors, therapeutic agents, and/or diagnostic agents coupled in the context of the invention will be the same, for example two endostatin polypeptides coupled to a single interleukin-12 polypeptide. Alternatively, multiple angiogenesis inhibitors, therapeutic agents, and/or diagnostic agents coupled in the context of the invention will be the same, for example one endostatin polypeptide coupled to an interleukin-12 polypeptide and a cytosine deaminase polypeptide. Those of skill will be able to follow the teachings of the specification to make any such embodiments of the invention.

In embodiments of the invention relating to fusion proteins, those skilled in the art would appreciate that, typically, the fusion proteins will be expressed from a nucleic acid sequence encoding an antiangiogenesis polypeptide region linked to a therapeutic protein or polypeptide region or a diagnostic protein or polypeptide region. In such nucleic acids, it is possible that the nucleic acid sequence encoding an antiangiogenesis polypeptide region could be placed at either the 5' or the 3' end of the nucleic acid sequence encoding the therapeutic protein or polypeptide region or a diagnostic protein or polypeptide region. Furthermore, the invention is not restricted in regard to how nucleic acids encoding these fusion proteins should be constructed into an expression vector. The antiangiogenic nucleic acid and the therapeutic or diagnostic nucleic acid may be constructed into a vector in separate construction steps. Alternatively, they may be first fused, then constructed into an expression vector. The invention also relates to nucleic acids encoding a fusion protein comprising an antiangiogenesis polypeptide region linked to a therapeutic protein or polypeptide region or a diagnostic protein or polypeptide region. Such nucleic acids may be comprised in a vector, complexed with a lipid, and/or comprised in a pharmaceutically acceptable excipient.

Some specific embodiments of the invention relating to methods of making fusion proteins and nucleic acids encoding such fusion proteins comprise: obtaining a first nucleic acid encoding a fusion protein comprising an antiangiogenesis polypeptide region or complement thereof; obtaining a second nucleic acid encoding a therapeutic protein or polypeptide region or a diagnostic protein or polypeptide region or complement thereof; and using the first nucleic acid and the second nucleic acid to create a nucleic acid encoding a fusion protein comprising an antiangiogenesis polypeptide region linked to a therapeutic protein or polypeptide region or a diagnostic protein or polypeptide region. These methods may further comprise testing the nucleic acid encoding the fusion protein for an ability to, under appropriate conditions, express the fusion protein and/or for diagnostic or therapeutic activity. Such methods may also, further comprise administering the nucleic acid encoding the fusion protein to a subject.

In addition to using a fusion protein approach, the therapeutic or diagnostic proteins or small molecule reagents may be cross-linked to an antiangiogenic protein, polypeptide, or peptide using chemical cross-linking reagents. One skilled in the art would know that various cross-linking reagents that are specific for certain amino acid side chains are available from commercial sources. The choice of a particular cross-linking reagent would depend on the proteins (or small molecule therapeutic or diagnostic agents) involved.

With a chemical cross-linking approach, one could practice a method comprising: obtaining an angiogenesis inhibitor; obtaining a therapeutic or diagnostic agent; chemically cross-linking the angiogenesis inhibitor to the therapeutic or diagnostic agent to create an angiogenesis inhibitor coupled to the therapeutic or diagnostic agent. Such a method might further comprise testing the angiogenesis inhibitor coupled to the therapeutic or diagnostic agent for diagnostic or therapeutic activity and/or administering the angiogenesis inhibitor coupled to the therapeutic or diagnostic agent to a subject. In an exemplary embodiment, one could express the antiangiogenic gene product, cross link it with the desired molecule (therapeutic or diagnostic), purify the cross-linked product, and administer the product to patients (such as, for example, for therapeutic purposes or a diagnostic purpose, or both) or to laboratory animals (for research purpose).

Some aspects of the invention relate to methods comprising treating a cell with a composition comprising an angiogenesis inhibitor coupled to a therapeutic or diagnostic agent. The cell may be comprised in a subject, or in the alternative, in cell culture. In some embodiments, the cell is comprised in a test subject, such as a mouse. In other embodiments, the subject is a human.

Preferred aspects of the invention related to methods of treating or diagnosing an angiogenesis-dependent disease, for example, but not limited to cancer, age-related macular degeneration, artherosclerosis, angiofibroma, neovascular glaucoma, arteriovenous malformations, nonunion fractures, arthritis, rheumatoid arthritis, lupus, connective tissue, disorders, Osler-Weber syndrome, psoriasis, corneal graft neovascularization, pyogenic granuloma, delayed wound healing, retrolental fibroplasia, diabetic retinopathy, scleroderma, granulations, hemangioma, trachoma, hemophilia joints, vascular adhesions, hypertrophic scars, multiple sclerosis, restenosis, and obesity. Those of skill in the art will, in the context of the invention, understand the definition of "angiogenesis-dependent disease." Some particular embodiments relate to the treatment of cancer, for example, but not limited to the cancer is head and neck cancer, ovarian cancer, thyroid cancer, oral cancer, prostate cancer, melanoma, colon cancer, breast cancer, angioma, sarcoma, lung cancer, brain cancer, pancreatic cancer, liver cancer, bladder cancer, gastrointestinal cancer, leukemia, lymphoma, and myeloma. Some embodiments of these methods comprise administering to a subject an angiogenesis inhibitor coupled to a therapeutic or diagnostic agent, for example, but not limited to, a fusion protein, comprised in pharmacologically acceptable excipient. Other embodiments, comprise administering to the subject a nucleic acid encoding a fusion protein comprising an antiangiogenesis polypeptide region linked to a therapeutic protein or polypeptide region or a diagnostic protein or polypeptide region. In such cases, nucleic acid may comprised in a plasmid, a retroviral vector, an adenoviral vector, an adeno-associated viral vector, or associated with a lipid. Further, the nucleic acid may be dispersed in a pharmacologically acceptable excipient.

Specific aspects of the invention relate to methods of treating or diagnosing cancer comprising: obtaining a fusion protein comprising an antiangiogenesis polypeptide region linked to a therapeutic protein or polypeptide region or a diagnostic protein or polypeptide region or a nucleic acid encoding a fusion protein comprising an antiangiogenesis polypeptide region linked to a therapeutic protein or polypeptide region or a diagnostic protein or polypeptide region; and administering the fusion protein or nucleic acid encoding the fusion protein to a patient.

Other specific aspects of the invention relate to diagnostic and/or therapeutic kits that comprise a composition, fusion protein, or nucleic acid encoding a fusion protein of the invention in an appropriate container.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

FIG. 1A demonstrates anti-endostatin antibody Western blot of supernatants collected from 293 cells (18 KD endostatin(☐), 58 KD endostatin-CD (◄), and 93 KD endo-IL12(←)). In FIG. 1B, an ELISA kit (specific for endostatin) was utilized.

In FIGS. 2A through 2C, HUVEC cell tube formation was studied, and in FIGS. 2E through 2G, cell migration was studied. In FIGS. 2D and 2H, five fields were viewed; and the respective tubes or migrated cells were counted and averaged.

FIGS. 3A and 3B show an MTT assay. FIG. 3C shows green fluorescent protein expression in 293T cells transfected with Endo-GFP fusion gene. In FIG. 3D, the cell proliferation of NSF60 was studied for stimulation by conditional medium from COS-7 transfected by Endostatin-GM-CSF plasmid.

FIG. 5A provides GFP detection in an experimental group utilizing tumor of B-16 endostatin-GFP stable cell lines. FIG. 5B provides GFP detection in contra-lateral tumor to A (from B-16 parental cell lines) in blood vessel wall (◄). FIG. 5C shows GFP detection in tumors from bilateral B-16 parental cell lines in a control group.

FIG. 7A provides intratumoral gene therapy against B16F10 tumor. FIG. 7B shows similar intratumoral gene therapy as in FIG. 7A against B16F10 tumor, except original distant tumor was challenged at $2 \times 10^5$ cell. FIG. 7C provides illustration comparing endo-IL12 versus IL12 and endostatin alone.

FIG. 8A shows ex vivo treatment of endostatin-CD fusion gene of antiangio-chemotherapy (Endo: endostatin; CD: cytosine deaminase; Endo-CD: fusion gene). FIG. 8B shows that ex vivo treatment of Tum5-IL12 fusion gene of antiangio-immunotherapy showed better tumor inhibitory effect on distant tumor (Tum5: tumstatin antiangiogenic deletion mutant, IL12: interleukin-12, Tum5-IL12: fusion gene). FIG. 5C illustrates distant CT26 colon cancer growths in the presence of the fusion genes. Various genes were injected into CT26 tumor sites distant from the measured tumors, which were not treated with direct injection of genes.

DETAILED DESCRIPTION OF THE INVENTION

Definitions

Figure 1:
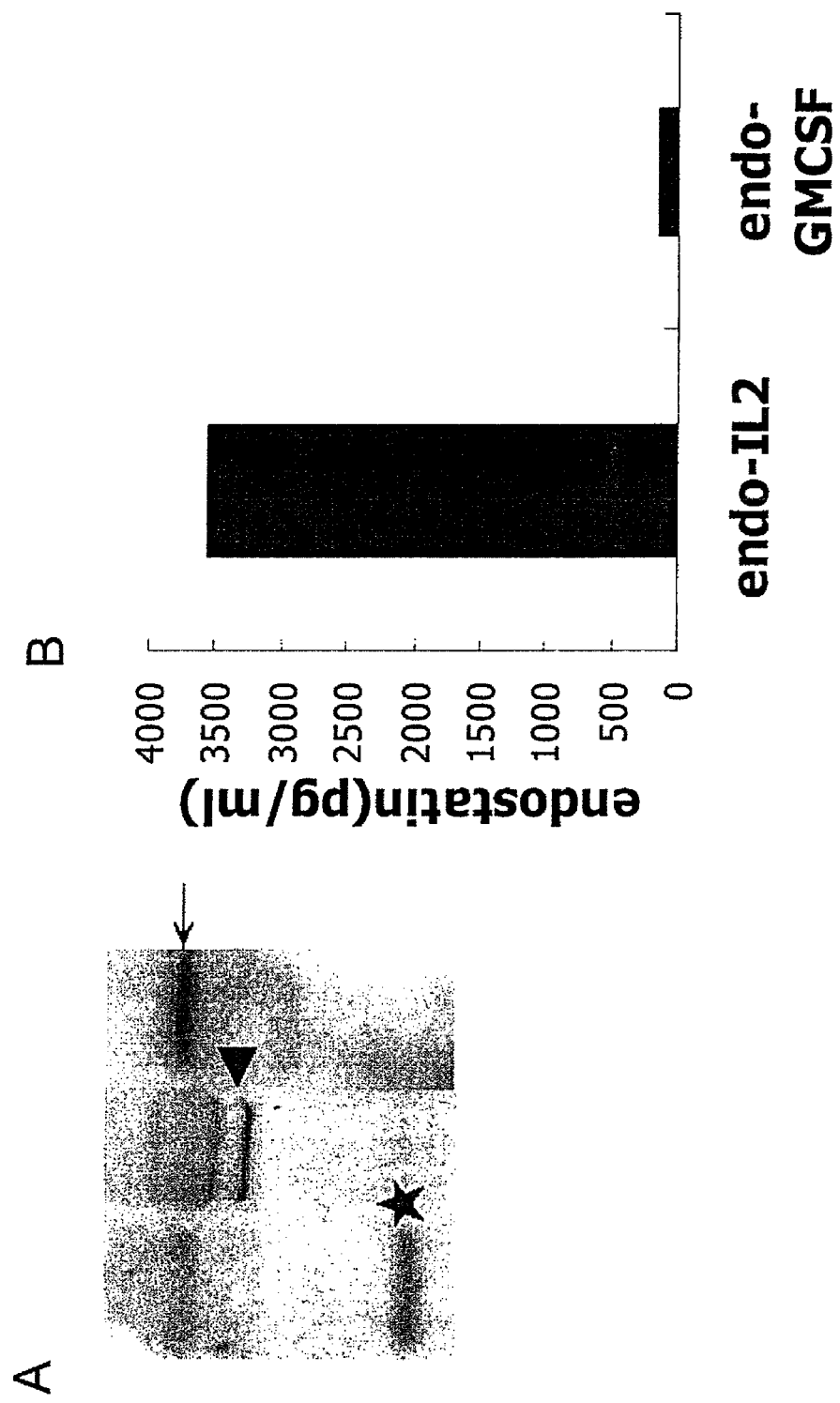
FIGS. 1A and 1B show that antiangiogenic-therapeutic/diagnostic fusion protein could be detected.

As used herein the specification, "a" or "an" may mean one or more. As used herein in the claim(s), when used in conjunction with the word "comprising", the words "a" or "an" may mean one or more than one. As used herein "another" may mean at least a second or more.

The term "therapeutically effective" as used herein refers to the amount of a compound required to improve some symptom associated with a disease. For example, in the treatment of cancer, a compound that improves the cancer to any degree or arrests any symptom of the cancer would be therapeutically effective. For example, the improvement of the cancer may be inhibition of angiogenesis of a cancer cell and/or tissue, inhibition or retardation of cell growth, facilitation of cell death, or a combination thereof. A therapeutically effective amount of a compound is not required to cure a disease but will provide a treatment for a disease.

This application incorporates by reference herein in its entirety PCT International Application WO 99/16889.

The Present Invention

To provide useful compositions and methods for use in the art of cancer therapy, the inventors exploit endogenous angiogenesis inhibitors, which are tumor vessel-specific. In exemplary embodiments, the inventors construct an angiogenesis inhibitor coupled to a therapeutic or diagnostic agent. In some exemplary embodiments, the angiogenesis inhibitor coupled to a therapeutic or diagnostic agent is a fusion of two components: the antiangiogenic component and the therapeutic (or diagnostic) component. In a specific embodiment, the angiogenesis inhibitor coupled to a therapeutic or diagnostic agent is a fusion gene that encodes a fusion protein comprising the two protein components. Thus, the fusion genes may be generated by connecting coding sequences of both antiangiogenic and therapeutic (or diagnostic) protein, thereby transforming cytostatic antiangiogenic proteins into cytotoxic fusion proteins. In addition, antiangiogenic protein could be also fused with diagnostic proteins, such as green fluorescent protein and luciferase, which could be led by antiangiogenic protein to tumor-specific blood vessels. In the alternative embodiment, the antiangiogenic protein component and the therapeutic or diagnostic protein component are chemically linked by standard means in the art. In exemplary embodiments, fusion gene constructs are generated by fusing the nucleic acid encoding at least one antiangiogenic protein with at least one therapeutic or diagnostic nucleic acid.

Given the affinities of angiogenesis inhibitors to newly formed cancer blood vessels, but not to normal blood vessels, these proteins are used as targeting proteins to deliver therapeutic reagents to the vicinity of cancer cells without expansion of toxicity. Therapeutic proteins/reagents linked to these angiogenesis inhibitor will have significantly enhanced cancer killing and anti-cancer effects as compared with angiogenesis inhibitor or the therapeutic proteins/reagents used alone.

Antiangiogenic Proteins

Any antioangiogenic protein, polypeptide, or peptide may be utilized for the angiogenesis inhibitor coupled to a therapeutic or diagnostic agent, such as the exemplary targeting fusion gene products of the present invention. Angiogenic inhibitors (also referred to as antiangiogenic compounds) are those that inhibit, reduce, halt, retard, impede, prevent, deter, slow down, reverse, or hinder angiogenesis. In a specific embodiment, the angiogenesis in a tissue imparts deleterious effects on the tissue in which the blood vessels are generating, such as to a tumor or a retina.

Exemplary embodiments include Angiopoietin-2, Angiostatin, AntiThrombin III (AT3), Amino-terminal fragment of Urokinase, Calreticulin, Endostatin, VEGF Receptor 2 (soluble fragment) (prepared by removal of a transmembrane region), VEGF Receptor 1 (soluble fragment) (prepared by removal of a transmembrane region), Interferon-alpha Inducible Protein 10, the 5 Kringle domains of plasminogen, Kringle-5 domain of plasminogen, Mammary serine protease inhibitor, Monokine-induced by Interferon-gamma, Angiostatic chemokines Fusion Gene, Pigment Epithelium-Derived Factor, C-term hemopexin domain of MMP-2, Platelet Factor 4 (CXCL4), Proliferin-Related Protein, Endothelium-specific receptor tyrosine kinase, Tissue inhibitor of metalloproteinase-1, Tissue inhibitor of metalloproteinase-2, Tissue inhibitor of metalloproteinase-3, Tissue inhibitor of metalloproteinase-4, Troponin I-2 (fast-twitch skeletal muscle), Ser94-Gln471 fragment of Tryptophanyl-tRNA synthetase, Thrombospondin, Tumstatin, or a combination thereof. A skilled artisan recognizes how to obtain the sequences for these proteins, polypeptides, or peptides, and the nucleic acid sequences that encode them, by accessing their publically available sequences in the GenBank database provided by the National Center for Biotechnology Information, using well-known means in the art. Exemplary embodiments of antiangiogenic sequences include (accompanied, where appropriate, with their GenBank sequence): endostatin (AF333247; SEQ ID NO:37); angiostatin (SEQ ID NO:38); tumstatin (AF258351; SEQ ID NO:39) and thrombospondin (M81339; SEQ ID NO:40).

Any of these antiangiogenic nucleic acids, as well as others in the art or identified at a later date and not listed herein, could be delivered as a component of gene therapy reagents against cancer or angiogenesis-dependent diseases as fusions with a therapeutic and/or diagnostic protein, as listed herein or as is well known in the art or that may be identified at a later date. Alternatively, fusion proteins encoded by these fusion nucleic acids, and those not listed herein, could be expressed and purified for protein therapy targeting cancer and other angiogenesis-dependent diseases.

A skilled artisan recognizes that, in some embodiments, an antiangiogenic sequence may provide therapy for the disease and/or may provide diagnostic capability for the disease.

Therapeutic/Diagnostic Proteins

Many compositions of the present invention comprise a therapeutic or diagnostic protein or polypeptide, or nucleic acids encoding therefore. Any such therapeutic or diagnostic protein or polypeptide, or nucleic acid encoding such may be used in the present invention, whether presently know to those of skill or discovered after the filing of this application.

One skilled in the art is aware of a variety of therapeutic proteins or polypeptides, and the nucleic acids encoding them that will be beneficial for the treatment of angiogenesis-dependent diseases, including cancer therapy. In specific embodiments, such therapeutic proteins or polypeptides may can include, but not be limited to, suicide proteins, toxin proteins, pro-apoptotic proteins, cytokine proteins, and/or anti-angiogenic proteins.

In specific methods and compositions of the present invention, the therapeutic polypeptide or protein is a "suicide protein" that causes cell death by itself or in the presence of other compounds. A representative example of such a suicide protein is thymidine kinase of the herpes simplex virus. Additional examples include thymidine kinase of varicella zoster virus, the bacterial gene cytosine deaminase (which converts 5-fluorocytosine to the highly toxic compound 5-fluorouracil), p450 oxidoreductase, carboxypeptidase G2, β-glucuronidase, penicillin-V-amidase, penicillin-G-amidase, β-lactamase, nitroreductase, carboxypeptidase A, linamarase (also referred to as β-glucosidase), the *E. coli* gpt gene, and the *E. coli* Deo gene, although others are known in the art. In some embodiments, the suicide protein converts a prodrug into a toxic compound. As used herein, "prodrug" means any compound useful in the methods of the present invention that can be converted to a toxic product, i.e. toxic to tumor cells. The prodrug is converted to a toxic product by the suicide protein. Representative examples of such prodrugs include: ganciclovir, acyclovir, and FIAU (1-(2-deoxy-2-fluoro-β-D-arabino-furanosyl)-5-iodouracil) for thymidine kinase; ifosfamide for oxidoreductase; 6-methoxypurine arabinoside for VZV-TK; 5-fluorocytosine for cytosine deaminase; doxorubicin for β-glucuronidase; CB1954 and nitrofurazone for nitroreductase; and N-(Cyanoacetyl)-L-phenylalanine or N-(3-chloropropionyl)-L-phenylalanine for carboxypeptidase A. The prodrug may be administered readily by a person having ordinary skill in this art. A person with ordinary skill would readily be able to determine the most appropriate dose and route for the administration of the prodrug. In specific embodiments, the prodrug is administered in a dose of from about 1-20 mg/day/kg body weight, from about 1-50 mg/day/kg body weight, or about 1-100 mg/day/kg body weight.

In some embodiments, a therapeutic protein or polypeptide, is a cancer suppressor, for example p53 or Rb, or a nucleic acid encoding such a protein or polypeptide. Of course, those of skill know of a wide variety of such cancer suppressors and how to obtain them and/or the nucleic acids encoding them.

Other examples of therapeutic proteins or polypeptides include pro-apoptotic therapeutic proteins and polypeptides, for example, p15, p16, or p21$^{WAF-1}$. One specific embodiment, involves pro-apototic proteins or polypeptides which are wild-type Bik or mutant Bik comprising similar or greater activity compared to wild-type Bik. In some specific embodiments further specific embodiment, the Bik mutant comprises a substitution at Thr$^{33}$, Ser$^{35}$, or both Thr$^{33}$ and Ser$^{35}$. In an additional specific embodiment, the substitution is with Asp. U.S. Provisional Patent Application No. 60/459,901, filed Apr. 2, 2003, which is incorporated by reference herein in its entirety, describes Bik, mutant Biks, and nucleic acid sequences encoding them.

Cytokines, and nucleic acid encoding them may also be used as therapeutic proteins and polypetided. Examples include: GM-CSF (granulocyte macrophage colony stimulating factor); TNFα (Tumor necrosis factor α); Interferons including, but not limited to, IFN α and IFN γ; and Interleukins including, but not limited to, Interleukin-1 (IL1), Interleukin-Beta (IL-beta), Interleukin-2 (IL2), Interleukin-4 (IL4), Interleukin-5 (IL5), Interleukin-6 (IL6), Interleukin-8 (IL8), Interleukin-10 (IL10), Interleukin-12 (IL12), Interleukin-13 (IL13), Interleukin-14 (IL14), Interleukin-15 (IL15), Interleukin-16 (IL16), Interleukin-18 (IL18), Interleukin-23 (IL23), Interleukin-24 (IL24), although other embodiments are known in the art.

An exemplary, but not limiting or comprehensive list of therapeutic proteins or polypeptides includes (followed in some cases by the a GenBank Accession No. for a nucleic acid encoding them): Herpes simplex virus type 1 (mutant KG111) thymidine kinase (SEQ ID NO:1; J04327); Herpes simplex virus type 2 (strain 9637) thymidine kinase (tk) (SEQ ID NO:2; M29941); Varicella zoster thymidine kinase (SEQ ID NO:3; M36160); *Escherichia coli* cytosine deaminase (SEQ ID NO:4; S56903); p450 oxidoreductase (SEQ ID NO:5; D17571); carboxypeptidase G2 (SEQ ID NO:6; M12599); β-glucuronidase (SEQ ID NO:7; M15182); penicillin-V-amidase (SEQ ID NO:8; M15660); penicillin-G-amidase (SEQ ID NO:9; AF161313); β-lactamase (SEQ ID NO:10; AY029068); nitroreductase (SEQ ID NO:11; A23284); carboxypeptidase A (SEQ ID NO:12; M27717); linamarase (SEQ ID NO:13; S35175); *E. coli* gpt (SEQ ID NO:14; X00221); *E. coli* Deo (SEQ ID NO:15; X03224); p53 (SEQ ID NO:16; AF307851); Rb (SEQ ID NO:17; XM_053409); p15 (SEQ ID NO:18; U19796); p16 [(SEQ ID NO:19; U12818) (SEQ ID NO:20; U12819) and (SEQ ID NO:21; U12820)]; p21$^{WAF-1}$ (SEQ ID NO:22; AF497972); GM-CSF (SEQ ID NO:23; M10663); TNF α (SEQ ID NO:24; AY066019); IFN α (SEQ ID NO:25; M34913); IFN α (SEQ ID NO:26; J00219); Interferon gamma; Interferon beta; IL1 (SEQ ID NO:27; M28983); IL-beta; IL2 (SEQ ID NO:28; K02056); IL3 (SEQ ID NO:29; M14743); IL4 (SEQ ID NO:30; M23442); IL5; IL6 (SEQ ID NO:31; M29150); IL7 (SEQ ID NO:32; J04156); IL8; IL10 (SEQ ID NO:33; U16720); IL12A (SEQ ID NO:34; NM_000882); IL12B (SEQ ID NO:35; NM_002187); IL13; IL14; IL15 (SEQ ID NO:36; U14407); IL16; IL18; IL23; IL24; Tumor Necrosis Factor SuperFamily member 14; Tumor Necrosis Factor SuperFamily member 13B (also called BlyS, BAFF, THANK); soluble form; Tumor Necrosis Factor Alpha; Tumor Necrosis Factor SuperFamily member 12 (also called Apo3L); Intercellular Adhesion Molecule-1; Lymphocyte Function-Associated antigen-3; Co-Stimulatory Molecule B7-1; Co-Stimulatory Molecule B7-2; FMS-related tyrosine kinase 3 ligand; CD40 Ligand; Surface antigen CD70; T-cell activation cell surface glycoprotein ligand; Co-Stimulatory Molecule OX-40 ligand (formerly gp34); TNF-related activation-induced cytokine; full-length (isoform 1, ODF; RANKL). Tumor Necrosis Factor SuperFamily member 11; TNF-related activation-induced cytokine; soluble form (isoform 2, sODF, sRANKL). Tumor Necrosis Factor SuperFamily member 11; Granulysin (NKG5); Granzyme A; Granzyme B; and Perforin.

Examples of diagnostic proteins include Green fluorescent protein (M62653; SEQ ID NO:41), Luciferase (SEQ ID NO:42), or a combination thereof.

In specific embodiments of the present invention, a nucleic acid segment encoding a therapeutic or diagnostic protein or polypeptide is comprised in a vector, such as a nonviral vector, a viral vector, or a combination thereof. The viral vector may be an adenoviral vector, a retroviral vector, or an adeno-associated viral vector. The nonviral vector may be a plasmid or a liposome. The nucleic acid segment may also be comprised in a pharmaceutical composition.

Any combinations of the therapeutic or diagnostic fusion nucleic acids could be delivered as gene therapy reagents to use against cancer or angiogenesis-dependent diseases as one component along with an antiangiogenic gene product listed herein or known in the art. Alternatively, fusion proteins encoded by these fusion genes could be expressed and purified for protein therapy targeting cancer and other angiogenesis dependent diseases.

A skilled artisan recognizes that a therapeutic sequence may also serve as a diagnostic sequence, and vice versa. In other embodiments, an angiogenesis inhibitor coupled to a diagnostic agent is used prior to angiogenesis inhibitor coupled to a therapeutic agent.

General Embodiments

The present invention regards targeting anti-angiogenic fusion polypeptides and/or the nucleic acids that encode them, as well as methods regarding the use of same. Thus, in exemplary embodiments, the present inventors demonstrate that endogenous angiogenesis inhibitors, such as endostatin, tumstatin, angiostatin, etc., could specifically target new blood vessel formation, which is a hallmark of angiogenesis-dependent diseases, including cancer. Although any cancer may be treated or prevented in accordance with the present invention, some examples include head and neck, ovarian, thyroid, oral, prostate, melanoma, colon cancer, breast cancer, angioma, sarcoma, lung cancer, brain cancer, pancreatic cancer, liver cancer, bladder cancer, gastrointestinal cancer, leukemia, lymphoma, and myeloma.

Specifically, these antiangiogenic proteins could be fused with therapeutic or diagnostic proteins and serve as a guiding tool to deliver the fusion protein to the vicinity of pathological angiogenic sites. These fusion proteins encoded by fusion gene constructs enhanced the therapeutic effects by combining functions of both antiangiogenic and therapeutic proteins. In addition, the targeting property contributed by antiangiogenic proteins could minimize the systemic toxic effect of therapeutic proteins by targeting the fusion proteins to the disease site(s).

In a specific embodiment, the present invention regards anti-angiogenic targeting fusion proteins to treat cancer in a mammal. For example, human ovarian cancer, pancreatic cancer, breast cancer, prostate cancer, and other cancers may be treated with compositions described herein or taught to a skilled artisan by analogous procedures described herein. In some embodiments, it is delivered by, for example, either a viral or non-viral delivery system into an appropriate recipient animal to inhibit angiogenesis, suppress tumor growth and development, or a combination thereof.

Exemplary anti-angiogenic targeting fusion proteins were generated. These fusions in preferred embodiments of the present invention, selectively inhibit angiogenesis, inhibit cell proliferation, inhibit cancer cell growth, or a combination thereof. One skilled in the art following the teachings of this specification can generate other exemplary anti-angiogenic targeting fusion proteins.

In some embodiments of the present invention, there are methods of preventing growth of a cell in an individual comprising administering to the individual an anti-angiogenic targeting fusion polypeptide. In specific embodiments, the polypeptide is administered in a liposome and/or the polypeptide further comprises a protein transduction domain (Schwarze et al., 1999). In some embodiments, an anti-angiogenic targeting fusion protein is administered as a polynucleotide, wherein the polynucleotide comprises an alteration that effects modification at the amino acid level, such as may be generated by site-directed mutagenesis. The modified anti-angiogenesis targeting fusion polynucleotide may be administered in a vector such as a plasmid, retroviral vector, adenoviral vector, adeno-associated viral vector, liposome, or a combination thereof.

There are also embodiments of the present invention wherein there are methods of treating a cell comprising contacting the cell with an anti-angiogenic targeting fusion polypeptide. In specific embodiments, the cell is a human cell, the cell is comprised in an animal, and/or the animal is human.

Targeting Fusion Production

While the chimeric proteins of the present invention may be produced by chemical synthetic methods or by chemical linkage between the two moieties, it is preferred that they are produced by fusion of a coding sequence of an antiangiogenic moiety and a coding sequence of a therapeutic or diagnostic moiety under the control of a regulatory sequence that directs the expression of the fusion polynucleotide in an appropriate host cell. In preferred embodiments, each of the components of the chimeric protein comprise functional activity for their respective parts being an antiangiogenic moiety and a therapeutic or diagnostic moiety.

The fusion of two full-length coding sequences can be achieved by methods well known in the art of molecular biology. It is preferred that a fusion polynucleotide contain only the AUG translation initiation codon at the 5' end of the first coding sequence without the initiation codon of the second coding sequence to avoid the production of two separate encoded products. In addition, a leader sequence may be placed at the 5' end of the polynucleotide in order to target the expressed product to a specific site or compartment within a host cell to facilitate secretion or subsequent purification after gene expression. The two coding sequences can be fused directly without any linker or by using a linker. In a specific embodiment, a linker for connecting the antiangiogenic and therapeutic/diagnostic proteins comprises either VPGVG (elastin Val-Pro-Gly-Val-Gly) or Gly-Gly-Gly-Ser-Gly. Other linkers are known to those of skill in the art, such as are described in WO 99/16889, which is incorporated by reference herein in its entirety.

In accordance with the objects of the present invention, a polynucleotide that encodes a fusion protein may be used to generate recombinant DNA molecules that direct the expression of the fusion protein, fusion peptide fragments, or a functional equivalent thereof, in appropriate cells. Due to the inherent degeneracy of the genetic code, other DNA sequences that encode substantially the same or a functionally equivalent amino acid sequence, may be used in the practice of the invention of the cloning and expression of the fusion protein. Such DNA sequences include those capable of hybridizing to the fusion sequences or their complementary sequences under stringent conditions, which are well known to a skilled artisan.

Altered DNA sequences that may be used in accordance with the invention include deletions, additions or substitutions of different nucleotide residues resulting in a sequence that encodes the same or a functionally equivalent fusion gene product. The gene product itself may contain deletions, additions or substitutions of amino acid residues within a fusion sequence, which result in a silent change thus producing a functionally equivalent fusion protein. Such amino acid substitutions may be made on the basis of similarity in polarity, charge, solubility, hydrophobicity, hydrophilicity, and/or the amphipathic nature of the residues involved, which is well known to a skilled artisan.

The DNA sequences of the invention may be engineered in order to alter a fusion coding sequence for a variety of ends, including but not limited to, alterations that modify processing and expression of the gene product, as described elsewhere in greater detail. For example, mutations may be introduced using techniques which are well known in the art, e.g., site-directed mutagenesis, to insert new restriction sites, to alter glycosylation patterns, phosphorylation, etc.

In one embodiment of the invention, the coding sequence of the fusion protein could be synthesized in whole or in part, using chemical methods well known in the art. (See, for example, Caruthers et al., 1980; Crea and Horn, 1980; and Chow and Kempe, 1981). For example, active domains of the moieties can be synthesized by solid phase techniques, cleaved from the resin, and purified by preparative high performance liquid chromatography followed by chemical linkage to form a chimeric protein. (e.g., see Creighton, 1983, Proteins Structures And Molecular Principles, W.H. Freeman and Co., N.Y. pp. 50-60). The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y. pp. 34-49). Alternatively, the two moieties of the fusion protein produced by synthetic or recombinant methods may be conjugated by chemical linkers according to methods well known in the art (Brinkmann and Pastan, 1994).

In order to express a biologically active fusion protein, the nucleotide sequence coding for a chimeric protein, or a functional equivalent, is inserted into an appropriate expression vector, i.e., a vector which contains the necessary elements for the transcription and translation of the inserted coding sequence, as described elsewherein in greater detail. The fusion gene products as well as host cells or cell lines transfected or transformed with recombinant fusion expression vectors can be used for a variety of purposes. These include but are not limited to generating antibodies (i.e., monoclonal or polyclonal) that bind to epitopes of the proteins to facilitate their purification.

Methods that are well known to those skilled in the art can be used to construct expression vectors containing the fusion protein coding sequence and appropriate transcriptional/translational control signals, as discussed elsewhere in greater detail. These methods include in vitro recombinant DNA techniques, synthetic techniques and in vivo recombination/genetic recombination.

A variety of host-expression vector systems may be utilized to express the fusion protein coding sequence, and these are well known in the art.

Specific initiation signals may be required for efficient translation of the inserted fusion protein coding sequence. These signals include the ATG initiation codon and adjacent sequences. In cases where the entire fusion gene, including its own initiation codon and adjacent sequences, is inserted into the appropriate expression vector, no additional translational control signals may be needed. However, in cases where the fusion protein coding sequence does not include its own initiation codon, exogenous translational control signals, including the ATG initiation codon, must be provided. Furthermore, the initiation codon must be in phase with the reading frame of the fusion protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987).

Definitions and Techniques Affecting Targeting Fusion Gene Products and Genes

Targeting Fusion Gene Products and Genes

As used herein, the terms "targeting fusion gene product" and "targeting fusion" refer to proteins or polypeptides having amino acid sequences that comprise at least one anti-angiogenesis component and at least one therapeutic and/or diagnostic component in said fusion and that are biologically active in that they are capable performing similar activities to at least one of their native components, and in some embodiments both components are capable of performing activities similar to the native separate components. For example, they are preferably capable of anti-angiogenesis activity, pro-apoptotic activity, anti-cell proliferative activity, anti-tumor activity and/or cross-reactive antibody activity with an anti-targeting fusion antibody raised against at least one component of the targeting fusion gene product. The term "targeting fusion gene product" includes analogs of targeting fusion molecules that exhibit at least some biological activity in common with native targeting fusion. Furthermore, those skilled in the art of mutagenesis will appreciate that other analogs, as yet undisclosed or undiscovered, may be used to construct targeting fusion analogs.

The term "mutant form of targeting fusion" refers to any DNA sequence that is substantially identical to a DNA sequence encoding at least a part of the targeting fusion gene product as defined above. The term also refers to RNA or antisense sequences compatible with such DNA sequences. A "targeting fusion gene" may also comprise any combination of associated control sequences.

The term "substantially identical", when used to define either a targeting fusion amino acid sequence or targeting fusion nucleic acid sequence, means that a particular subject sequence, for example, a mutant sequence, varies from the sequence of its separate components by, for example, one or more substitutions, deletions, additions, or a combination thereof, the net effect of which is to retain at least some biological activity of at least part of the respective component part. Alternatively, DNA analog sequences are "substantially identical" to specific DNA sequences disclosed herein if: (a) the DNA analog sequence is derived from at least part of a coding region of the targeting fusion gene; or (b) the DNA analog sequence is capable at least in part of hybridization of DNA sequences of (a) under moderately stringent conditions and which encode biologically active targeting fusion; or (c) DNA sequences that are degenerative as a result of the genetic code at least part of to the DNA analog sequences defined in (a) or (b). Substantially identical analog proteins will be greater than about 80% similar to the corresponding sequence of the native protein component. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

Percent Singularity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

Nucleic Acid Sequences

In certain embodiments, the invention concerns the use of targeting fusion nucleic acids, genes and gene products, or the corresponding protein, polypeptide, or peptide. The term "a sequence essentially as targeting fusion" means that the sequence substantially corresponds to at least a portion of the targeting fusion gene and has relatively few bases or amino acids (whether DNA or protein) that are not identical to those of targeting fusion (or a biologically functional equivalent thereof, when referring to proteins). The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to at least part of the amino acids of targeting fusion will be sequences that are "essentially the same".

Targeting fusion nucleic acids that have at least part of their sequence comprising functionally equivalent codons are covered by the invention. The term "functionally equivalent codon" is used herein to refer to codons that encode the same amino acid, such as the six codons for arginine or serine, and also refers to codons that encode biologically equivalent amino acids (Table 1).

| Amino Acids | Codons | |
|---|---|---|
| Alanine | Ala | A GCA GCC GCG GCU |
| Cysteine | Cys | C UGC UGU |

-continued

| Amino Acids | | Codons |
|---|---|---|
| Aspartic Acid | Asp | D GAC GAU |
| Glutamic Acid | Glu | E GAA GAG |
| Phenylalanine | Phe | F UUC UUU |
| Glycine | Gly | G GGA GGC GGG GGU |
| Histidine | His | H CAC CAU |
| Isoleucine | Ile | I AUA AUC AUU |
| Lysine | Lys | K AAA AAG |
| Leucine | Leu | L UUA UUG CUA CUC CUG CUU |
| Methionine | Met | M AUG |
| Asparagine | Asn | N AAC AAU |
| Proline | Pro | P CCA CCC CCU |
| Glutamine | Gln | Q CAA CAG |
| Arginine | Arg | R AGA AGG CGA CGC CGG CGU |
| Serine | Ser | S AGC AGU UCA UCC UCG UCU |
| Threonine | Thr | T ACA ACC ACG ACU |
| Valine | Val | V GUA GUC GUG GUU |
| Tryptophan | Trp | W UGG |
| Tyrosine | Tyr | Y UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments that are complementary, or essentially complementary, to the sequences set forth in the specification. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment in question under relatively stringent conditions such as those described herein.

Biologically Functional Equivalents

As mentioned above, modification and changes may be made in at least part of the structure of angiogenesis inhibitor coupled to a therapeutic or diagnostic agent, such as an antiangiogenesis targeting fusion, and still obtain a molecule having like or otherwise desirable characteristics. In a specific embodiment, a skilled artisan recognizes that the scope of the angiogenesis inhibitor coupled to a therapeutic or diagnostic agent comprises an antiangiogenesis polypeptide region linked to a therapeutic protein or polypeptide region or a diagnostic protein or polypeptide region or a nucleic acid encoding a fusion protein comprising an antiangiogenesis polypeptide region linked to a therapeutic protein or polypeptide region or a diagnostic protein or polypeptide region.

For example, certain amino acids may be substituted for other amino acids in a protein structure without appreciable loss of activity. Since, in many embodiments, it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic vs. agonistic). It is thus contemplated by the inventors that various changes may be made in at least part of the sequence of the targeting fusion proteins or peptides (or underlying DNA) without appreciable loss of their desired biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged.

Amino acid substitutions, such as those that might be employed in modifying targeting fusion, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those that are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

Combination Treatments

In order to increase the effectiveness of an angiogenesis inhibitor coupled to a therapeutic or diagnostic agent, such as an anti-angiogenic targeting fusion protein, or expression construct coding therefore, it may be desirable to combine these compositions with other agents effective in the treatment of disease related to angiogenesis, such as, for example, anti-cancer agents for cancer. An "anti-cancer" agent is capable of negatively affecting cancer in a subject, for example, by inhibiting angiogenesis for a cancer cell and/or tissue, killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that targeting fusion gene therapy could be used similarly in conjunction with chemotherapeutic, radiotherapeutic, or immunotherapeutic intervention, in addition to other pro-apoptotic or cell cycle regulating agents.

Alternatively, the combination therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations, in an exemplary embodiment, may be employed, although gene therapy is "A" and the secondary agent, such as radiotherapy, chemotherapy, surgery, or immunotherapy is "B":

A/B/A B/A/B B/B/A A/A/B A/B/B B/A/A A/B/B/B

B/A/B/B B/B/B/A B/B/A/B A/A/B/B A/B/A/B A/B/B/A

B/B/A/A B/A/B/A B/A/A/B A/A/A/B B/A/A/A A/B/A/A

A/A/B/A

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

Nucleic Acid-Based Expression Systems

Vectors

In one embodiment, a targeting fusion nucleic acid is comprised on a vector. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202; 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

In a specific embodiment, a promoter is utilized that is tissue-specific and/or specific to the microenvironment surrounding the diseased tissue (such as the tumor), cell-specific, or cell type-specific. In a specific embodiment, a promoter such as one described in U.S. Provisional Patent Application Ser. No. 60/377,672, filed May 5, 2002, and entitled "BIPARTITE T-CELL FACTOR (TCF)-RESPONSIVE PROMOTER" and in U.S. Nonprovisional patent application Ser. No. 10/429,802, filed May 5, 2003 under Express Mail number EU 110397859US, both of which are incorporated by reference herein in their entirety, is utilized in the present invention.

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia*

*methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Nucleic Acid Delivery

The general approach to the aspects of the present invention concerning compositions and/or therapeutics is to provide a cell with a gene construct encoding a specific and/or desired protein, polypeptide and peptide, thereby permitting the desired activity of the proteins to take effect. In the present invention, the desired protein, polypeptide, or peptide is a targeting fusion comprising an angiogenesis inhibitor and a therapeutic or diagnostic sequence. While it is conceivable that the gene construct and/or protein may be delivered directly, a preferred embodiment involves providing a nucleic acid encoding a specific and desired protein, polypeptide and peptide to the cell. Following this provision, the proteinaceous composition is synthesized by the transcriptional and translational machinery of the cell, as well as any that may be provided by the expression construct. In providing antisense, ribozymes and other inhibitors, the preferred mode is also to provide a nucleic acid encoding the construct to the cell.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments and "episomes" encode sequences sufficient to permit maintenance and replication independent of and in synchronization with the host cell cycle. How the expression construct is delivered to a cell and/or where in the cell the nucleic acid remains is dependent on the type of expression construct employed.

DNA Delivery Using Viral Vectors

The ability of certain viruses to infect cells and enter cells via receptor-mediated endocytosis, and to integrate into host cell genome and/or express viral genes stably and/or efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and/or in the range of cells they infect, these viruses have been demonstrated to successfully effect gene expression. However, adenoviruses do not integrate their genetic material into the host genome and/or therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles and endotoxins and other pyrogens such that it will not cause any untoward reactions in the cell, animal and/or individual receiving the vector construct. A preferred means of purifying the vector involves the use of buoyant density gradients, such as cesium chloride gradient centrifugation Adenoviral Vectors A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and/or (b) to ultimately express a tissue and/or cell-specific construct that has been cloned therein.

The expression vector comprises a genetically engineered form of adenovirus. Knowledge of the genetic organization and adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and/or no genome rearrangement has been detected after extensive amplification.

Adenovirus is particularly suitable for use as a gene transfer vector because of its mid-sized genome, ease of manipulation, high titer, wide target-cell range and/or high infectivity. Both ends of the viral genome contain 100-200 base pair inverted repeats (ITRs), which are cis elements necessary for viral DNA replication and/or packaging. The early (E) and/or late (L) regions of the genome contain different transcription units that are divided by the onset of viral DNA replication. The E1 region (E1A and/or E1B) encodes proteins responsible for the regulation of transcription of the viral genome and/or a few cellular genes. The expression of the E2 region (E2A and/or E2B) results in the synthesis of the proteins for viral DNA replication. These proteins are involved in DNA replication, late gene expression and/or host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and/or all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and/or examine its genomic structure.

Generation and/or propagation of the current adenovirus vectors, which are replication deficient, depend on a unique helper cell line, designated 293, which was transformed from human embryonic kidney cells by Ad5 DNA fragments and constitutively expresses E1 proteins (E1A and/or E1B; Graham et al., 1977). Since the E3 region is dispensable from the adenovirus genome (Jones and Shenk, 1978), the current adenovirus vectors, with the help of 293 cells, carry foreign DNA in either the E1, the D3 and both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and/or E3 regions, the maximum capacity of the current adenovirus vector is under 7.5 kb, and/or about 15% of the total length of the vector. More than 80% of the adenovirus viral genome remains in the vector backbone.

Helper cell lines may be derived from human cells such as human embryonic kidney cells, muscle cells, hematopoietic cells and other human embryonic mesenchymal and epithelial cells. Alternatively, the helper cells may be derived from the cells of other mammalian species that are permissive for human adenovirus. Such cells include, e.g., Vero cells and other monkey embryonic mesenchymal and/or epithelial cells. As stated above, the preferred helper cell line is 293.

Recently, Racher et al. (1995) disclosed improved methods for culturing 293 cells and/or propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and/or left stationary, with occasional agitation, for 1 to 4 h. The medium is then replaced with 50 ml of fresh medium and/or shaking initiated. For virus production, cells are allowed to grow to about 80% confluence, after which time the medium is replaced (to 25% of the final volume) and/or adenovirus added at an MOI of 0.05. Cultures are left stationary overnight, following which the volume is increased to 100% and/or shaking commenced for another 72 h.

Other than the requirement that the adenovirus vector be replication defective, and at least conditionally defective, the nature of the adenovirus vector is not believed to be crucial to the successful practice of the invention. The adenovirus may be of any of the 42 different known serotypes and subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vector as described by Karlsson et al. (1986) and in the E4 region where a helper cell line and helper virus complements the E4 defect.

Adenovirus growth and/or manipulation is known to those of skill in the art, and/or exhibits broad host range in vitro and in vivo. This group of viruses can be obtained in high titers, e.g., 109 to 1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and/or therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991a; Stratford-Perricaudet et al., 1991b; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and/or stereotactic inoculation into the brain (Le Gal La Salle et al., 1993). Recombinant adenovirus and adeno-associated virus (see below) can both infect and transduce non-dividing human primary cells.

AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) and in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and/or U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and/or in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus and a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome and from a recombinant plasmid, and/or a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and/or an expression plasmid containing the wild type AAV coding sequences without the terminal repeats, for example pIM45 (McCarty et al., 1991; incorporated herein by reference). The cells are also infected and transfected with adenovirus and plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions and cell lines containing the AAV coding regions and some and all of the adenovirus helper genes could be used (Yang et al., 1994; Clark et al., 1995). Cell lines carrying the rAAV DNA as an integrated provirus can also be used (Flotte et al., 1995).

Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and/or directs synthesis of viral proteins. The integration results in the retention of the viral gene sequences in the recipient cell and/or its descendants. The retroviral genome contains three genes, gag, pol, and/or env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and/or stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

Specific retroviral vectors useful in the present invention include lentivirus and Vesicular Stomatitis Virus-Indiana.
Other Viral Vectors Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and/or herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and/or pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes and expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and/or can be grown to high titers. Thus, delivery is less of a problem, both in terms of volumes needed to attain sufficient MOI and in a lessened need for repeat dosings
Modified Viruses In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and/or against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).
Other Methods of DNA Delivery In various embodiments of the invention, DNA is delivered to a cell as an expression construct. In order to effect expression of a gene construct, the expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA and/or plasmids. Transfer of the construct may be performed by any of the methods mentioned which physically and/or chemically permeabilize the cell membrane. Some of these techniques may be successfully adapted for in vivo and/or ex vivo use, as discussed below.

Liposome-Mediated Transfection

In a further embodiment of the invention, the expression construct may be entrapped in a liposome. Liposomes are vesicular structures characterized by a phospholipid bilayer membrane and/or an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and/or entrap water and/or dissolved solutes between the lipid bilayers (Ghosh and Bachhawat, 1991). Also contemplated is an expression construct complexed with Lipofectamine (Gibco BRL). Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and/or expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and/or promote cell entry of liposome-encapsulated DNA (Kaneda et al., 1989). In other embodiments, the liposome may be complexed and/or employed in conjunction with nuclear non-histone chromosomal proteins (HMG-1) (Kato et al., 1991). In yet further embodiments, the liposome may be complexed and/or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

As described in U.S. Pat. No. 5,641,484, liposomes are particularly well suited for the treatment of HER2/neu-mediated cancer Preparation of Liposomes Catatonic liposomes that are efficient transfection reagents for targeting fusion for animal cells can be prepared using the method of Gao et al. (1991). Gao et al. describes a novel catatonic cholesterol derivative that can be synthesized in a single step. Liposomes made of this lipid are reportedly more efficient in transfection and less toxic to treated cells than those made with the reagent Lipofectin. These lipids are a mixture of DC-Chol ("3'(N—(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloroform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 µmol of DC-Chol and 8.0 µmol of DOPE in chloroform. This mixture is then dried, vacuum desiccated, and resuspended in 1 ml sterol 20 mM Hepes buffer (pH 7.8) in a tube. After 24 hours of hydration at 4° C., the dispersion is sonicated for 5-10 minutes in a sonicator form liposomes with an average diameter of 150-200 nm.

To prepare a liposome/DNA complex, the inventors use the following steps. The DNA to be transfected is placed in DMEM/F12 medium in a ratio of 15 µg DNA to 50 µl DMEM/F12. DMEM/F12 is then used to dilute the DC-Chol/DOPE liposome mixture to a ratio of 50 µl DMEZM/F12 to 100 µl liposome. The DNA dilution and the liposome dilution are then gently mixed, and incubated at 37° C. for 10 minutes. Following incubation, the DNA/liposome complex is ready for injection.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3.beta.[N—(N'N'-dimethylaminoethane)-carbamoyl cholesterol (DC-Chol), as well as other lipids known to those of skill in the art. Those of skill in the art will recognize that there are a variety of liposomal transfection techniques which will be useful in the present invention. Among these techniques are those described in Nicolau et al., 1987, Nabel et al, 1990, and Gao et al., 1991. In a specific embodiment, the liposomes comprise DC-Chol. More particularly, the inventors the liposomes comprise DC-Chol and DOPE which have been prepared following the teaching of Gao et al. (1991) in the manner described in the Preferred Embodiments Section. The inventors also anticipate utility for liposomes comprised of DOTMA, such as those which are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allow liposome-mediated transfer of DNA complex, for example, the liver and the spleen. In order to allow transfection of DNA into cells which are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a nucleic acid encoding an anti-angiogenic targeting fusion. The nucleic acid encoding the targeting fusion employed in the liposomal complex can be, for example, one which encodes targeting fusions described herein.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

In a specific embodiment, one employs the smallest region needed to enhance retention of targeting fusion in the nucleus of a cell so that one is not introducing unnecessary DNA into cells which receive a targeting fusion gene construct. Techniques well known to those of skill in the art, such as the use of restriction enzymes, will allow for the generation of small regions of targeting fusion. The ability of these regions to inhibit neu can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

In vivo Treatment of Cancer Via Liposomes with Targeting Fusions

Based on the teachings provided herein, a skilled artisan recognizes that any cell may be treated with at least one targeting fusion, and in particular embodiments, any cancer cell may be treated with such. For example, in some embodiments the nature of the treated cell is irrespective of being HER2/neu-positive or HER2/neu-negative.

U.S. Pat. No. 5,641,484, incorporated in its entirety by reference herein, teaches that liposome-mediated direct gene transfer techniques can be employed to obtain suppression of HER2/neu-overexpressing human cancer cells in living host. The exemplary protocol for described therein was as follows. Female nude mice (5-6 weeks old) were given intraperitoneal injections of SK-OV-3 cells ($2\times10^6$/100 µl). SK-OV-3 cells are human ovarian cancer cells that have been shown to grow within the peritoneal cavity of nude mice. After five days, the mice were given intraperitoneal injections of various compounds. Some mice were injected with the therapeutic DNA alone, some were injected with liposome/therapeutic DNA complex prepared in the manner described above, and some were injected with liposome/mutant therapeutic DNA complex. 200 µl of a given compound was injected into a given mouse. After the initial injections, injections were repeated every seven days throughout the life of the mouse.

The results described therein indicate that liposome-mediated gene transfer can inhibit HER2/neu-overexpressing human ovarian cancer cell growth. Therefore, it is predictable that liposome-mediated targeting fusion gene therapy may serve as a powerful therapeutic agent for HER-2 neu-overexpressing human ovarian cancers by direct targeting of targeting fusion at the HER-2 neu-oncogene.

Liposomal Transfection with Targeting fusion to Treat Humans

Based on the results of the in vivo animal studies described in U.S. Pat. No. 5,641,484, those of skill in the art will understand and predict the enormous potential for human treatment of HER2/neu-mediated cancers with an anti-angiogenic targeting fusion complexed to liposomes. Clinical studies to demonstrate these effects are contemplated. Those of skill in the art will recognize that the best treatment regimens for using targeting fusions to suppress cancers can be straightforwardly determined. This is not a question of experimentation, but rather one of optimization, which is routinely conducted in the medical arts. In vivo studies in nude mice provide a starting point from which to begin to optimize the dosage and delivery regimes. The frequency of injection is initially once a week, as was done in the mice studies described in U.S. Pat. No. 5,641,484. However, this frequency might be optimally adjusted from one day to every two weeks to monthly, depending upon the results obtained from the initial clinical trials and the needs of a particular patient. Human dosage amounts can initially be determined by extrapolating from the amount of targeting fusion used in mice, approximately 15 µg of plasmid DNA per 50 g body weight. Based on this, a 50 kg woman would require treatment with 15 mg of DNA per dose. Of course, this dosage amount may be adjusted upward or downward, as is routinely done in such treatment protocols, depending on the results of the initial clinical trials and the needs of a particular patient. These clinical trials are anticipated to show utility of targeting fusions for the treatment of HER2/neu-overexpressing cancers in humans. Dosage and frequency regimes will initially be based on the data obtained from in vivo animal studies, as is done frequently in the art Electroporation In certain embodiments of the present invention, the expression construct is introduced into the cell via electroporation. Electroporation involves the exposure of a suspension of cells and/or DNA to a high-voltage electric discharge.

Transfection of eukaryotic cells using electroporation has been quite successful. Mouse pre-B lymphocytes have been transfected with humankappa-immunoglobulin genes (Potter et al., 1984), and/or rat hepatocytes have been transfected with the chloramphenicol acetyltransferase gene (Tur-Kaspa et al., 1986) in this manner.

Calcium Phosphate and/or DEAE-Dextran

In other embodiments of the present invention, the expression construct is introduced to the cells using calcium phosphate precipitation. HumanKB cells have been transfected with adenovirus 5 DNA (Graham and Van Der Eb, 1973) using this technique. Also in this manner, mouse L(A9), mouse C127, CHO, CV-1, BHK, NIH3T3 and/or HeLa cells were transfected with a neomycin marker gene (Chen and Okayama, 1987), and/or rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and/or erythroleukemia cells (Gopal, 1985).

Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and/or enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten and/or gold beads.

Direct Microinjection and/or Sonication Loading

Further embodiments of the present invention include the introduction of the expression construct by direct microinjection and/or sonication loading. Direct microinjection has been used to introduce nucleic acid constructs into *Xenopus* oocytes (Harland and Weintraub, 1985), and/or LTK-fibroblasts have been transfected with the thymidine kinase gene by sonication loading (Fechheimer et al., 1987).

Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

Pharmaceutical Preparations

Pharmaceutical compositions of the present invention comprise an effective amount of one or more forms of an angiogenesis inhibitor coupled to a therapeutic or diagnostic agent, such as an anti-angiogenesis targeting fusion and/or additional agent dissolved or dispersed in a pharmaceutically acceptable carrier or excipient. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one targeting fusion form or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The targeting fusion form may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The targeting fusion form may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the targeting fusion form is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

In a particular embodiment of the present invention, a composition is utilized wherein the composition is an antiangiogenic targeting fusion, the expression of which is regulated at least in part by a promoter comprising one such as is described in U.S. Provisional Patent Application Ser. No. 60/377,672, filed May 5, 2002, and entitled "BIPARTITE T-CELL FACTOR (TCF)-RESPONSIVE PROMOTER" and in U.S. Nonprovisional patent application Ser. No. 10/429, 802, filed May 5, 2003 under Express Mail number EU 110397859US, both of which are incorporated by reference herein in their entirety, and wherein said fusion is comprised with a liposome, such as DC-Chol, DOTMA, and the like.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Immunoblotting: The endostatin, endostatin-cytosine deaminase (endo-CD), and endostatin-interleukin-12 (endo-IL12) containing plasmid was used to transfect 293T cells using the cationic liposome method. After transfection, the medium was replaced by serum free medium. Then, after a 24 hr incubation, the supernatant was collected and western blotted with anti-endostatin antibody.

ELISA: COS-7 cells were transfected with plasmids encoding either, Endostatin-IL2 or Endostatin-GM-CSF using cationic liposome. After transfection, the medium was replaced with serum free medium and the supernatant was harvested and subjected to ELISA to detect the endostatin protein.

Example 2

Expression of Antiangiogenic-Therapeutic/Diagnostic Fusion Genes

FIG. 1 shows that following production of fusion protein, antiangiogenic-therapeutic/diagnostic fusion protein could be detected. In FIG. 1A, there is an anti-endostatin antibody Western blot of supernatants collected from 293 cells. Eighteen KD endostatin(□), 58 KD endostatin-CD (◄), and 93 KD endo-IL12(←) could be detected. FIG. 1B illustrates that by using ELISA kit (specific for endostatin), endostatin-IL2 and endostatin-GM-CSF fusion proteins could also be detected and quantified.

Example 3

Exemplary Materials and Methods for Characterizing Antiangiogenic and Therapeutic/Diagnostic Functions of the Fusion Proteins Endothelial tube assay: Matrigel (Collaborative Biomolecules, Bedford, Mass.) was added (50 µl) to each well of a 96-well plate and allowed to polymerize. A suspension of 5,000 human umbilical endothelial cells (HUVEC) in EGM-2 medium without antibiotic was passed into each well coated with matrigel. The cells were treated with supernatants collected from different plasmid (endostatin, endostatin-CD, and CD) transfected 293T cells. All assays were performed in triplicate. Cell were incubated for 12-24 hr at 37° C. and viewed using a microscope. The cells were then photographed. Five fields were viewed, and tubes were counted and averaged.

Migration assay: The inhibitory effect of endostatin on VEGF-induced chemotaxis was tested on HUVECs using the Boyden chamber assay. After trypsinizing, washing, and diluting cells in M199 medium containing 0.5% FBS, 10,000 cells were seeded on the upper chamber wells, together with supernatant collected from 293T transfected with different plasmid (endostatin, endostatin-CD, and CD). M199 medium containing 2% FBS plus 10 ng/ml VEGF was placed in the lower chamber as a chemotactant. The cell-containing compartments were separated from the chemotactant with polycarbonate filter of 8 um pore size. The chamber was incubated at 37° C. for 6-8 hr. After discarding the non-migrated cells and washing the upper wells with PBS, the filters were scraped with a plastic blade, fixed in 4% formaldehyde in PBS, stained with DAPI fluorescent stain and placed on a glass slide. By using a fluorescent high power field, several independent homogenous images were recorded. Five fields were viewed, and tubes were counted and averaged. All assays were performed in triplicate.

MTT assay: The cytotoxic effect of 5FU converted from 5FC reacted with cytosine deaminase (CD) was 293T cells using MTT assay. The inventors use different plasmid (endostatin, endostatin-CD, and CD) to transfect 293T cells and incubated 12-14 hrs. After trypsinizing, washing, and diluting cells in DMEM medium containing 2% FBS plus different concentration of 5FU or 5FC, 5,000 cells were seeded on each well of 96-well plate. Then the plate was incubated at 37° C. for 3-4 days. The inventors add 20 µl of MTT solution and incubate for 2 hr, then 100 µl of lysing solution was added to each well and incubated overnight night. The light absorbance was measured at 570 nm on the following day.

Green fluorescence expression: The endostatin-GFP containing plasmid was used to transfect 293T cells with the same method. After 36 hr incubation, the GFP fluorescence was observed under fluorescent microscope.

NSF60 (GM-CSF dependent) Cell proliferation assay: To quantify the biological activity of the Endostatin-GM-CSF, the factor dependent cell line NSF60 was used. NSF60 cells were incubated with condition medium from COS-7 cells transfecte with either control plasmid, plasmid encoding Endostatin-GM-CSF, or two different concentrations of recombinant GM-CSF. After 48 hr of incubation, NSF60 proliferation was determined by measuring the activity of dehydrogenase-enzyme as marker for the biological activity, using 2 mg/ml Cell Titer 96™ MTS Reagent Powder (3-(4, 5-dimethylthiazol-2-yl)-5-(3-carboxymethoxyphenyl) -2-(4-sulfophenyl) -2H-tetrazolium inner salt) (Promega, USA) and 0.92 mg/ml Phenazine methosulfate (Sigma, USA). The $OD_{405}$ values reflected the cell numbers.

Example 4

Figure 2:
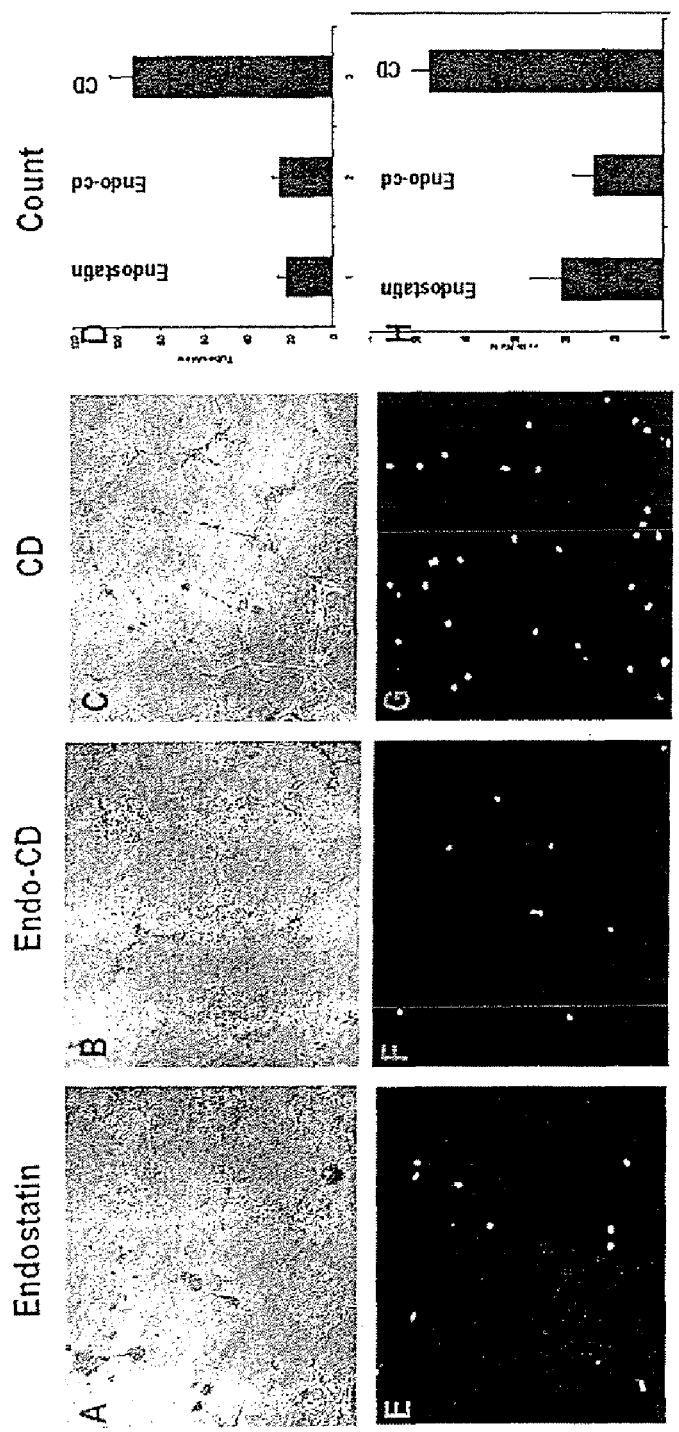
FIGS. 2A through 2H show that, in comparison to endostatin, endo-CD fusion protein exhibited similar antiangiogenic effects in endothelial tube (2A-2D) and migration (2E-2H) assays.

Fusion Proteins Possess Both Antiangiogenic and Therapeutic/Diagnostic Functions FIG. 2 shows that, in comparison to endostatin, endo-CD fusion protein exhibit similar antiangiogenic effects in endothelial tube (FIGS. 2A-2D) and migration (FIGS. 2E-2H) assays. As supernatant collected from endostatin gene transfection, the supernatant from endostatin-CD fusion gene demonstrated inhibitory effect on HUVEC cell tube formation (FIGS. 2A, 2B, and 2C) and cell migration (FIGS. 2E, 2F, and 2G). In FIGS. 2D and 2H, five fields were viewed, and the tubes or migrated cells were counted and averaged.

Figure 3:
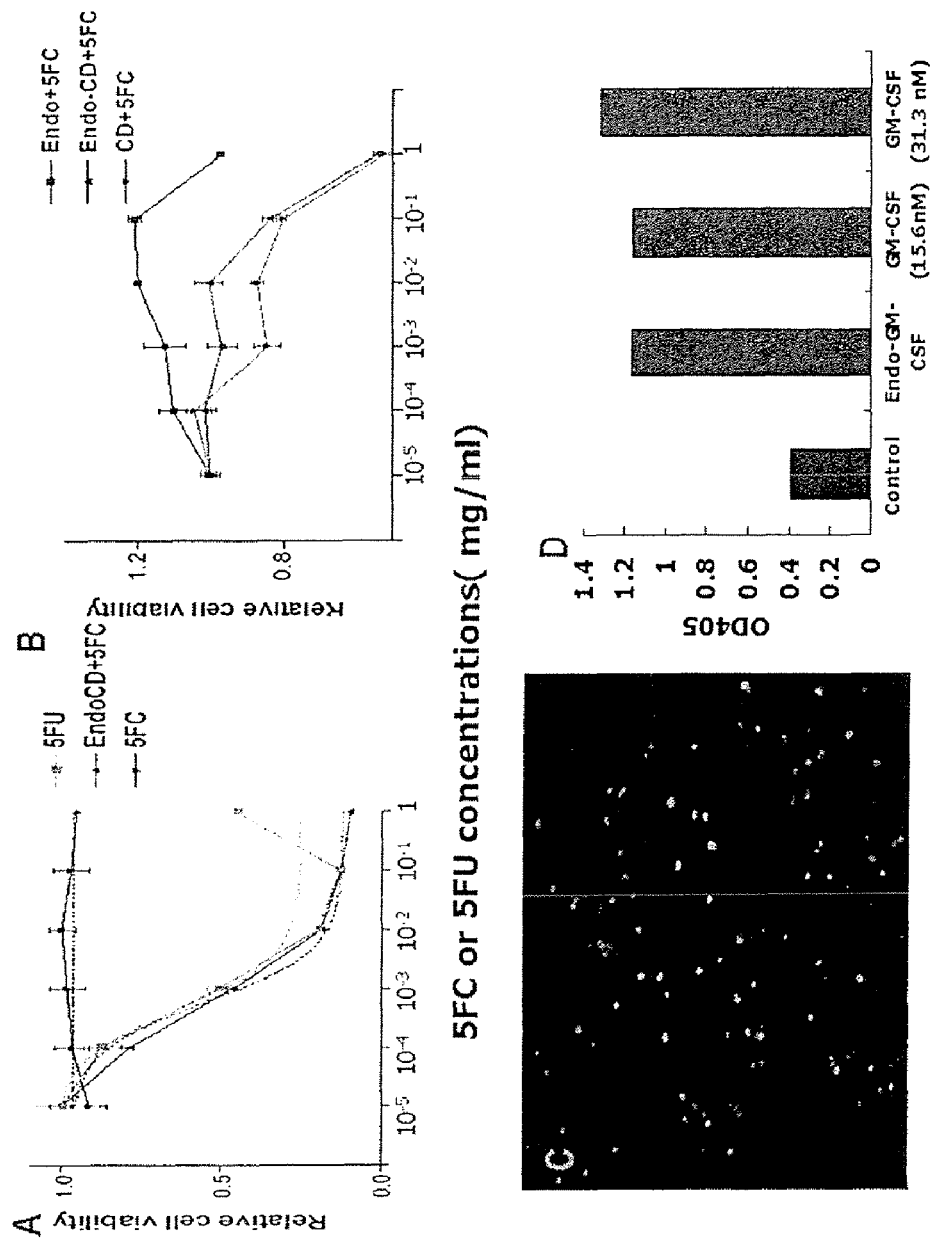
FIGS. 3A through 3D demonstrate that therapeutic or diagnostic functions of fusion genes could be detected.

FIG. 3 illustrates that therapeutic or diagnostic functions of fusion genes could be detected. In FIGS. 3A and 3B, a MTT assay is provided. As different concentrations of 5FU or 5FC with CD gene transfection were provided, endo-CD gene transfection demonstrated the killing effect on 293T cells. In FIG. 3C, green fluorescent protein expression in 293T cells transfected with Endo-GFP fusion gene could be detected by fluorescent microscope. In FIG. 3D, the cell proliferation of NSF60 could be stimulated by conditional medium from COS-7 transfected by Endostatin-GM-CSF plasmid. $OD_{405}$ values of NSF60 incubated with conditional medium from COS-7 transfected by Endostatin-GM-CSF plasmid was slightly better than those cells incubated with 15.6 nM recombinant GM-CSF protein. Therefore, the protein encoded by Endostatin-GM-CSF plasmid exhibited GM-CSF function, as evidenced by proliferation of GM-CSF dependent NSF60.

Example 5

Exemplary Materials and Methods for Tumor-Specific Targeting Effect of Antiangiogenic-Therapeutic/Diagnostic Fusion Proteins In vitro Endothelial Cell Targeting To demonstrate the specific targeting effect of antiangiogenic/therapeutic or antiangiogenic/diagnostic fusion gene, the inventors seeded the previously established 293T endostatin-GFP stable clone to a 10 cm plate. At the same time, different cell lines (MDA-231 breast cancer cell, mouse endothelial cell-SVEC, and human endothelial cell-HUVEC) were seeded to a 4-chamber plate. After the cells attached, the inventors put the 4-well plate into the 10 cm plate and added enough medium to cover all the wells. After 48 hr incubation, the 4-well plate was washed with PBS and the green fluorescence was observed under the fluorescent microscope.

In vivo Tumor Targeting

The inventors subcutaneously injected $2\times10^5$ B16 cells from parental cell line or endostatin-GFP stable clone to 7-9-week-old B57 mice. Each mice bears two injection sites. In experimental group, the inventors injected B16 parental cells to one site and B16 endostatin-GFP cells to the other. In control group, both sites received the tumor cells from B16 parental cells. After 14 days, the tumors were harvested and fixed. The inventors use anti-GFP antibody for immunohistochemical staining.

Example 6

Figure 4:
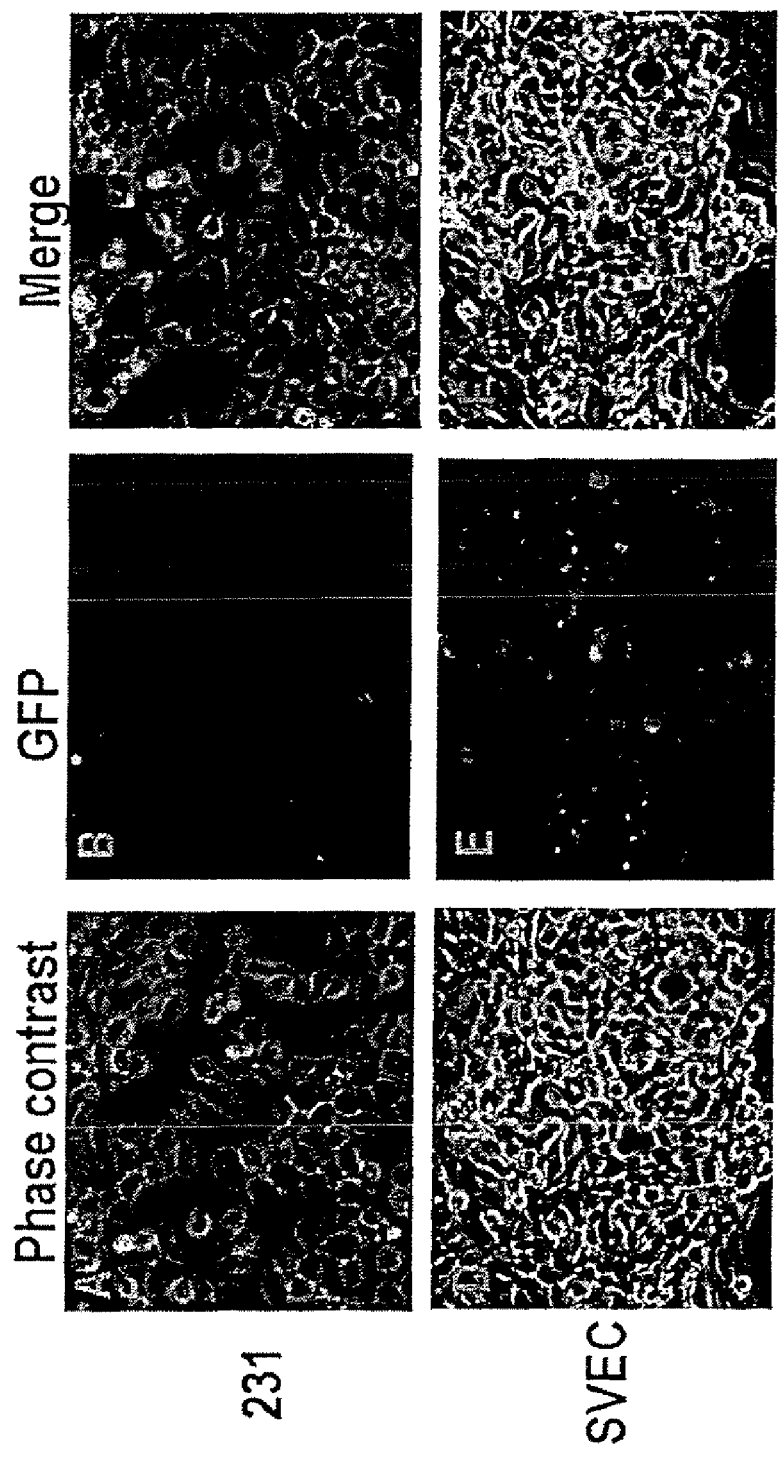
FIGS. 4A through 4F demonstrate that endostatin-GFP specifically targets to endothelial cells.

Tumor Specific Targeting Effect of Antiangiogenic-Therapeutic/Diagnostic Fusion Proteins FIG. 4 shows that endostatin-GFP specifically targets to endothelial cells. After being incubated with 293T endostatin-GFP stable clone for 48 hr, a lot of green fluorescent signals could be detected in SVEC mouse endothelial cell (E) but not in MDA-231 breast cancer cells (B).

Figure 5:
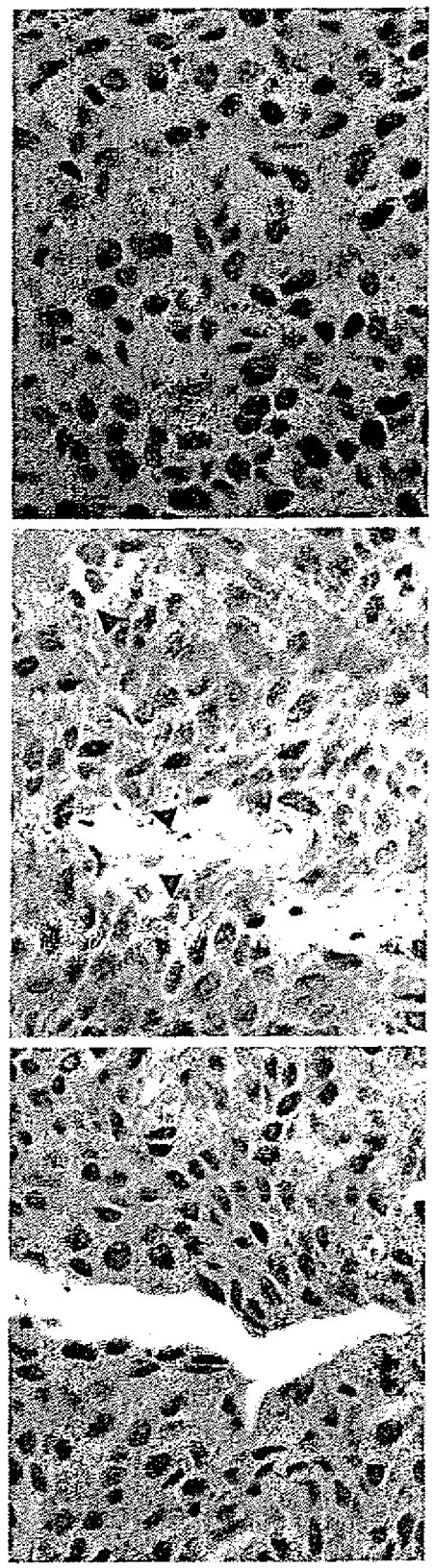
FIGS. 5A through 5C show that GFP signal was detected in the vascular wall of B-16 parental tumors.
In FIG. 5D stable line treatment of endostatin-IL12 against distant tumor is provided.

FIG. 5 GFP signal was detected in the vascular wall of B-16 parental tumors. FIG. 5A demonstrates an experimental group. Diffuse GFP signal was found in tumor of B-16 endostatin-GFP stable cell lines. FIG. 5B shows in contra-lateral tumor to A (from B-16 parental cell lines), GFP signal was found in blood vessel wall (◄). In FIG. 5C, there is no GFP signals could be detected in tumors from bilateral B-16 parental cell lines in control group.

Example 7

Exemplary Materials and Methods for Animal Models of

Endostatin-GFP Inhibit Both Regional and Distant Tumor Growth

Endostatin-GFP plasmid was used to transfect B16 melanoma cell. After the stable clones were established, the inventors subcutaneously injected $2\times10^5$ B16 cells from parental cell line or endostatin-GFP stable clone to 7-9-week-old B57 mice. The animals were divided into two groups. Each group contained 10 mice, and every mice had two injection sites. In the experimental group, the inventors injected B16 parental cells to one site and B16 endostatin-GFP cells to the other. In the control group, both sites received the tumor cells from B16 parental cells. The tumors were measured and calculated on the 14th day. Volume ± S.D. is plotted.

Superior Anticancer Effect of Fusion Proteins Against Regional Tumor

B16F10 melanoma tumor model—Either $1\times10^6$ cells or $2.5\times10^5$ cells of B16-F10 were injected subcutaneously into the right flank of 6-7 week-old C57/BL6 immunocompetent female mice. Four days after inoculation, tumors (about 5 mm in diameter) were directly injected with different plasmid DNA encoding Luciferase, Endostatin, IL12, or Endostatin-IL12 and cationic liposome complexes (in 100 µl saline). The treatment was repeated three times a day for every four days. Seventeen days after the tumor was inoculated, the tumor sizes of each experimental group were measured.

CT-26 colon cancer model—CT-26 colon cancer cells ($2\times10^5$) were injected subcutaneously into 7-9-week-old B57CL6 mice on right flank. Simultaneously, another set of CT-26 melanoma cells ($2\times10^5$) were injected subcutaneously into the left flank of the mice. Four days after the tumor was challenged, different plasmids containing either Luciferase (Luc), endostatin (Endo), interleukin-12 (IL-12), or Endo-IL12 fusion gene were intratumorally injected into the left flank CT-26 tumor. This procedure was repeated twice a week, and the tumor size was measured every two days. The size of distant tumor on the right flank was calculated and plotted over the treatment period.

Example 8

Animal Models of Antiangiogenic-Therapeutic/Diagnostic Fusion Proteins

Figure 6:
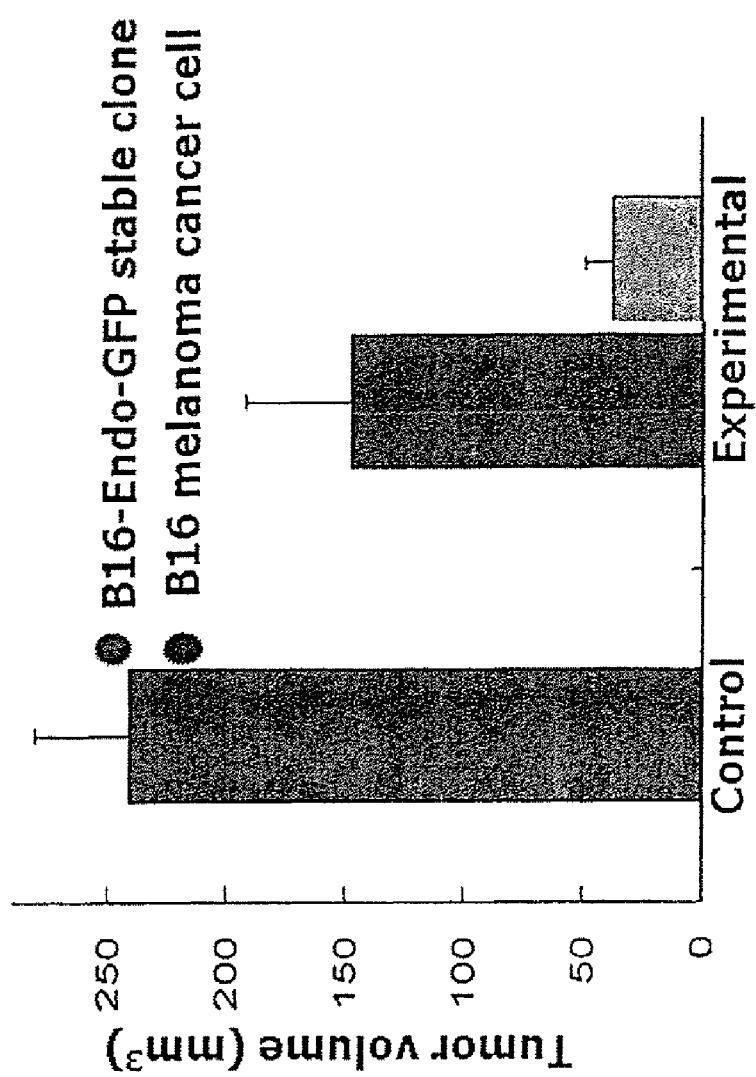
FIG. 6 shows that stable clone-expressed endostatin-GFP inhibits contra-lateral and local tumor growth. In a control group, all of the tumors were measured and averaged together. The tumors in the experimental group were measured and averaged according to their cell lines (B16 parental melanoma cell line or endostatin-GFP stable clones).

FIG. 6 shows stable clone-expressed endostatin-GFP inhibits contra-lateral and local tumor growth. In a control group, all the tumors were measured and averaged together. The tumors in an experimental group were measured and averaged according to their cell lines (B16 parental melanoma cell line or endostatin-GFP stable clones).

Figure 7:
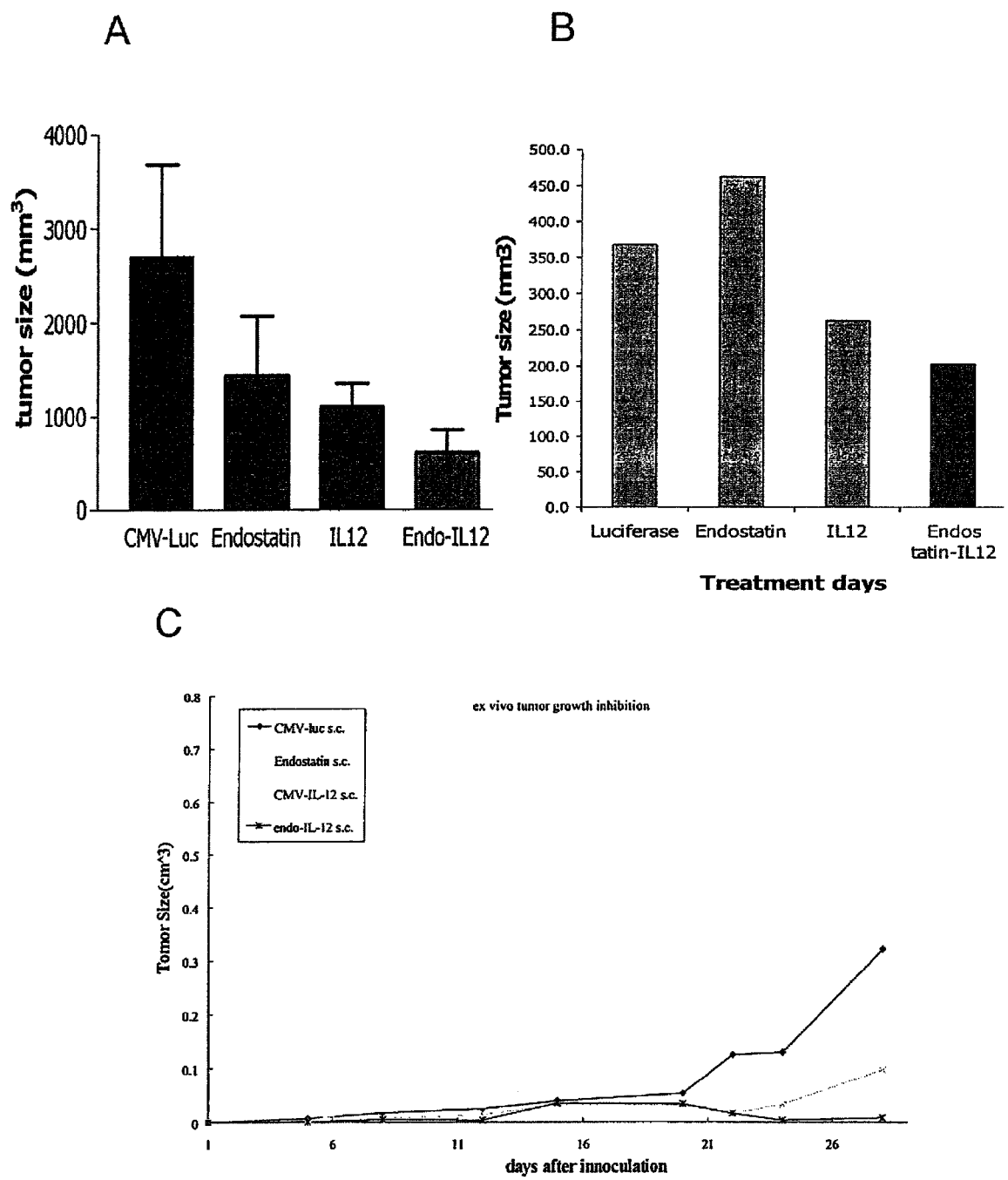
FIGS. 7A through 7C demonstrate that endo-IL12 has a superior anticancer effect compared with IL12 or endostatin alone in different independent animal studies.

FIG. 7 shows that endo-IL12 has a superior anticancer effect compared to IL12 or endostatin alone in different independent animal studies. In FIG. 7A, there is intratumoral gene therapy against B16F10 tumor. Endostatin-IL12 demonstrates the most significant anti-cancer effect on subcutaneous xenograft B16-F10 melanoma cancer compared to both endostatin and IL12 genes. In FIG. 7B, there is similar intratumoral gene therapy as in FIG. 7A against B16F10 tumor, except the original distant tumor was challenged at $2\times10^5$ cell. The endo-IL12 still showed better therapeutic effect than IL12 and endostatin alone, as provided in FIG. 7C.

Example 9

Materials and Methods for Anticancer Effect of Fusion Proteins Against Distant Tumor Ex vivo transfection: B16-F10 melanoma cells ($2\times10^5$) were injected subcutaneously into 7-9-week-old B57CL6 mice on right flank on day 0. All groups contained 10 mice. The inventors used the different plasmids containing either Luciferase (Luc), endostatin (Endo), cytosine deaminase (CD) and endostatin-CD (endo-CD), antiangiogenic deletion mutant of tumstatin (tum5), interleukin-12 (IL-12), or Tum5-IL12 fusion gene to transfect the B16F10 melanoma cells. After transfection, these melanoma cells were harvested and injected into the left flank of the mice in a different group on day 1. This procedure was repeated 3 more times on day 4, 7, 10. Distant tumors on the right flank were measured, and the volume was calculated and plotted over the treatment period.

Stable clones: B16-F10 melanoma cells ($2\times10^5$) were injected subcutaneously into 7-9-week-old B57CL6 mice on the right flank. Two days after, $2\times10^5$ of endostatin, IL12 or endo-IL12 expressing stable clones of B16F10 cancer cells were injected subcutaneously on the left flank. The stable clone cancer cells were repeat injected twice a week. The size of distant tumor on the right flank was measured every two days.

Example 10

Superior Anticancer Effect of Fusion Proteins Against Distant Tumor

Figure 8:
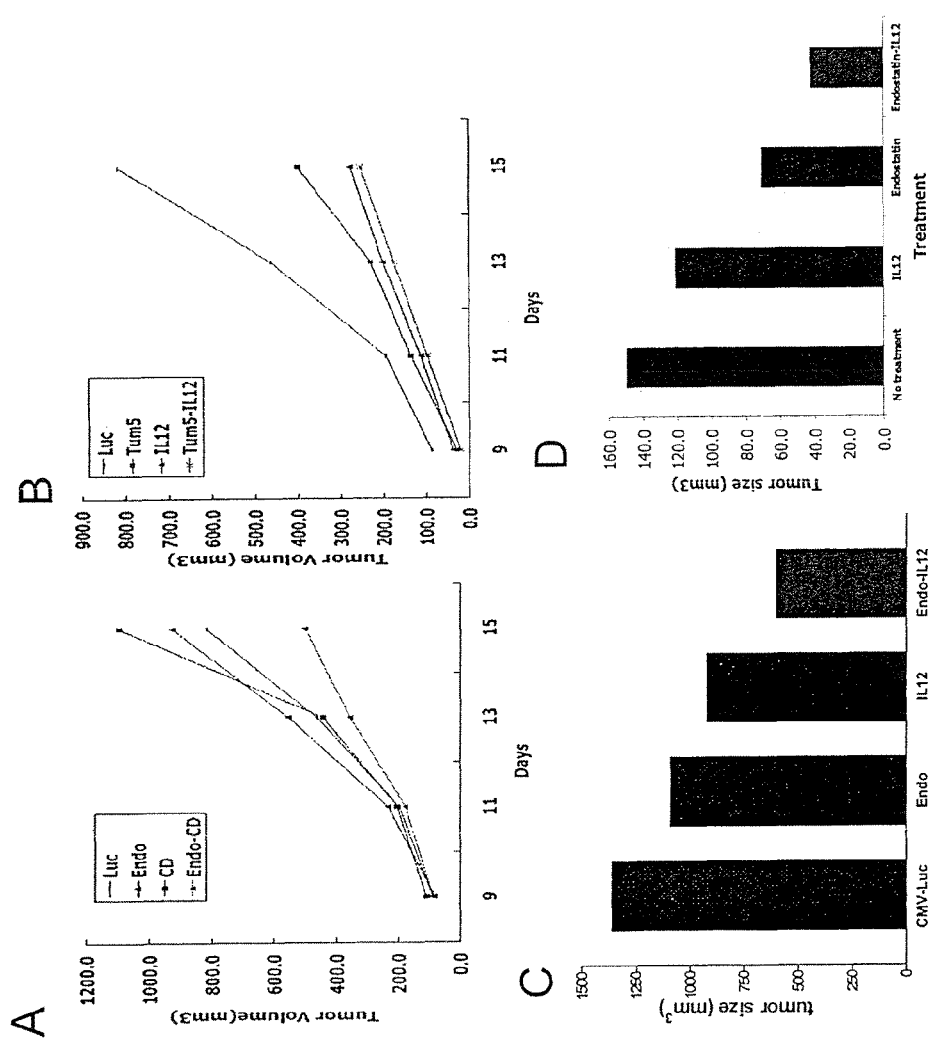
FIGS. 8A through 8D show superior anticancer effect on distant tumor of fusion proteins expressed by either stable clones or ex vivo transfection.

FIG. 8 demonstrates a superior anticancer effect on distant tumor of fusion proteins expressed by either stable clones or ex vivo transfection. In FIG. 8A, ex vivo treatment of endostatin-CD fusion gene of antiangio-chemotherapy showed better inhibitory effect on contra-lateral tumor growth. (Endo: endostatin; CD: cytosine deaminase; Endo-CD: fusion gene). FIG. 8B shows that ex vivo treatment of Tum5-IL12 fusion gene of antiangio-immunotherapy showed better tumor inhibitory effect on distant tumor (Tum5: tumstatin antiangiogenic deletion mutant, IL12: interleukin-12, Tum5-IL12: fusion gene). FIG. 8C provides that distant CT26 colon cancer growths were most significantly inhibited by Endo-IL12 gene therapy. Various genes were injected into CT26 tumor sites distant from the measured tumors, which were not treated with direct injection of genes. FIG. 8D shows stable line treatment of endostatin-IL12 against distant tumor. Endo-IL12 showed better anti-cancer effect than other therapeutic proteins.

Example 11

Significance of the Results

The results demonstrated above show that antiangiogenic fusion genes are useful as gene therapy and diagnostic reagents, as evidenced by results from studies provided herein. In FIG. 1, the fusion gene could lead to expression of fusion proteins, which were detected by immunoblotting and ELISA. As shown in FIG. 2 and FIG. 3, the fusion proteins are functional and possess both antiangiogenic properties as well as the functions attributable at least in part to the attached proteins. In these functional assays, fusion protein Endostatin-CD, for example, could inhibit angiogenesis to a similar extent of wild type Endostatin, as shown by endothelial tube formation and migration assays. In addition, the therapeutic/diagnostic proteins attached to the exemplary endostatin still functions as in their wild type form. Endostatin-GFP exhibits green fluorescence. Endostatin-GM-CSF could induce proliferation of NSF60 cells, whose growth is GM-CSF dependent. Endostatin-CD could convert non-toxic 5-FC to toxic 5-FU, thereby killing both 293T and HUVEC (human umbilical vascular endothelial cell) cells.

In both in vitro (FIG. 4) and pathological studies (FIG. 5), Endostatin-GFP is shown to be endothelial cell-specific. In FIG. 4, only endothelial cells (SVEC) exhibit GFP signal when incubated with conditional medium containing Endostatin-GFP. In FIG. 5, Endostatin-GFP is able to travel from Endostatin-GFP stable clone tumor (FIG. 5A) to distant parental B16-F10 melanoma cells. Endostatin-GFP is detected by anti-GFP antibody (FIG. 5B). In contrast, when B16-F10 tumor-bearing mice were not inoculated with Endostatin-GFP stable clone tumor, the parental cells did not show GFP signal (FIG. 5C). In other words, the endostatin component of the fusion protein Endostatin-GFP could lead GFP protein to the distant tumor blood vessel sites. Thus, the use of antiangiogenic proteins (endostatin, in this exemplary case) to deliver otherwise non-tumor blood vessel-specific proteins (such as, for example, GFP) to the tumor site is demonstrated. In addition, Endostatin-GFP serves as a diagnostic tool in other embodiments, since fluorescent signal emitted by GFP could be detected, and endostatin could target new blood vessels of tumor.

Lastly, the fusion genes as well as encoded fusion proteins are useful as therapeutic reagents. The inventors have used fusion genes, for example Endostatin-IL12, showing superior anticancer effects than either endostatin or IL12 alone, to treat both melanoma-(FIG. 7A and FIG. 7B) and colon cancer-bearing (FIG. 7C) mice. The fusion proteins encoded by these genes are also effective as protein therapeutic reagents as shown in another animal study (FIG. 8), where tumor cells ex vivo treated with (FIG. 8A and FIG. 5B), or established tumor injected with fusion genes (FIG. 8C), or stable clones (FIG. 8D) served as a "protein factory" and the secreted proteins were able to inhibit distant tumor growth.

Example 12

Ex Vivo Testing of an Angiogenesis Inhibitor Coupled to a Therapeutic or Diagnostic Agent One useful biological property for an anti-cancer therapeutic is its ability to reduce tumorigenicity in vivo. To test the possibly, in some embodiments, anti-tumor activity of an angiogenesis inhibitor coupled to a therapeutic or diagnostic agent not utilized in studies provided herein may be demonstrated. For example, an ex vivo tumorigenicity assay may be performed in a nude mice cancer model. As exemplary cancer cell lines, human breast cancer cell lines MCF-7 and prostate cancer cell line PC-3 may be transfected with a fusion gene delivered by SN liposome in culture plates. Twenty-four hours later, the treated cells may be carefully harvested and inoculated into the mammary fat pads (mfp) (for MCF-7) or subcutaneous connective tissue (for PC-3) of nude mice. For example, four million cells may be inoculated for MCF-7 and one million cells for PC-3. Empty vector pcDNA3-transfected cells can be used as a control. The inoculated tumor size may be measured weekly.

This "ex vivo test" bypasses the gene delivery problems in vivo and shows that under the optimal gene delivery condition, tumor cells with fusion genes with antiangiogenic properties may have less tumor growth ability than controls.

Example 13

In Vivo Testing of Angiogenesis Inhibitor Coupled to a Therapeutic or Diagnostic Agent In some embodiments, an angiogenesis inhibitor coupled to a therapeutic or diagnostic agent, such as an antiangiogenic fusion gene product, described herein or prepared by those of skill in the art based on the teachings provided herein, is used in the following in vivo study. Mice with established tumors are treated with the angiogenesis inhibitor coupled to a therapeutic or diagnostic agent, such as by injection, and shown to provide inhibition of tumor growth in mice compared with proper controls.

A systemic gene therapy approach for breast cancer may be utilized, consisting of, for example, a nonviral gene delivery system (SN) and a fusion gene. The SN-fusion gene may be systemically administered and shown to inhibit the growth and metastasis of, for example, human breast cancer cells implanted in nude mice and, in some embodiments, prolongs the life span of the treated animals.

Obviously, methods disclosed herein have proven useful for specific fusion genes in the context of the invention. Following the teachings provided herein, one of skill in the art can prepare and test any number of fusion genes for anti-angiogenesis activity, anti-cell proliferative activity, antitumor activity, pro-apoptotic activity, or a combination thereof.

Example 14

Testing of Exemplary Angiogenesis Inhibitor Coupled to a Therapeutic or Diagnostic Agent An angiogenesis inhibitor coupled to a therapeutic or diagnostic agent as it relates to anti-tumor activity is tested in an animal study, such as cell lines, cell culture, and/or models in addition to or other than those described in the preceding Examples. In general embodiments of the present invention, fusion genes, for example, are delivered by a vector, such as a liposome, adenoviral vector, or combination thereof, into nude mice models for their anti-tumor activity. Once the anti-tumor activity is demonstrated, potential toxicity is further examined using immunocompetent mice, followed by clinical trials.

In a specific embodiment, the preferential growth inhibitory activity of antiangiogenic fusion genes is tested in at least one animal. Briefly, and for example, cancer cell lines are administered into mammary fat-pad of nude mice to generate a breast xenografted model. Any cancer cell is within the scope of the present invention irrespective of its genotype or expression levels (such as, for example, whether it is HER-2/neu-positive or HER-2/neu-negative). In a specific embodiment, HER-2/neu overexpressing breast cancer cell lines (such as, for example, SKBR3 and/or MDA-MB361) are utilized, such as for testing. After the tumors reach a particular size, the fusion gene and, in some embodiments, the control, is administered into the mouse, such as, for example, intravenously injected in an admixture with an acceptable carrier, such as liposomes. The tumor sizes and survival curve from these treatments are compared and statistically analyzed.

In some embodiments of the present invention, a mouse animal model is utilized to study targeting anti-angiogenic fusion gene products. In one specific embodiment, a bilateral melanoma or colon tumor model is utilized. In another embodiment, a one-sided intratumoral gene therapy protocol is utilized. In another embodiment, wherein a suicide therapeutic gene is utilized in the targeting fusion polypeptide, the model is administered intraperitoneally a prodrug (such as, for example, 5FC) following delivery of the suicide therapeutic gene. In some embodiments, contralateral tumor size is evaluated for a tumor targeting effect. In addition to suicide gene therapy using, for example, endostatin-cytosine deaminase with 5-FC administered as a prodrug, similar approaches are also used for endostatin-IL12. Ipsilateral tumor size may also be evaluated for chemotherapy effect, in some embodiments.

Example 15

Preparation of Additional Angiogenesis Inhibitors Coupled to a Therapeutic or Diagnostic Agent Based on the data in previous Examples and the teachings elsewhere in the specification, in addition to the knowledge in the art, a skilled artisan would be motivated and capable of generating an additional fusion angiogenesis inhibitor coupled to a therapeutic or diagnostic agent and, furthermore, would be able to determine the usefulness in the context of the invention using methodology disclosed herein.

Example 16

Testing of Additional Angiogenesis Inhibitors Coupled to a Therapeutic or Diagnostic Agent Once an angiogenesis inhibitor coupled to a therapeutic or diagnostic agent other than the exemplary embodiments disclosed herein is created, testing using a cell culture in a relevant cell line(s) may be performed, such as described herein. Furthermore, testing of, for example, the antiangiogenic fusion gene products may be performed, such as by using FACS analysis. Also, testing of the additional antiangiogenic fusion gene products using ex vivo systems or in vivo systems as described herein may be employed, in specific embodiments.

Example 17

Clinical Trials

This example is concerned with the development of human treatment protocols using the angiogenesis inhibitor coupled to a therapeutic or diagnostic agents. In specific embodiments, the angiogenesis inhibitor coupled to a therapeutic or diagnostic agent is an antiangiogenic fusion gene product including protein, peptide, or polypeptide or a nucleic acid encoding the antiangiogenic fusion protein, peptide, or polypeptides, alone or in combination with other drugs. In a specific embodiment, the other drugs are also useful for treatment of angiogenesis, such as for tumor inhibition. In a specific embodiment, the drug is useful for treating cancer. The antiangiogenic fusion protein, peptide, or polypeptide or a nucleic acid encoding the antiangiogenic fusion protein, peptide, or polypeptides, and anti-cancer drug treatment will be of use in the clinical treatment of various cancers. Such treatment will be particularly useful tools in anti-tumor therapy, for example, in treating patients with ovarian, breast, prostate, pancreatic, brain, colon, and lung cancers that are resistant to conventional chemotherapeutic regimens.

The various elements of conducting a clinical trial, including patient treatment and monitoring, will be known to those of skill in the art in light of the present disclosure. The following information is being presented as a general guideline for use in establishing the antiangiogenic fusion protein, peptide, or polypeptide or a nucleic acid encoding the antiangiogenic fusion protein, peptide, or polypeptides, in clinical trials.

Patients with advanced, metastatic breast, epithelial ovarian carcinoma, pancreatic, colon, or other cancers chosen for clinical study will typically be at high risk for developing the cancer, will have been treated previously for the cancer which is presently in remission, or will have failed to respond to at least one course of conventional therapy. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile. In regard to the antiangiogenic fusion protein, peptide, or polypeptide or a nucleic acid encoding the antiangiogenic fusion protein, peptide, or polypeptides, and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, PSA, p38 (phosphorylated and un-phosphorylated forms), Akt (phosphorylated and un-phosphorylated forms) and in the cells (antiangiogenic fusion proteins, peptides or polypeptides or nucleic acids encoding the same) may be assessed and recorded.

In the same procedure, the antiangiogenic fusion protein, peptide, or polypeptide or a nucleic acid encoding the antiangiogenic fusion protein, peptide, or polypeptides, may be administered alone or in combination with the other anti-cancer drug. The administration may be in the pleural/peritoneal cavity, directly into the tumor, or in a systemic manner. The starting dose may be 0.5 mg/kg body weight. Three patients may be treated at each dose level in the absence of grade>3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of the antiangiogenic fusion protein, peptide, or polypeptide or a nucleic acid encoding the antiangiogenic fusion protein, peptide, or polypeptides, and the lot of anti-cancer drug exceed 5 EU/kg for any given patient.

The antiangiogenic fusion protein, peptide, or polypeptide or a nucleic acid encoding the antiangiogenic fusion protein, peptide, or polypeptides, and/or the other anti-cancer drug combination, may be administered over a short infusion time or at a steady rate of infusion over a 7 to 21 day period. The antiangiogenic fusion protein, peptide, or polypeptide or a nucleic acid encoding the antiangiogenic fusion protein, peptide, or polypeptides, infusion may be administered alone or in combination with the anti-cancer drug and/or emodin like tyrosine kinase inhibitor. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of the antiangiogenic fusion protein, peptide, or polypeptide or a nucleic acid encoding the mutant protein, peptide, or polypeptides, in combination with an anti-cancer drug will be administered to groups of patients until approximately 60% of patients show unacceptable Grade III or IV toxicity in any category. Doses that are ⅔ of this value could be defined as the safe dose.

Physical examination, tumor measurements, and laboratory tests should, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p38 (phosphorylated and non-phosphorylated forms) and Akt (phosphorylated and non-phosphorylated forms), p185, etc.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, ki67 and Tunel assay to measure apoptosis, Akt) and in the cells (Akt) may be assessed. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Patents

U.S. Pat. No. 4,683,202
U.S. Pat. No. 4,797,368
U.S. Pat. No. 4,879,236
U.S. Pat. No. 5,139,941
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,641,484
U.S. Pat. No. 5,670,488
U.S. Pat. No. 5,789,166
U.S. Pat. No. 5,798,208
U.S. Pat. No. 5,830,650
U.S. Pat. No. 5,871,986
U.S. Pat. No. 5,925,565
U.S. Pat. No. 5,928,906
U.S. Pat. No. 5,935,819
PCT International Application WO 99/16889

Publications

Folkman, Semin. Oncol., 28(6):536-542, 2001.
Brem, Cancer Control, 6(5):436-458, 1999.
Ferrara and Alitalo, Nat. Med., 5(12):1359-1364, 1999.
Keshet and Ben-Sasson, J. Clin. Invest., 104(11):1497-1501, 1999.
Carmeliet and Jain, Nature, 407(6801):249-257, 2000.
Folkman, N. Engl. J. Med., 285(21):1182-1186, 1971.
Kerbel, J. Clin. Oncol., 19(18):45S-51S, 2001.
Risau, Circ. Res., 82(8):926-928, 1998.
Klohs and Hamby, Curr. Opin. Biotechnol., 10(6):544-549, 1999.
Rosen, Oncologist, 5(1):20-27, 2000.
Burke and DeNardo, Crit. Rev. Oncol. Hematol., 39(1-2):155-171, 2001.
Taraboletti and Margosio, Curr. Opin. Pharmacol., 1 (4):378-384, 2001.
Glaspy, Semin. Oncol., 29(7):41-46, 2002.
Boehm, Nature, 390(6658):404-407, 1997.
Thomas et al., J. Clin. Oncol., 21(2):223-231, 2003.
Herbst et al., J. Clin. Oncol., 20(18):3792-3803, 2002.

Eder et al., J. Clin. Oncol., 20(18):3772-3784, 2002.
Beecken Kramer, and Jonas, J. Cell Mol. Med., 4(4):262-269, 2000.
Bouma-ter Steege et al., Crit. Rev. Eukaryot. Gene Expr., 11(4):319-334, 2001.
Cao, Prog. Mol. Subcell. Biol., 20:161-176, 1998.
Cao, Int. J. Biochem. Cell Biol., 33(4):357-369, 2001.
Folkman, Semin. Oncol., 29(6:16):15-18, 2002.
Kirsch et al., Neurooncol., 50(1-2):173-180, 2000.
Ryan and Wilding, Drugs Aging, 17(4):249-255, 2000.
Reed, Nat. Rev. Drug Discov., 1(2):111-121, 2002.
Baliga and Kumar, Hematol. Oncol., 20(2):63-74, 2002.
Chao and Korsmeyer, Annu. Rev. Immunol., 16:395-419, 1998.
Trinchieri, Nat. Rev. Immunol., 3(2):133-146, 2003.
Leonard et al., Blood, 90(7):2541-2548, 1997.
Yang et al., Cancer Biother. Radiopharm., 17(2):233-245, 2002.
Halin et al., Nat. Biotechnol., 20(3):264-269, 2002.
Carnemolla et al., Blood, 99(5):1659-1665, 2002.
Scappaticci et al., Angiogenesis, 4(4):263-268, 2001.
Veenendaal et al., 99(12):7866-7871, 2002.
Arora et al., Cancer Res., 59(1):183-188, 1999.
Hotz et al., J. Gastrointest. Surg., 6(2):159-166, 2002.
Huang et al., Science, 275(5299):547-550, 1997.
Kreitman, Curr. Opin. Immunol., 11 (5):570-578, 1999.
Penichet and Morrison, J. Immunol. Methods, 248(1-2): 91-101, 2001.
Lode et al., Proc. Natl. Acad. Sci. USA, 96(4):1591-1596, 1999.
Ruehlmann et al., Cancer Res., 61 (23):8498-8503, 2001.
Dreier et al., Bioconjug. Chem., 9(4):482-489, 1998.
Niethammer et al., Cancer Res., 61(16):6178-6184, 2001.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A polypeptide comprising an endostatin polypeptide region linked to a cytosine deaminase polypeptide region.

2. The polypeptide of claim 1, wherein the polypeptide is in a pharmaceutically acceptable carrier.

3. The polypeptide of claim 1, wherein the polypeptide is comprised in a liposome.

4. The polypeptide of claim 1, wherein the polypeptide further comprises a protein transduction domain.

* * * * *

SEQUENCE LISTING

```
<160> NUMBER OF SEQ ID NOS: 42

<210> SEQ ID NO 1
<211> LENGTH: 1606
<212> TYPE: DNA
<213> ORGANISM: Herpes Simplex Virus

<400> SEQUENCE: 1
aggagcttca gggagtggcg cagctgcttc atcccgtgg cccgttgctc gcgtttgctg      60
gcggtgtccc cggaagaaat atatttgcat gtctttagtt ctatgatgac acaaaccccg    120
cccagcgtct tgtcattggc gaattcgaac acgcagatgc agtcggggcg gcgcggtccc    180
aggtccactt cgcatattaa ggtgacgcgt gtggcctcga acaccgagcg accctgcagc    240
gacccgctta acagcgtcaa cagcgtgccg cagatcttgg tggcgtgaaa ctcccgcacc    300
tctttggcaa gcgccttgta gaagcgcgta tggcttcgta ccctgccat caacacgcgt     360 ctgcgttcga ccaggctgcg cgttctcgcg gccatagcaa ccgacgtacg gcgttgcgcc    420
ctcgccggca gcaagaagcc acggaagtcc gcctggagta gaaaatgccc acgctactgc    480
gggtttatat agacggtcct cacgggatgg ggaaaaccac caccacgcaa ctgctggtgg    540
ccctgggttc gcgcgacgat atcgtctacg tacccgagcc gatgacttac tggcaggtgc    600 tggggcttc cgagacaatc gcgaacatct acaccacaca acaccgcctc gaccagggtg     660
agatatcggc cggggacgcg gcggtggtaa tgacaagcgc ccagataaca atgggcatgc    720
cttatgccgt gaccgacgcc gttctggctc ctcatatcgg gggggaggct gggagctcac    780
atgccccgcc cccggccctc accctcatct tcgaccgcca tcccatcgcc gccctcctgt    840
gctaccccgg cacgcgatac cttatgggca gcatgacccc ccaggccgtg ctggcgttcg    900
tggccctcat cccgccgacc ttgcccggca caaacatcgt gttggggcc cttccggagg     960 acagacacat cgaccgcctg gccaaacgcc agcgccccgg cgagcggctt gacctggcta   1020
tgttggccgc gattcgcgc gtttacgggc tgcttgccaa tacggtgcgg tatctgcagg   1080
```

-continued

```
gcggcgggtc gtggcgggag gattggggac agctttcggg gacggccgtg ccgccccagg    1140
gtgccgagcc ccagagcaac gcgggcccac gacccatat cggggacacg ttatttaccc     1200
tgtttcgggc ccccgagttg ctggcccca acggcgacct gtataacgtg tttgcctggg     1260
ccttggacgt cttggccaaa cgcctccgtc ccatgcacgt ctttatcctg gattacgacc    1320
aatcgcccgc cggctgccgg gacgccctgc tgcaacttac ctccgggatg gtccagaccc    1380
acgtcaccac cccaggctcc ataccgacga tctgcgacct ggcgcgcatg tttgcccggg    1440
agatggggga ggctaactga aacacggaag gagacaatac cggaaggaac ccgcgctatg    1500
acggaaataa aaagacagaa taaaacgcac gggtgttggg tcgtttgttc ataaacgcgg    1560
ggttcggtcc cagggctggc actctgtcga taccccaccg agaccc                   1606
```

<210> SEQ ID NO 2
<211> LENGTH: 1659
<212> TYPE: DNA
<213> ORGANISM: Herpes Simplex Virus

<400> SEQUENCE: 2

```
ctgcagcagc ttcagggagt ggcgcagctg cttcatgccc gtggtccgct gttcgcgttt     60
gctggccgtg tccccggaag aaatcgattt gcatgtcttt agctccagga tgacgcacac    120
acctcccaac gttttgtcat tggcgaattc gaacacgcag atgcagtctg gcggcgcgg    180 cccgaggtcc acttcgcata ttaaggtgac gcgcgtggcc tcgaacagcg agcgaccctg    240
cagcgacccg ctcatcagcg tcagagcgtt ccacaaatcc tggtggcgtt gaactcccgc    300
acctctcggg cgaacgcctt gtagaagcgg gtatggcttc tcacgccggc caacagcacg    360
cgcctgcgtt cggtcaggct gctcgtgcga gcgggcctac cgacggccgc gcggcgtccc    420
gtcctagcca tcgccagggg gcctccgaag cccgcgggga tccggagctg cccacgctgc    480
tgcgggttta tatagacgga ccccacgggg tggggaagac caccacctcc gcgcagctga    540
tggaggccct ggggccgcgc gacaatatcg tctacgtccc cgagccgatg acttactggc    600
aggtgctggg ggcctccgag accctgacga acatctacaa cacgcagcac cgtctggacc    660
gcggcgagat atcggccggg gaggcggcgg tggtaatgac cagcgcccag ataacaatga    720
gcacgcctta tgcggcgacg gacgccgttt tggctcctca tatcgggggg gaggctgtgg    780
gcccgcaagc cccgccccg ccctcaccc ttgttttcga ccggcaccct atcgcctccc     840
tgctgtgcta cccggccgcg cggtacctca tgggaagcat gaccccccag gccgtgttgg    900
cgttcgtggc cctcatgccc ccgaccgcgc ccggcacgaa cctggtcctg ggtgtccttc    960
cggaggccga acacgccgac cgcctggcca gacgccaaca cccgggcgag cggcttgacc   1020
tggccatgct gtccgccatt cgccgtgtct acgatctact cgccaacacg gtgcggtacc   1080
tgcagcgcgg cggaggtgg cgggaggact ggggccggct gacggggtc gccgcggcga    1140 ccccgcgccc cgaccccgag gacggcgcgg ggtctctgcc ccgcatcgag gacacgctgt    1200
ttgccctgtt ccgcgttccc gagctgctgg ccccaacgg ggacttgtac cacattttg     1260 cctgggtctt ggacgtcttg gccgaccgcc tccttccgat gcatctattt gtcctggatt    1320
acgatcagtc gcccgtcggg tgtcgagacg ccctgttgcg cctcaccgcc gggatgatcc    1380
caacccgcgt cacaaccgcc gggtccatcg ccagatacg cgacctggcg cgcacgtttg    1440
cccgcgaggt ggggggagtt tagttcaaac acggaagccc gaacggaagg cctcccggcg    1500 atgacgcgcaa taaagaaca gaataaaagg cattgttgtc gtgtggtgtg tccataagcg    1560 cggggggttcg gggccagggc tggcaccgta tcagcacccc accgaaaaac ggagcgggcc   1620
```

```
gatccgacct tgttttcggc tctgtactcc ttgtgcttt                            1659

<210> SEQ ID NO 3
<211> LENGTH: 1524
<212> TYPE: DNA
<213> ORGANISM: Varicella zoster
<220> FEATURE:
<221> NAME/KEY: modified_base
<222> LOCATION: (1199)
<223> OTHER INFORMATION: n = a, c, g, t/u

<400> SEQUENCE: 3
ctggcgcata ccctcgcaaa actggtgata cttagtaggg gtatgtatat tagcgctaaa      60
acggcaagat tttaattcca ctataaaaca aacggtcttt ccggcaccac tggattccgt     120
ttgtataata caaacacaat cggggcgtcg gcgtcccaaa tttacttcaa acgacattga     180
tatgcgtaca gcccttttgaa catccacgtg ggataacggc gacaggagtt ttgccagcct    240
cgggttgaac gcgtccgcga aacctcgacg tacgttatca atatccttt tgagtacatc     300 gtaaaaacga gtgtggcaac gttgtcccaa acgaaaacac ttggcccgaa ttcgactagc    360
ggacatattt gaagttccgt cccagaagat aacctaagac gcgtttgtct acaataaaca    420
tgtcaacgga taaaaccgat gtaaaaatgg gcgttttgcg tatttatttg gacggggcgt    480
atggaattgg aaaaacaacc gccgccgaag aatttttaca ccactttgca ataacaccaa    540
accggatctt actcattggg gagcccctgt cgtattggcg taaccttgca ggggaggacg    600
ctatttgcgg aatttacgga acacaaactc gccgtcttaa tggagacgtt tcgcctgaag    660
acgcacaacg cctcacggct cattttcaga gcctgttctg ttctccgcat gcaattatgc    720
atgcgaaaat ctcggcattg atggacacaa gtacatcgga tctcgtacaa gtaaataagg    780
agccgtataa aattatgtta tccgaccgac acccaatcgc ctcaactata tgttttccct    840
tgtccagata cttagtggga gatatgtccc cagcggcgct tcctgggtta ttgtttacgc    900
ttcccgctga accccccggg accaacttgg tagtttgtac cgtttcactc cccagtcatt    960
tatccagagt aagcaaacgg gccagaccgg gagaaacggt taatctgccg tttgttatgg   1020
ttctgagaaa tgtatatata atgcttatta atacaattat atttcttaaa actaacaact   1080
ggcacgcggg ctggaacaca ctgtcatttt gtaatgatgt atttaaacag aaattacaaa   1140
aatccgagtg tataaaacta cgcgaagtac ctgggattga agacacgtta ttcgccgtnc   1200
ttaaacttcc ggagctttgc ggagagtttg gaaatattct gccgttatgg gcatggggaa   1260
tggagaccct ttcaaactgc ttacgaagca tgtctccgtt cgtattatcg ttagaacaga   1320
caccccagca tgcggcacaa gaactaaaaa ctctgctacc ccagatgacc ccggcaaaca   1380
tgtcctccgg tgcatggaat atattgaaag agcttgttaa tgccgttcag gacaacactt   1440
cctaaatata cctagtattt acgtatgtac cagtaaaaag atgatacaca ttgtcatact   1500
cgcgtgtacg tgtttttctt tttt                                          1524

<210> SEQ ID NO 4
<211> LENGTH: 1634
<212> TYPE: DNA
<213> ORGANISM: Escherichia coli

<400> SEQUENCE: 4
ctgcaggcca ctggttaccg ggaattgttc cggtcaacgc ggtattaggt ggcgcgctga      60
gctatctgat ccttaacccg attttgaatc gtaaaacgac agcagcaatg acgcatgtgg     120
aggctaacag tgtcgaataa cgctttacaa acaattatta acgcccggtt accaggcgaa     180
```

```
gaggggctgt ggcagattca tctgcaggac ggaaaaatca gcgccattga tgcgcaatcc      240
ggcgtgatgc ccataactga aaacagcctg gatgccgaac aaggtttagt tataccgccg      300
tttgtggagc cacatattca cctggacacc acgcaaaccg ccggacaacc gaactggaat      360
cagtccggca cgctgtttga aggcattgaa cgctgggccg agcgcaaagc gttattaacc      420
catgacgatg tgaaacaacg cgcatggcaa acgctgaaat ggcagattgc caacggcatt      480
cagcatgtgc gtacccatgt cgatgtttcg gatgcaacgc taactgcgct gaaagcaatg      540
ctggaagtga agcaggaagt cgcgccgtgg attgatctgc aaatcgtcgc cttccctcag      600
gaagggattt tgtcgtatcc caacggtgaa gcgttgctgg aagaggcgtt acgcttaggg      660
gcagatgtag tgggggcgat tccgcatttt gaatttaccc gtgaatacgg cgtggagtcg      720
ctgcataaaa ccttcgccct ggcgcaaaaa tacgaccgtc tcatcgacgt tcactgtgat      780
gagatcgatg acgagcagtc gcgctttgtc gaaaccgttg ctgccctggc gcaccatgaa      840
ggcatgggcg cgcgagtcac cgccagccac accacggcaa tgcactccta taacggggcg      900 tataccctcac gcctgttccg cttgctgaaa atgtccggta ttaactttgt cgccaacccg      960
ctggtcaata ttcatctgca aggacgtttc gatacgtatc caaaacgtcg cggcatcacg     1020
cgcgttaaag agatgctgga gtccggcatt aacgtctgct tggtcacga tgatgtcttc     1080 gatccgtggt atccgctggg aacggcgaat atgctgcaag tgctgcatat ggggctgcat     1140
gtttgccagt tgatgggcta cggcagatt aacgatggcc tgaatttaat cacccaccac     1200
agcgcaagga cgttgaattt gcaggattac ggcattgccg ccggaaacag cgccaacctg     1260
attatcctgc cggctgaaaa tgggtttgat gcgctgcgcc gtcaggttcc ggtacgttat     1320
tcggtacgtg gcggcaaggt gattgccagc acacaaccgg cacaaaccac cgtatatctg     1380
gagcagccag aagccatcga ttacaaacgt tgaacgactg ggttacagcg agcttagttt     1440
atgccggatg cggcgtgaac gccttatccg gcctacgtag agcactgaac tcgtaggcct     1500
gataagcgta gcgcatcagg caattccagc cgctgatctg tgtcagcggc taccgtgatt     1560
cattcccgcc aacaaccgcg cattcctcca acgccatgtg caaaaatgcc ttcgcagcgg     1620
ctgtctgcca gctg                                                       1634

<210> SEQ ID NO 5
<211> LENGTH: 2457
<212> TYPE: DNA
<213> ORGANISM: Mus musculus

<400> SEQUENCE: 5
cgcgcggtgt gtgatctggt cggtaccgag gagcgcaggt tgtgtcacca acatgggga       60 ctctcacgaa gacaccagtg ccacagtgcc tgaggcagtg gctgaagaag tgtctctatt      120
cagcacaacg gacattgttc tgttttctct catcgtgggg gtcctgacct actggttcat      180
ctttaaaaag aagaaagaag agataccgga gttcagcaag atccagacaa cggccccacc      240
tgtcaaagag agcagcttcg tggaaaagat gaagaaaacg ggaaggaaca ttattgtatt      300
ctatggctcc cagacgggaa ccgcggagga gtttgccaac cggctgtcca aggatgccca      360
ccgctatggg atgcggggca tgtctgcaga ccctgaagag tatgacttgg ccgacctgag      420
cagcctgcct gagatcgaca agtccctggt agtcttctgc atggcacat acggagaagg      480 cgaccccacc gacaacgcgc aggacttcta tgattggctg caggagactg acgtggacct      540
cacgggtgtc aagtttgctg tgtttggtct cgggaacaag acctatgagc acttcaacgc      600
catgggcaag tatgtggacc agcggctgga gcagcttggc gcccagcgaa tctttgagtt      660
```

-continued

```
gggccttggt gatgacgacg ggaacttgga agaggatttc atcacatgga gggagcagtt      720
ctggccagct gtgtgcgagt tcttcggggt ggaagccact ggggaggagt cgagcatccg      780
ccagtacgag ctcgtggtcc acgaagacat ggacacagcc aaggtgtaca cgggtgagat      840
gggccgtctg aagagctacg agaaccagaa accccccttc gatgccaaga atccattcct      900
ggctgctgtc accacgaacc ggaagctgaa ccaaggcact gagaggcatc taatgcacct      960
ggaattggac atctcagact ccaagatcag gtatgaatct ggagatcacg tggctgtgta     1020
cccagccaac gactccaccc tggtcaacca gattggggag atcctggggg ctgacctgga     1080
tgtcatcatg tctctaaaca atctcgatga ggagtcgaat aagaagcatc cgttcccctg     1140
ccccaccacc taccgcacgg ccctcaccta ctacctggac atcactaacc cgccacgaac     1200
caacgtgctc tacgagctgg cccagtacgc ctcagagccc tcggagcagg aacacctgca     1260
caagatggcg tcctcctccg gcgagggcaa ggagctgtac ctgagctggg tggtggaggc     1320
ccggaggcac atcctagcca ttctccaaga ctacccgtcc ctgcggccac ccatcgacca     1380
cctgtgcgag ctcctcccga ggctgcaggc ccgctactat tccattgcct cgtcgtctaa     1440
ggtccacccc aactccgtgc acatctgcgc cgtggctgtg gagtatgaag cgaagtctgg     1500
acgagtgaac aaggggtgg ccaccagctg gcttcggacc aaggaaccag caggagagaa      1560
tggccgccgg gccctggtcc ccatgttcgt ccgcaagtcc cagttccgct gcctttcaa      1620 gcccaccaca cctgttatca tggtgggccc cggcactggg gttgcccctt catgggctt      1680 catccaggag cgggccttgg cttcgagagca aggcaaggag gtcggagaga cgctgctcta     1740
ctacggctgc cggcgctcgg atgaggacta tctgtaccgc gaggagctgg cgcgcttcca     1800
caaggacggc gccctcacgc agcttaatgt ggccttttcc cgtgagcagg cccacaaggt     1860
ctatgttcag cacctgctca agagggacaa agagcacctg tggaagctga tccacgaagg     1920
tggtgcccac atctatgtct gcggggatgc tcgaaatatg gccaaagatg tgcagaacac     1980
attctatgac atcgtggccg agtttgggcc catggagcac acccaggctg tggactatgt     2040
taagaagctc atgaccaagg gccgctactc gctggatgta tggagctagg agctgccgcc     2100
ccccacccct cgctccctgt aatcacgtcc ttaacttcct tctgccgacc tccacctctg     2160
gtggttcctg ccctgcctgg acacaggag gcccagggac tgactcctgg cctgagtgat      2220
gccctcctgg gcccttaggc agagcctggt ccattgtacc aggcagccta gcccagccca     2280
gggcacatgg caagagggac tggacccacc tttgggtgat gggtgcctta ggtccccagc     2340
agctgtacag aaggggctct tctctccaca gagctggggt gcagccccaa catgtgattt     2400
tgaatgagtg taaataattt taaataacct ggcccttgga ataaagttgt tttctgt       2457
```

<210> SEQ ID NO 6
<211> LENGTH: 2048
<212> TYPE: DNA
<213> ORGANISM: Pseudomonas

<400> SEQUENCE: 6

```
atcatggatc cacgcactga aggcgcgcgg caagacgcgc ggcgtggcga cgctgtgcat       60
cggcgggggc gaaggcaccg cagtggcact cgaattgcta taagaaccat ggctggggac      120
gcccgacaac aggcgtccac cagctttttt cattccgaca acccgaacga acaatgcgta      180
gagcaggaga ttccatgcgc ccatccatcc accgcacagc catcgccgcc gtgctggcca      240
ccgccttcgt ggcgggcacc gccctggccc agaagcgcga caacgtgctg ttccaggcag      300
ctaccgacga gcagccggcc gtgatcaaga cgctggagaa gctggtcaac atcgagaccg      360
```

-continued

| | |
|---|---|
| gcaccggtga cgccgagggc atcgccgctg cgggcaactt cctcgaggcc gagctcaaga | 420 |
| acctcggctt cacggtcacg cgaagcaagt cggccggcct ggtggtgggc gacaacatcg | 480 |
| tgggcaagat caagggccgc ggcggcaaga acctgctgct gatgtcgcac atggacaccg | 540 |
| tctacctcaa gggcattctc gcgaaggccc cgttccgcgt cgaaggcgac aaggcctacg | 600 |
| gcccgggcat cgccgacgac aagggcggca acgcggtcat cctgcacacg ctcaagctgc | 660 |
| tgaaggaata cggcgtgcgc gactacggca ccatcaccgt gctgttcaac accgacgagg | 720 |
| aaaagggttc cttcggctcg cgcgacctga tccaggaaga agccaagctg gccgactacg | 780 |
| tgctctcctt cgagcccacc agcgcaggcg acgaaaaact ctcgctgggc acctcgggca | 840 |
| tcgcctacgt gcaggtcaac atcaccggca aggcctcgca tgccggcgcc gcgcccgagc | 900 |
| tgggcgtgaa cgcgctggtc gaggcttccg acctcgtgct gcgcacgatg aacatcgacg | 960 |
| acaaggcgaa gaacctgcgc ttcaactgga ccatcgccaa ggccggcaac gtctcgaaca | 1020 |
| tcatccccgc cagcgccacg ctgaacgccg acgtgcgcta cgcgcgcaac gaggacttcg | 1080 |
| acgccgccat gaagacgctg gaagagcgcg cgcagcagaa gaagctgccc gaggccgacg | 1140 |
| tgaaggtgat cgtcacgcgc ggccgccgg ccttcaatgc cggcgaaggc ggcaagaagc | 1200 |
| tggtcgacaa gcggtggcc tactacaagg aagccggcgg cacgctgggc gtggaagagc | 1260 |
| gcaccggcgg cggcaccgac gcggcctacg ccgcgctctc aggcaagcca gtgatcgaga | 1320 |
| gcctgggcct gccgggcttc ggctaccaca gcgacaaggc cgagtacgtg gacatcagcg | 1380 |
| cgattccgcg ccgcctgtac atggctgcgc gcctgatcat ggatctgggc gccggcaagt | 1440 |
| gaatgctgcc cccgggcttt tcactcgcgt tgctcgtgta actccacccc ccgaggggga | 1500 |
| ggcgcggtcc gccttggggc ggccggcgg cgaccgcctc gtcacataga aggaactgcc | 1560 |
| atgttgttga cagcagacca ggaagccatc cgcgacgcgg tgcgcgactt ctcgcaagcc | 1620 |
| gaactctggc ccaacgccgc gaatggggac cgcgagcaca gctttcccaa gagcccacca | 1680 |
| ggccgtcggc tggcgtacgc agtctgcgtg cccgaggagc atggcggcgc cggcctcgac | 1740 |
| tacctcacct cgcgctggtg ctggaggaga tcgcggccgg cgacggcggc accagcaccg | 1800 |
| ccatcagcgt gaccaactgc cccgtcaacg ccatcctcat gcgctacggc aacgcgcagc | 1860 |
| agaagaagca gtggctcgag ccgctggcgc agggccggat gctcggcgcc ttctgcctga | 1920 |
| ccgagccgca ggccggcagc gatgcatcga gcctgcgcac cacggcgcgc aaggacggcg | 1980 |
| acggctacgt gatcgacggc gtgaagcagt tcatcaccag cggcaagaac ggccaggtgg | 2040 |
| cgggatcc | 2048 |

<210> SEQ ID NO 7
<211> LENGTH: 2191
<212> TYPE: DNA
<213> ORGANISM: Homo sapiens

<400> SEQUENCE: 7

| | |
|---|---|
| ggtggccgag cggggaccg ggaagcatgg cccgggggtc ggcggttgcc tgggcggcgc | 60 |
| tcgggccgtt gttgtggggc tgcgcgctgg ggctgcaggg cgggatgctg tacccccagg | 120 |
| agagcccgtc gcgggagtgc aaggagctgg acggcctctg gagcttccgc gccgacttct | 180 |
| ctgacaaccg acgccgggc ttcgaggagc agtggtaccg gcggccgctg tgggagtcag | 240 |
| gccccaccgt ggacatgcca gttccctcca gcttcaatga catcagccag gactggcgtc | 300 |
| tgcggcattt tgtcggctgg gtgtggtacg aacgggaggt gatcctgccg gagcgatgga | 360 |
| cccaggacct gcgcacaaga gtggtgctga ggattggcag tgcccattcc tatgccatcg | 420 |

-continued

```
tgtgggtgaa tggggtcgac acgctagagc atgagggggg ctacctcccc ttcgaggccg    480
acatcagcaa cctggtccag gtggggcccc tgccctcccg gctccgaatc actatcgcca    540
tcaacaacac actcaccccc accaccctgc caccagggac catccaatac ctgactgaca    600
cctccaagta tcccaagggt tactttgtcc agaacacata ttttgacttt ttcaactacg    660
ctggactgca gcggtctgta cttctgtaca cgacacccac cacctacatc gatgacatca    720
ccgtcaccac cagcgtggag caagacagtg ggctggtgaa ttaccagatc tctgtcaagg    780
gcagtaacct gttcaagttg gaagtgcgtc ttttggatgc agaaaacaaa gtcgtggcga    840
atgggactgg gacccagggc caacttaagg tgccaggtgt cagcctctgg tggccgtacc    900
tgatgcacga acgccctgcc tatctgtatt cattggaggt gcagctgact gcacagacgt    960
cactggggcc tgtgtctgac ttctacacac tccctgtggg gatccgcact gtggctgtca   1020
ccaagagcca gttcctcatc aatgggaaac ctttctattt ccacggtgtc aacaagcatg   1080
aggatgcgga catccgaggg aagggcttcg actggccgct gctggtgaag gacttcaacc   1140
tgcttcgctg gcttggtgcc aacgctttcc gtaccagcca ctacccctat gcagaggaag   1200
tgatgcagat gtgtgaccgc tatgggattg tggtcatcga tgagtgtccc ggcgtgggcc   1260
tggcgctgcc gcagttcttc aacaacgttt ctctgcatca ccacatgcag gtgatggaag   1320
aagtggtgcg tagggacaag aaccaccccg cggtcgtgat gtggtctgtg gccaacgagc   1380
ctgcgtccca cctagaatct gctggctact acttgaagat ggtgatcgct cacaccaaat   1440
ccttggaccc ctcccggcct gtgacctttg tgagcaactc taactatgca gcagacaagg   1500
gggctccgta tgtggatgtg atctgtttga acagctacta ctcttggtat cacgactacg   1560
ggcacctgga gttgattcag ctgcagctgg ccacccagtt tgagaactgg tataagaagt   1620
atcagaagcc cattattcag agcgagtatg gagcagaaac gattgcaggg tttcaccagg   1680
atccacctct gatgttcact gaagagtacc agaaaagtct gctagagcag taccatctgg   1740
gtctggatca aaaacgcaga aaatatgtgg ttggagagct catttggaat tttgccgatt   1800
tcatgactga acagtcaccg acgagagtgc tggggaataa aaaggggatc ttcactcggc   1860
agagacaacc aaaaagtgca gcgttccttt tgcgagagag atactggaag attgccaatg   1920
aaaccaggta tccccactca gtagccaagt cacaatgttt ggaaaacagc ccgtttactt   1980
gagcaagact gataccacct gcgtgtccct tcctccccga gtcagggcga cttccacagc   2040
agcagaacaa gtgcctcctg gactgttcac ggcagaccag aacgtttctg gcctgggttt   2100
tgtggtcatc tattctagca gggaacacta aaggtggaaa taaaagattt tctattatgg   2160
aaataaagag ttggcatgaa agtcgctact g                                  2191
```

<210> SEQ ID NO 8
<211> LENGTH: 1616
<212> TYPE: DNA
<213> ORGANISM: Bacillus sphaericus

<400> SEQUENCE: 8

```
tttaaaaata ctacttcata gtatagaaat aatagtaacg ccaaaaaatg acggtgtatg     60
tggcgcgatg tggcgttatt gcatgggatt ggaaatttca gtcttaaaaa aaggtgtatg    120
accgccaaaa aacggcgtaa atttatcctt gaatttccat taatggaagt gatagtatgg    180
ttttggaagc ggaataaatc tatttttagt taattatggt actcgtgata agtgaagtaa    240
attctttatt atgaagatac gttagttgat ttaaaaataa ttccgttaca ttttttttaaa    300
atactttttc aagggagtgt tttttatgtt aggttgcagt agcttatcaa ttcgtacaac    360
```

```
agatgataaa agtttattcg ctcgcacaat ggatttttaca atggaaccag atagtaaagt    420
gattattgtc ccacgtaatt acggcattcg attgttagaa aaagaaaatg tagtcattaa    480
caattcatat gcttttgttg gaatgggaag cactgacatt acatcaccag ttctctatga    540
tggggtaaac gaaaagggat taatgggcgc aatgctttac tatgctacat tgcgactta     600 tgctgacgaa cctaaaaaag gcacaacagg catcaatccc gtgtatgtaa tttctcaagt    660
tttaggaaat tgtgtaactg tcgatgatgt tattgaaaaa ttaacttctt atacattatt    720
gaatgaggcc aatataatac ttggctttgc acccccactt cactatacat ttacagatgc    780
ttctggtgaa tcgattgtta ttgaaccgga taaaacaggc attaccattc atcgaaaaac    840
gattggcgtc atgacgaata gccctggcta tgaatggcat cagacaaatt taagagctta    900
cattggtgtc acaccaaatc cgccacaaga tataatgatg ggagacttgg atttgacacc    960
gtttgggcaa ggggcagggg gcttaggatt accaggtgat tttacgccgt cagcacgttt   1020
tcttcgggta gcatactgga aaaatatac tgaaaaagcc aaaaatgaaa cagaaggcgt   1080
aacaaacttg ttccatattc tatcttctgt aaatatccca aaaggtgttg ttttgacaaa   1140
tgaggggaaa acggattata ccatctatac ctcagctatg tgtgcacaaa gtaaaaacta   1200
ttactttaaa ctgtatgaca atagtcgaat ttcagccgtt tccttaatgg ctgaaaattt   1260
aaatagtcaa gatttaatta catttgagtg ggatcgtaaa caagatatta agcaattaaa   1320
tcaagtaaat gtaatgagct aaaaattgcc tattatatag tacaaggtat taaaaaatgc   1380
ccccgattgt tagatatatg aacaatcggg ggctcttttt cgatagtaaa atacacaaag   1440
tcattagaat taaaaagatt tgtggaatgt taatatattg ttagaaatta tttcactgta   1500
aagataggaa agtatccgaa aaagctcatt gtggttgtga ggattgccaa cttttcgcta   1560
agcaaattct atatgcaagt ccacaagttt tggatttctt tagcagaggt ctgcag        1616

<210> SEQ ID NO 9
<211> LENGTH: 2409
<212> TYPE: DNA
<213> ORGANISM: Bacillus megaterium

<400> SEQUENCE: 9
atgaagatga agtggctaat atcagtcata atcctatttg ttttcatttt tcctcaaaat      60 ctagttttg ctggggagga taagaatgaa ggggtcaaag tagtacgtga taattttgga   120
gtaccccatt tatacgctaa aaataaaaaa gatttatatg aagcgtatgg atatgttatg   180
gcaaaggatc gactatttca gttggagatg ttccgtcgcg gaaatgaggg gaccgtttca   240 gaaattttg gagaggatta tctttcaaaa gatgagcaat ccagaagaga tggatatagt   300
aataaagaaa ttaaaaaaat gattgacggt ctggatcgtc agccaaaaga attaatagca   360
aaatttgctg aagtatttc acgttatgta aatgaagctt taaagatcc agatgataaa   420 ctttcgaagg agtttcatga atatcagttt ttaccgcaaa atggacttc aacagatgtt   480 gtccgtgttt atatggtatc catgacgtat tttatggata atcaccagga gttaaaaaac   540
gcagagatac ttgcaaagct agaacatgaa tatgggacag aagtttcccg gaaaatgttt   600
gatgatttag tgtggaaaaa tgatcctagc gctcctacaa gcattgtaag cgaggggaaa   660
ccaaaagggg aatcgtcatc tcaatccctt caaaaactgt cttcagctgt aatcaaagct   720
tctgaaaaag ttggaaagga aagggagaat tttgtccaat cgtctgaaga acttggatta   780
ccgttaaaga taggcagtaa tgccgccata gtcggttccg agaaatccgc aacaggaaat   840
gctttattat tcagtggacc acaagtaggt tttgttgctc ctggattttt gtacgaggta   900
```

```
ggtttgcatg cgccaggttt cgatatggaa ggttcaggtt tcataggcta tcctttcatc    960
atgttcggag ccaacaatca ctttgctcta agtgcgacag ctgggtacgg aaatgtaacc   1020
gatatctttg aggaaaaatt gaatacgaaa aactcttccc agtatttata caaagggaag   1080
tggagagaca tggaaaagag gaaggaatct ttcacggtca aaggagacaa tggtgaaaag   1140
aaaacagtag aaaagattta ttatcgaaca gtacatggtc ctgtaattag tagagatgaa   1200
acaaataaag tggcttacag taagtcgtgg tctttccgtg gaactgaggc ccaaagcatg   1260
tcggcttaca tgaaagcgaa ttgggcaaaa aacttaaaag aatttgagaa tgcagctagt   1320
gaatatacga tgtctttgaa ttggtattat gcggataaga aaggtgatat agcgtattat   1380
catgtaggaa gatatccagt tagaaacaac aaaattgatg aaagaatccc tacaccagga   1440
acaggagaat atgagtggaa aggttttatt ccttttaaag agaaccctca tgtaatcaat   1500
ccgaagaatg gctatgtagt taattggaac aataagcctt ctaaagagtg gtaaatggt    1560 gaatatagtt attattgggg tgaggataat cgagtccaac aatatatcaa tgggatggaa   1620
gcgagaggga agttacatt agaagatatt aatgaaatta attatacggc aagctttgca    1680
cagcttcgag caaacctctt taaaccgtta ttaattgatg tgttggacaa gaataaatca   1740
accaacggga actacgccta tttaattgaa aaactggaag aatggaataa tctaaaagaa   1800
gacgaaaata aagatggata ttatgatgca gggattgcgg cattctttga tgaatggtgg   1860
aataatctcc atgataaact ctttatggat gaattgggag acttctatgg aataacgaaa   1920
gaaattaccg atcatcgtta tggggcttca ttagcatata aaatattaag caaggaatct   1980
acaaactata atgggtgaa cgtagaccag gaaaaaataa taatgaaaag cacaaatgaa    2040
gtacttgcta aattgcaatc agaaaaaggg ttaaaagcag aaaaatggcg tatgcctata   2100
aaaacgatga cttttggtga aaaatcattg attggtattc cccacgggta tggctcaatg   2160
actccaatta ttgaaatgaa tcgtggaagt gaaaatcatt atattgaaat gactccgaaa   2220
gggccgagtg gctttaacat cacaccacct ggtcaaattg gatttgtaaa aaaagatgga   2280
acgataagtg accactatga tgaccaacta gttatgttcg ccgaatggaa attcaagcca   2340
tacttattta caagaaaga tatttataaa tcagctaaaa atgtaagcgc attaaatatg    2400
agtaagtag                                                            2409
```

<210> SEQ ID NO 10
<211> LENGTH: 876
<212> TYPE: DNA
<213> ORGANISM: Escherichia coli

<400> SEQUENCE: 10

```
atggtgacaa agagagtgca acggatgatg ttcgcggcgg cggcgtgcat tccgctgctg     60
ctgggcagcg cgccgcttta tgcgcagacg agtgcggtgc agcaaaagct ggcggcgctg    120
gagaaaagca gcgagggcg gctgggcgtc gcgctcatcg ataccgcaga taatacgcag    180
gtgctttatc gcggtgatga acgctttcca atgtgcagta ccagtaaagt tatgcggcc    240 gcggcggtgc ttaagcagag tgaaacgcaa aagcagctgc ttaatcagcc tgtcgagatc    300
aagcctgccg atctggttaa ctacaatccg attgccgaaa acacgtcaa cggcacaatg    360 acgctggcag agctgagcgc ggccgcgttg cagtacagcg acaataccgc catgaacaaa    420
ttgattgccc agctcggtgg cccgggaggc gtgacggctt tgcccgcgc gatcggcgat    480 gagacgtttc gtctggatcg cactgaacct acgctgaata ccgccattcc cggcgacccg    540
agagacacca ccacgccgcg ggcgatggca cagacgttgc gtcagcttac gctgggtcat    600
```

```
gcgctgggcg aaacccagcg ggcgcagttg gtgacgtggc tcaaaggcaa tacgaccggc      660
gcagccagca ttcgggccgg cttaccgacg tcgtggactg caggtgataa gaccggcagc      720
ggcggctacg gcaccaccaa tgatattgcg cgtgatctgg cgcagggtcg tgcgccgctg      780
gttctggtga cctattttac ccagccgcaa cagaacgcag agagccgccg cgatgtgctg      840
gcttcagcgg cgagaatcat cgccgaaggg ctgtaa                                876
```

<210> SEQ ID NO 11
<211> LENGTH: 1167
<212> TYPE: DNA
<213> ORGANISM: Escherichia coli

<400> SEQUENCE: 11

```
tcgcgatctg atcaacgatt cgtggaatct ggtggttgat ggtctggcta acgcgatca       60 aaaaagagtg cgtccaggct aaagcggaaa tctatagcgc attttttctcg cttaccattt    120 ctcgttgaac cttgtaatct gctggcacgc aaaattactt tcacatggag tctttatgga    180
tatcatttct gtcgccttaa agcgtcattc cactaaggca tttgatgcca gcaaaaaact    240
taccccggaa caggccgagc agatcaaaac gctactgcaa tacagcccat ccagcaccaa    300
ctcccagccg tggcatttta ttgttgccag cacggaagaa ggtaaagcgc gtgttgccaa    360
atccgctgcc ggtaattacg tgttcaacga gcgtaaaatg cttgatgcct cgcacgtcgt    420
ggtgttctgt gcaaaaaccg cgatggacga tgtctggctg aagctggttg ttgaccagga    480
agatgccgat ggccgctttg ccacgccgga agcgaaagcc gcgaacgata aggtcgcaa     540 gttcttcgct gatatgcacc gtaaagatct gcatgatgat gcagagtgga tggcaaaaca    600
ggtttatctc aacgtcggta acttcctgct cggcgtggcg gctctgggtc tggacgcggt    660
acccatcgaa ggttttgacg ccgccatcct cgatgcagaa tttggtctga agagaaagg    720 ctacaccagt ctggtggttg ttccggtagg tcatcacagc gttgaagatt ttaacgctac    780
gctgccgaaa tctcgtctgc cgcaaaacat caccttaacc gaagtgtaat tctctcttgc    840
cgggcatctg cccggctatt tcctctcaga ttctcctgat ttgcataacc ctgtttcagc    900
cgtcatcata ggctgctgtt gtataaagga gcgttatgc aggatttaat atcccaggtt    960
gaagatttag cgggtattga gatcgatcac accacctcga tggtgatgat tttcggtatt   1020 attttctga ccgccgtcgt ggtgcatatt attttgcatt gggtggtact gcggaccttc   1080 gaaaacgtg ccatcgccag ttcacggctt tggttgcaaa tcattaccca gaataaactc   1140
ttccaccgtt tagcttttac cctgcag                                        1167
```

<210> SEQ ID NO 12
<211> LENGTH: 1622
<212> TYPE: DNA
<213> ORGANISM: Homo sapiens

<400> SEQUENCE: 12

```
atgaggctca tcctgcctgt gggtttgatt gctaccactc ttgcaattgc tcctgtccgc       60
tttgacaggg agaaggtgtt ccgcgtgaag ccccaggatg aaaaacaagc agacatcata     120
aaggacttgg ccaaaaccaa tgagcttgac ttctggtatc aggtgccac ccaccacgta      180 gctgctaata tgatggtgga tttccgagtt agtgagaagg aatcccaagc catccagtct     240
gccttggatc aaaataaaat gcactatgaa atcttgattc atgatctaca agaagagatt     300
gagaaacagt ttgatgttaa agaagatatc ccaggcaggc acagctacgc aaaatacaat     360
aattgggaaa agattgtggc ttggactgaa aagatgatgg ataagtatcc tgaaatggtc     420
```

```
tctcgtatta aaattggatc tactgttgaa gataatccac tatatgttct gaagattggg      480
gaaaagaatg aaagaagaaa ggctattttt atggattgtg gcattcacgc acgagaatgg      540
gtctccccag cattctgcca gtggtttgtc tatcaggcaa ccaaaactta tgggagaaac      600
aaaattatga ccaaactctt ggaccgaatg aatttttaca ttcttcctgt gttcaatgtt      660
gatggatata tttggtcatg gacaaagaac cgcatgtgga gaaaaaatcg ttccaagaac      720
caaaactcca aatgcatcgg cactgacctc aacaggaatt ttaatgcttc atggaactcc      780
attcctaaca ccaatgaccc atgtgcagat aactatcggg gctctgcacc agagtccgag      840
aaagagacga agctgtcac taatttcatt agaagccacc tgaatgaaat caaggtttac       900
atcaccttcc attcctactc ccagatgcta ttgtttccct atggatatac atcaaaactg      960
ccacctaacc atgaggactt ggccaaagtt gcaagattg gcactgatgt tctatcaact      1020
cgatatgaaa cccgctacat ctatggccca atagaatcaa caatttaccc gatatcaggt     1080
tcttctttag actgggctta tgacctgggc atcaaacaca catttgcctt tgagctccga     1140
gataaaggca aatttggttt ctccttcca gaatcccgga taaagccaac gtgcagagag      1200
accatgctag ctgtcaaatt tattgccaag tatatcctca agcatacttc ctaaagaact     1260
gccctctgtt tggaataagc caattaatcc tttttgtgc ctttcatcag aaagtcaatc     1320
ttcagttatc cccaaatgca gcttctattt cacctgaatc cttctcttgc tcatttaagt     1380
cccatgttac tgctgtttgc ttttacttac tttcagtagc accataacga agtagcttta     1440
agtgaaacct tttaactacc tttctttgct ccaagtgaag tttggaccca gcagaaagca     1500
ttattttgaa aggtgatata cagtggggca cagaaaacaa atgaaaaccc tcagtttctc     1560
acagattttc accatgtggc ttcatcaatt tatgtgctaa acaataaaaa taaaatgcac     1620
tt                                                                    1622

<210> SEQ ID NO 13
<211> LENGTH: 1705
<212> TYPE: DNA
<213> ORGANISM: Manihot esculenta

<400> SEQUENCE: 13
acaactttct tcagctatca gggatgctcg tcttgttcat aagcttgttg gctctcacta       60
ggccagcaat gggaactgat gatgatgatg ataatattcc tgacgatttt agccgtaaat      120
attttccaga tgacttcatt tttggaacgg ctacttctgc ttatcagatc gaaggtgaag      180
caaccgcaaa gggtagagca cctagtgttt gggacatatt ttccaaggag actccagata      240
gaatattaga tggcagcaat ggagacgttg cagttgattt ctataaccgc tacatacaag      300
atataaaaaa cgtcaaaaag atgggtttta atgcatttag aatgtccatt tcatggtcta      360
gagttatacc atccggaagg agacgtgaag gagtgaacga ggaaggaatt caattctaca      420
atgatgttat caatgaaatt ataagcaatg gactagagcc ttttgttact attttttcatt     480 gggatactcc tcaagcactg caggacaaat atggtggctt cttaagccgt gatattgtgt      540
acgattatct ccaatatgca gatcttctct ttgaaagatt cggtgatcga gtgaaaccgt      600
ggatgacttt taatgaacca tcagcatatg ttggatttgc ccatgatgat ggagttttg      660 cccctggtcg atgctcatct tgggtgaatc gccaatgcct agctggagac tcagccacag      720
aaccttatat agttgcccat aatttgcttc tttctcatgc tgcagctgtt caccaatata      780
gaaaatatta tcagggaact caaaagggca agattgggat taccctcttt accttctggt      840
atgaacctct ctccgacagt aaagttgatg tgcaagcagc caaaacagcc ttagatttca      900
```

| | |
|---|---|
| tgtttggatt gtggatggat cccatgactt atggacgata tccaagaact atggtagatt | 960 |
| tagccggaga taaattgatt ggatttacag atgaagaatc tcaattactt aggggatcat | 1020 |
| atgattttgt tggattacaa tactacactg catattatgc agaaccaatt cctccagttg | 1080 |
| atccaaaatt tcgtagatac aaaactgata gtggtgttaa tgcgactcct tacgatctta | 1140 |
| atggtaatct tattggtcca caggcttact cgtcatggtt ttacattttt ccaaaaggta | 1200 |
| ttcgacactt tttgaactat accaaagata catataatga tccagtcatt tacgttactg | 1260 |
| agaatggggt tgacaactac aataatgaat ctcaaccaat tgaagaggca cttcaagatg | 1320 |
| atttcaggat ttcgtactat aaaaagcata tgtggaatgc actaggatct ctcaagaact | 1380 |
| acggtgttaa actcaaaggt tattttgcat ggtcatattt agacaacttc gaatggaata | 1440 |
| ttggttatac atcaagattt gggttgtact atgtagacta caaaaataac ctaacaaggt | 1500 |
| atcccaagaa atcggctcat tggttcacaa aattcctgaa tatatcggtt aatgcaaata | 1560 |
| atatctatga gcttacatca aaggattcaa ggaaggttgg caaattctat gtgatgtaga | 1620 |
| ttatgtctgg atgttttgtg tgtatctcat aattaaataa tatcgttggg caattatgaa | 1680 |
| gctccaatga tctagcatat gttgt | 1705 |

<210> SEQ ID NO 14
<211> LENGTH: 1057
<212> TYPE: DNA
<213> ORGANISM: Escherichia coli

<400> SEQUENCE: 14

| | |
|---|---|
| agcttggaca caagacaggc ttgcgagata tgtttgagaa taccacttta tcccgcgtca | 60 |
| gggagaggca gtgcgtaaaa agacgcggac tcatgtgaaa tactggtttt tagtgcgcca | 120 |
| gatctctata atctcgcgca acctattttc ccctcgaaca cttttttaagc cgtagataaa | 180 |
| caggctggga cacttcacat gagcgaaaaa tacatcgtca cctgggacat gttgcagatc | 240 |
| catgcacgta aactcgcaag ccgactgatg ccttctgaac aatggaaagg cattattgcc | 300 |
| gtaagccgtg gcggtctggt accgggtgcg ttactggcgc gtgaactggg tattcgtcat | 360 |
| gtcgataccg tttgtatttc cagctacgat cacgacaacc agcgcgagct taaagtgctg | 420 |
| aaacgcgcag aaggcgatgg cgaaggcttc atcgttattg atgacctggt ggataccggt | 480 |
| ggtactgcgg ttgcgattcg tgaaatgtat ccaaaagcgc actttgtcac catcttcgca | 540 |
| aaaccggctg tcgtccgct ggttgatgac tatgttgttg atatcccgca agatacctgg | 600 |
| attgaacagc cgtgggatat gggcgtcgta ttcgtcccgc caatctccgg tcgctaatct | 660 |
| tttcaacgcc tggcactgcc gggcgttgtt cttttttaact tcaggcgggt tacaatagtt | 720 |
| tccagtaagt attctggagg ctgcatccat gacacaggca aacctgagcg aaaccctgtt | 780 |
| caaaccccgc tttaaacatc ctgaaaacctc gacgctagtc cgccgcttta atcacggcgc | 840 |
| acaaccgcct gtgcagtcgg cccttgatgg taaaaccatc cctcactggt atcgcatgat | 900 |
| taaccgtctg atgtggatct ggcgcggcat tgacccacgc gaaatcctcg acgtccaggc | 960 |
| acgtattgtg atgagcgatg ccgaacgtac cgacgatgat ttatacgata cggtgattgg | 1020 |
| ctaccgtggc ggcaactgga tttatgagtg ggccccg | 1057 |

<210> SEQ ID NO 15
<211> LENGTH: 1718
<212> TYPE: DNA
<213> ORGANISM: Escherichia coli

<400> SEQUENCE: 15

```
gaatcagacg ggccgatatt ggcgtgcata aaggcgtctg gcagggttct gtcgaggtaa      60
cgccagaaac gttttattcg aacatcgatc tcgtcttgtg ttagaattct aacatacggt     120
tgcaacaacg catccagttg ccccaggtag accggcatcg atgtgaccga cggtacgtgg     180
tggtaaagaa tggtcagcag agagagtgcg tcatcaagat ctttcgcgcc ttccagctcc     240
agccattcgg aaccgttcgc cagaaaacgg gcgtaatcgg gtaagacata gcgcggtttg     300
tacggcgcat gaccttcaaa catatcgcag attacacctt catccaagcg cgcggcgggc     360
ttcggcagga agctgtgggt aaggcagatt gttttctgct tccagtgcca gaaaatggcg     420
cttctgctcc gggctaagca ctgggctggt gacaatttgc tggcaacgtt gttgcagtgc     480
attttcatga gaagtgggca tcttcttttc cttttatgcc gaaggtgatg cgccattgta     540
agaagtttcg tgatgttcac tttgatcctg atgcgtttgc caccactgac gcattcattt     600
gaaagtgaat tatttgaacc agatcgcatt acagtgatgc aaacttgtaa gtagatttcc     660
ttaattgtga tgtgtatcga agtgtgttgc ggagtagatg ttagaatact aacaaactcg     720
caaggtgaat tttattggcg acaagccagg agaatgaaat gactgatctg aaagcaagca     780
gcctgcgtgc actgaaattg atggacctga acaccctgaa tgacgacgac accgacgaga     840
aagtgatcgc cctgtgtcat caggccaaaa ctccggtcgg caataccgcc gctatctgta     900
tctatcctcg ctttatcccg attgctcgca aaactctgaa agagcagggc accccggaaa     960
tccgtatcgc tacggtaacc aacttcccac acggtaacga cgacatcgac atcgcgctgg    1020
cagaaacccg tgcggcaatc gcctacggtg ctgatgaagt tgacgttgtg ttcccgtacc    1080
gcgcgctgat ggcgggtaac gagcaggttg gttttgacct ggtgaaagcc tgtaaagagg    1140
cttgcgcggc agcgaatgta ctgctgaaag tgatcatcga aaccggcgaa ctgaaagacg    1200
aagcgctgat ccgtaaagcg tctgaaatct ccatcaaagc gggtgcggac ttcatcaaaa    1260
cctctaccgg taaagtggct gtgaacgcga cgccggaaag cgccgcgcatc atgatggaag    1320 tgatccgtga tatgggcgta gaaaaaaccg ttggtttcaa accggcgggc ggcgtgcgta    1380
ctgcggaaga tgcgcagaaa tatctcgcca ttgcagatga actgttcggt gctgactggg    1440
cagatgcgcg tcactaccgc tttggcgctt ccagcctgct ggcaagcctg ctgaaagcgc    1500
tgggtcacgg cgacggtaag agcgccagca gctactaagt aagatgcttt acgcctgatg    1560
cgctgcgctt atcaggccta cgagacgtat ctacccgtag gccggataag gcgtagacgc    1620
atccggcaaa agccgcctca tactctttttc ctcgggaggt taccttgttt ctcgcacaag    1680
aaattattcg taaaaaacgt gatggtcatg cgctgagc                             1718
```

<210> SEQ ID NO 16
<211> LENGTH: 2521
<212> TYPE: DNA
<213> ORGANISM: Homo sapiens

<400> SEQUENCE: 16

```
ggcacgagcc accgtccagg gagcaggtag ctgctgggct ccggggacac tttgcgttcg      60
ggctgggagc gtgctttcca cgacggtgac acgcttccct ggattggcag ccagactgcc     120
ttccgggtca ctgccatgga gggagccgcag tcagatccta gcgtcgagcc ccctctgagt     180
caggaaacat tttcagacct atggaaacta cttcctgaaa acaacgttct gtcccccttg     240
ccgtcccaag caatggatga tttgatgctg tccccggacg atattgaaca atggttcact     300
gaagacccag gtccagatga agctcccaga atgccagagg ctgctccccg cgtggcccct     360
gcaccagcag ctcctacacc ggcggcccct gcaccagccc cctcctggcc cctgtcatct     420
```

```
tctgtccctt cccagaaaac ctaccagggc agctacggtt tccgtctggg cttcttgcat    480
tctgggacag ccaagtctgt gacttgcacg tactccoctg ccctcaacaa gatgttttgc    540
caactggcca agacctgccc tgtgcagctg tgggttgatt ccacaccccc gcccggcacc    600
cgcgtccgcg ccatggccat ctacaagcag tcacagcaca tgacggaggt tgtgaggcgc    660
tgcccccacc atgagcgctg ctcagatagc gatggtctgg ccctcctca gcatcttatc      720 cgagtggaag gaaatttgcg tgtggagtat ttggatgaca gaaacacttt tcgacatagt    780
gtggtggtgc cctatgagcc gcctgaggtt ggctctgact gtaccaccat ccactacaac    840
tacatgtgta acagttcctg catgggcggc atgaaccgga ggcccatcct caccatcatc    900
acactggaag actccagtgg taatctactg ggacggaaca gctttgaggt gcgtgtttgt    960
gcctgtcctg ggagagaccg cgcacagag gaagagaatc tccgcaagaa aggggagcct    1020
caccacgagc tgcccccagg gagcactaag cgagcactgc caacaacac cagctcctct    1080 ccccagccaa agaagaaacc actggatgga gaatatttca cccttcagat ccgtgggcgt    1140
gagcgcttcg agatgttccg agagctgaat gaggccttgg aactcaagga tgcccaggct    1200
gggaaggagc caggggggag cagggctcac tccagccacc tgaagtccaa aaagggtcag    1260
tctacctccc gccataaaaa actcatgttc aagacagaag ggcctgactc agactgacat    1320
tctccacttc ttgttcccca ctgacagcct cccaccccca tctctccctc cctgccatt    1380 ttgggttttg ggtctttgaa cccttgcttg caataggtgt gcgtcagaag cacccaggac    1440
ttccatttgc tttgtcccgg ggctccactg aacaagttgg cctgcactgg tgttttgttg    1500
tggggaggag gatggggagt aggacatacc agcttagatt ttaaggtttt tactgtgagg    1560
gatgtttggg agatgtaaga aatgttcttg cagttaaggg ttagtttaca atcagccaca    1620
ttctaggtag gggcccactt caccgtacta accaggaag ctgtccctca ctgttgaatt    1680
ttctctaact tcaaggccca tatctgtgaa atgctggcat ttgcacctac ctcacagagt    1740
gcattgtgag ggttaatgaa ataatgtaca tctggccttg aaaccacctt ttattacatg    1800
gggtctagaa cttgaccccc ttgagggtgc ttgttccctc tccctgttgg tcggtgggtt    1860
ggtagtttct acagttgggc agctggttag gtagagggag ttgtcaagtc tctgctggcc    1920
cagccaaacc ctgtctgacc acctcttggt gaaccttagt acctaaaagg aaatctcacc    1980
ccatcccaca ccctggagga tttcatctct tgtatatgat gatctggatc caccaagact    2040
tgttttatgc tcagggtcaa tttctttttt cttttttttt ttttttttct ttttctttga    2100
gactgggtct cgctttgttg cccaggctgg agtggagtgg cgtgatcttg gcttactgca    2160
gcctttgcct cccggctcg agcagtcctg cctcagcctc cggagtagct gggaccacag    2220
gttcatgcca ccatggccag ccaacttttg catgttttgt agagatgggg tctcacagtg    2280
ttgcccaggc tggtctcaaa ctcctgggct caggcgatcc acctgtctca gcctcccaga    2340
gtgctgggat tacaattgtg agccaccacg tccagctgga agggtcaaca tcttttacat    2400
tctgcaagca catctgcatt ttcaccccac ccttccctc cttctccctt tttatatccc    2460
atttttatat cgatctctta ttttacaata aactttgct gccaaaaaaa aaaaaaaaa    2520 a                                                                    2521
```

<210> SEQ ID NO 17
<211> LENGTH: 4741
<212> TYPE: DNA
<213> ORGANISM: Homo sapiens

<400> SEQUENCE: 17

```
tccggtttt  tctcagggac  gttgaaatta  ttttgtaac   gggagtcggg  agaggacggg    60
gcgtgccccg  acgtgcgcgc  gcgtcgtcct  ccccggcgct  cctccacagc  tcgctggctc   120
ccgccgcgga  aaggcgtcat  gccgcccaaa  acccccgaa   aaacggccgc  caccgccgcc   180
gctgccgccg  cggaacccc   ggcaccgccg  ccgccgcccc  ctcctgagga  ggacccagag   240
caggacagcg  gcccggagga  cctgcctctc  gtcaggcttg  agtttgaaga  aacagaagaa   300
cctgatttta  ctgcattatg  tcagaaatta  aagataccag  atcatgtcag  agagagagct   360
tggttaactt  gggagaaagt  ttcatctgtg  gatggagtat  tgggaggtta  tattcaaaag   420
aaaaaggaac  tgtggggaat  ctgtatcttt  attgcagcag  ttgacctaga  tgagatgtcg   480
ttcacttta   ctgagctaca  gaaaaacata  gaaatcagtg  tccataaatt  ctttaactta   540
ctaaaagaaa  ttgataccag  taccaaagtt  gataatgcta  tgtcaagact  gttgaagaag   600
tatgatgtat  tgtttgcact  cttcagcaaa  ttggaaagga  catgtgaact  tatatatttg   660
acacaaccca  gcagttcgat  atctactgaa  ataaattctg  cattggtgct  aaagtttct   720
tggatcacat  ttttattagc  taaaggggaa  gtattacaaa  tggaagatga  tctggtgatt   780
tcatttcagt  taatgctatg  tgtccttgac  tattttatta  aactctcacc  tcccatgttg   840
ctcaaagaac  catataaaac  agctgttata  cccattaatg  gttcacctcg  aacacccagg   900
cgaggtcaga  acaggagtgc  acggatagca  aaacaactag  aaaatgatac  aagaattat    960
gaagttctct  gtaaagaaca  tgaatgtaat  atagatgagg  tgaaaaatgt  ttatttcaaa  1020
aatttatac   ctttatgaa   ttctcttgga  cttgtaacat  ctaatggact  tccagaggtt  1080
gaaaatcttt  ctaaacgata  cgaagaaatt  tatcttaaaa  ataaagatct  agatgcaaga  1140
ttattttgg   atcatgataa  aactcttcag  actgattcta  tagacagttt  tgaaacacag  1200
agaacaccac  gaaaaagtaa  ccttgatgaa  gaggtgaatg  taattcctcc  acacactcca  1260
gttaggactg  ttatgaacac  tatccaacaa  ttaatgatga  ttttaaattc  agcaagtgat  1320
caaccttcag  aaaatctgat  ttcctatttt  aacaactgca  cagtgaatcc  aaaagaaagt  1380
atactgaaaa  gagtgaagga  tataggatac  atctttaaag  agaaatttgc  taaagctgtg  1440
ggacagggtt  gtgtcgaaat  tggatcacag  cgatacaaac  ttggagttcg  cttgtattac  1500
cgagtaatgg  aatccatgct  taaatcagaa  gaagaacgat  tatccattca  aaattttagc  1560
aaacttctga  atgacaacat  ttttcatatg  tctttattgg  cgtgcgctct  tgaggttgta  1620
atggccacat  atagcagtaa  gtacatctca  gaatcttgat  tctggaacag  atttgtcttt  1680
cccatggatt  ctgaatgtgc  ttaatttaaa  agcctttgat  ttttacaaag  tgatcgaaag  1740
ttttatcaaa  gcagaaggca  acttgacaag  agaaatgata  aaacatttag  aacgatgtga  1800
acatcgaatc  atggaatccc  ttgcatggct  ctcagattca  cctttatttg  atcttattaa  1860
acaatcaaag  gaccgagaag  gaccaactga  tcaccttgaa  tctgcttgtc  ctcttaatct  1920
tcctctccag  aataatcaca  ctgcagcaga  tatgtatctt  tctcctgtaa  gatctccaaa  1980
gaaaaaggt   tcaactacgc  gtgtaaattc  tactgcaaat  gcagagacac  aagcaacctc  2040
agccttccag  acccagaagc  cattgaaatc  tacctctctt  tcactgtttt  ataaaaaagt  2100
gtatcggcta  gcctatctcc  ggctaaatac  actttgtgaa  cgccttctgt  ctgagcaccc  2160
agaattagaa  catatcatct  ggaccctttt  ccagcacacc  ctgcagaatg  agtatgaact  2220
catgagagac  aggcatttgg  accaaattat  gatgtgttcc  atgtatggca  tatgcaaagt  2280
gaagaatata  gaccttaaat  tcaaaatcat  tgtaacagca  tacaaggatc  ttcctcatgc  2340
tgttcaggag  acattcaaac  gtgttttgat  caaagaagag  gagtatgatt  ctattatagt  2400
```

```
attctataac tcggtcttca tgcagagact gaaaacaaat attttgcagt atgcttccac   2460 caggcccccct accttgtcac caatacctca cattcctcga agcccttaca agtttcctag   2520 ttcacccctta cggattcctg agggaacat ctatatttca cccctgaaga gtccatataa   2580
aatttcagaa ggtctgccaa caccaacaaa aatgactcca agatcaagaa tcttagtatc   2640
aattggtgaa tcattcggga cttctgagaa gttccagaaa ataaatcaga tggtatgtaa   2700
cagcgaccgt gtgctcaaaa gaagtgctga aggaagcaac cctcctaaac cactgaaaaa   2760
actacgcttt gatattgaag gatcagatga agcagatgga agtaaacatc tcccaggaga   2820
gtccaaattt cagcagaaac tggcagaaat gacttctact cgaacacgaa tgcaaaagca   2880
gaaaatgaat gatagcatgg ataccctcaaa caaggaagag aaatgaggat ctcaggacct   2940
tggtggacac tgtgtacacc tctggattca ttgtctctca cagatgtgac tgtataactt   3000
tcccaggttc tgtttatggc cacatttaat atcttcagct cttttttgtgg atataaaatg   3060 tgcagatgca attgtttggg tgattcctaa gccacttgaa atgttagtca ttgttattta   3120
tacaagattg aaaatcttgt gtaaatcctg ccatttaaaa agttgtagca gattgtttcc   3180
tcttccaaag taaaattgct gtgctttatg gatagtaaga atggccctag agtgggagtc   3240
ctgataaccc aggcctgtct gactactttg ccttcttttg tagcatatag gtgatgtttg   3300
ctcttgtttt tattaattta tatgtatatt tttttaattt aacatgaaca cccttagaaa   3360
atgtgtccta tctatcttcc aaatgcaatt tgattgactg cccattcacc aaaattatcc   3420
tgaactcttc tgcaaaaatg gatattatta gaaattagaa aaaaattact aattttacac   3480
attagatttt atttactat tggaatctga tatactgtgt gcttgtttta taaaattttg   3540
cttttaatta aataaaagct ggaagcaaag tataaccata tgatactatc atactactga   3600
aacagatttc atacctcaga atgtaaaaga acttactgat tattttcttc atccaactta   3660
tgtttttaaa tgaggattat tgatagtact cttggttttt ataccattca gatcactgaa   3720
tttataaagt acccatctag tacttgaaaa agtaaagtgt tctgccagat cttaggtata   3780
gaggacccta acacagtata tcccaagtgc actttctaat gtttctgggt cctgaagaat   3840
taagatacaa attaatttta ctccataaac agactgttaa ttataggagc cttaattttt   3900
ttttcataga gatttgtcta attgcatctc aaaattattc tgccctcctt aatttgggaa   3960
ggtttgtgtt ttctctggaa tggtacatgt cttccatgta tcttttgaac tggcaattgt   4020
ctatttatct tttatttttt taagtcagta tggtctaaca ctggcatgtt caaagccaca   4080
ttatttctag tccaaaatta caagtaatca agggtcatta tgggttaggc attaatgttt   4140
ctatctgatt ttgtgcaaaa gcttcaaatt aaaacagctg cattagaaaa agaggcgctt   4200
ctcccctccc ctacacctaa aggtgtattt aaactatctt gtgtgattaa cttatttaga   4260
gatgctgtaa cttaaaatag gggatattta aggtagcttc agctagcttt taggaaaatc   4320
actttgtcta actcagaatt attttaaaa agaaatctgg tcttgttaga aaacaaaatt   4380 ttatttgtg ctcatttaag tttcaaactt actattttga cagttatttt gataacaatg   4440
acactagaaa acttgactcc atttcatcat tgttctgca tgaatatcat acaaatcagt   4500 tagttttag gtcaagggct tactatttct gggtcttttg ctactaagtt cacattagaa   4560
ttagtgccag aattttagga acttcagaga tcgtgtattg agatttctta aataatgctt   4620
cagatattat tgctttattg cttttttgta ttggttaaaa ctgtacattt aaaattgcta   4680
tgttactatt ttctacaatt aatagtttgt ctatttaaa ataaattagt tgttaagagt   4740
c                                                                    4741
```

<210> SEQ ID NO 18
<211> LENGTH: 809
<212> TYPE: DNA
<213> ORGANISM: Homo sapiens

<400> SEQUENCE: 18

```
agcggcgagg gctggatcct gggccaaata tatgccaaca acgacaagct ctccaagagg      60
ctgaagaaag tgtggaagcc acagctgttt gagcgagagt tctacagtga gatcctggac     120
aagaagttca cagtgactgt gaccatgcgg accctggacc tcatcgatga ggcttacggg     180
ctcgactttt acatcctcaa gaccccgaag gaggacctgt gctccaagtt tgggatggag     240
ctgaagcgag gatgctgct gcggcttgcc cggcaggacc cccagctgca ccccgaggac      300
cccgagcggc gggcagccat ctacgacaag tacaaggaat ttgccatccc agaggaggag     360
gcagagtggg tgggcctcac gctggaggag gccattgaga agcagagact tttggaggag     420
aaggaccctg taccctgtt caagatctat gtggcggagc tgatccagca gctgcagcag      480
caggcactgt cagagccggc ggtggtgcag aagacagcca gtggccagtg accacacagc     540
tcctccatgc ctgaccaaca gcccagcttt ccctgccag gcctttgca ctgaggacac       600
agatcccggg gagctgtgag gccaccggt gggcagtggg tggatcctgg tttcgtgtgc      660
tgcccatgca ccttccagcc cggggccagc ttggcaggga tccccaggag gcctgggccg     720
cccagaggct cctctcaggc tgggccccga cgtttgcggc agtgttcctt gtcccgtggg     780
gccgggagcg agtaaagtct gggccaggc                                        809
```

<210> SEQ ID NO 19
<211> LENGTH: 340
<212> TYPE: DNA
<213> ORGANISM: Homo sapiens

<400> SEQUENCE: 19

```
gaagaaagag gagggggctgg ctggtcacca gagggtgggg cggaccgcgt gcgctcggcg    60
gctgcggaga gggggagagc aggcagcggg cggcggggag cagcatggag ccggcggcgg    120
ggagcagcat ggagccttcg gctgactggc tggccacggc cgcggcccgg ggtcgggtag    180
aggaggtgcg ggcgctgctg gaggcggggg cgctgcccaa cgcaccgaat agttacggtc    240
ggaggccgat ccaggtgggt agagggtctg cagcgggagc aggggatggc gggcgactct    300
ggaggacgaa gtttgcaggg gaattggaat caggtagcgc                           340
```

<210> SEQ ID NO 20
<211> LENGTH: 585
<212> TYPE: DNA
<213> ORGANISM: Homo sapiens

<400> SEQUENCE: 20

```
ggaaattgga aactggaagc aaatgtaggg gtaattagac acctgggct tgtgtggggg      60
tctgcttggc ggtgaggggg ctctacacaa gcttcctttc cgtcatgccg gcccccaccc    120
tggctctgac cattctgttc tctctggcag gtcatgatga tgggcagcgc ccgagtggcg    180
gagctgctgc tgctccacgg cgcggagccc aactgcgccg accccgccac tctcacccga    240
cccgtgcacg acgctgcccg ggagggcttc ctggacacgc tggtggtgct gcaccgggcc    300
ggggcgcggc tggacgtgcg cgatgcctgg ggcgtctgc ccgtggacct ggctgaggag     360
ctgggccatc gcgatgtcgc acggtacctg cgcgcggctg cgggggggcac cagaggcagt    420
aaccatgccc gcatagatgc cgcggaaggt ccctcaggtg aggactgatg atctgagaat    480
```

```
ttgtaccctg agagcttcca aagctcagag cattcatttt ccagcacaga aagttcagcc    540
cgggagacca gtctccggtc ttgcctcagc tcacgcgcca atcgg                    585

<210> SEQ ID NO 21
<211> LENGTH: 422
<212> TYPE: DNA
<213> ORGANISM: Homo sapiens

<400> SEQUENCE: 21
ccccggtcgc gctttctctg ccctccgccc gggtggacct ggagcgcttg agcggtcggc     60
gcgcctggag cagccaggcg ggcagtggac tagctgctgg accagggagg tgtgggagag    120
cggtggcggc gggtacatgc acgtgaagcc attgcgagaa ctttatccat aagtatttca    180
atgccggtag ggacggcaag agaggagggc gggatgtgcc acacatcttt gacctcaggt    240
ttctaacgcc tgttttcttt ctgccctctg cagacatccc cgattgaaag aaccagagag    300
gctctgagaa acctcgggaa acttagatca tcagtcaccg aaggtcctac agggccacaa    360
ctgcccccgc cacaacccac cccgctttcg tagttttcat ttagaaaata gagcttttaa    420
aa                                                                   422

<210> SEQ ID NO 22
<211> LENGTH: 10907
<212> TYPE: DNA
<213> ORGANISM: Homo sapiens

<400> SEQUENCE: 22
tgagcagcct gagatgtcag taattgtagc tgctccaagc ctgggttctg ttttttagtg     60
ggatttctgt tcagatgaac aatccatcct ctgcaatttt ttaaaagcaa aactgcaaat    120
gtttcaggca cagaaaggag gcaaaggtga agtccagggg aggtcagggg tgtgaggtag    180
atgggagcgg atagacacat cactcatttc tgtgtctgtc agaagaacca gtagacactt    240
ccagaattgt cctttattta tgtcatctcc ataaccatc tgcaaatgag ggttatttgg    300
catttttgtc attttggagc cacagaaata aaggatgaca agcagagagc cccgggcagg    360
aggcaaaagt cctgtgttcc aactatagtc atttctttgc tgcatgatct gagttaggtc    420
accagacttc tctgagcccc agtttcccca gcagtgtata cgggctatgt ggggagtatt    480
caggagacag acaactcact cgtcaaatcc tccccttcct ggccaacaaa gctgctgcaa    540
ccacagggat ttcttctgtt caggtgagtg tagggtgtag ggagattggt tcaatgtcca    600
attcttctgt ttccctggag atcaggttgc ccttttttgg tagtctctcc aattccctcc    660
ttcccggaag catgtgacaa tcaacaactt tgtatactta agttcagtgg acctcaattt    720
cctcatctgt gaaataaacg ggactgaaaa atcattctgg cctcaagatg ctttgtttggg    780 gtgtctaggt gctccaggtg cttctggag aggtgaccta gtgagggatc agtgggaata    840
gaggtgatat tgtgggcctt ttctggaaat tgcagagagg tgcatcgttt ttataattta    900 tgaatttta tgtattaatg tcatcctcct gatcttttca gctgcattgg gtaaatcctt    960
gcctgccaga gtgggtcagc ggtgagccag aaaggggct cattctaaca gtgctgtgtc    1020
ctcctggaga gtgccaactc attctccaag taaaaaaagc cagatttgtg gctcacttcg    1080
tggggaaatg tgtccagcgc accaacgcag gcgagggact gggggaggag ggaagtgccc    1140
tcctgcagca cgcgaggttc cggaccggc tggcctgctg gaactcggcc aggctcagct    1200
ggctcggcgc tgggcagcca ggagcctggg ccccggggag ggcggtcccg ggcggcgcgg    1260
tgggccgagc gcgggtcccg cctccttgag gcgggcccgg gcgggcggt tgtatatcag    1320
```

```
ggccgcgctg agctgcgcca gctgaggtgt gagcagctgc cgaagtcagt tccttgtgga    1380
gccggagctg ggcgcggatt cgccgaggca ccgaggcact cagaggaggt gagagagcgg    1440
cggcagacaa caggggaccc cgggccggcg gcccagagcc gagccaagcg tgcccgcgtg    1500
tgtccctgcg tgtccgcgag gatgcgtgtt cgcgggtgtg tgctgcgttc acaggtgttt    1560
ctgcggcagg tgaatgacgg gcgtgggtcg gtgcgcgctc ggcttgcgca cacggtgtct    1620
ctataagtgc gcgggtgacg agagtcggga tgtgccggag accccggggc ggagagcggg    1680
attacaagta caggaatccc tggtcacgct ccccgcccct ggaaacccag ctggggcgag    1740
ggagggcgtg gacgggaccg ttctgggagc tcgcctttgg ctgcggttgg ctccaggccc    1800
caggcgcagt ttgctcgcgg cgtggggatg aagtccgtgt ccctggaggg gcccaggaag    1860
ggcgaggaaa gcggagtgga gtaagttcgt ctaggatcgg tcccgggtgg ctctgggatc    1920
caatctgcgc cgcccctggcc caggtccag gttcaggtcc tttacgccac tgtgtccacc    1980
acctggctga cgctgaggt cagcgcgggc tgtttcctgg cccttgggaa tgtgccagga    2040
cccgtcccct aaggactagc gaggaggtga ctcactgtga caaggagacc ccagggaacg    2100
gactgtatga ggtcagaacc ccgcccggga tggggtacag cgggactcca gaagccctct    2160
cccctgcccc ttcgcggtct ccgtcctccc atcggcacag tgacctattt ggctggaaca    2220
gtttgttccc aaggaagccg ggcactggag gtccgggaca ccgcgtcggg tccccgctcc    2280
gcggcgcgct gtaggggtcg gggagtcacg gccctgcgct gggcgggctc taaccagcct    2340
gtcagtcggg gaagggcaag ggtctcctct acctctttcc caccgcggcc gggagaatcg    2400
cggcccagcc tgtcctcggg tcggggcgct ggactccggg gcgggagcgg agcccacgcc    2460
tggatgggag gcggggaggg ttcatgtctt tgaggggtgg ggggtctggg gggcacgacg    2520
ctgctcaggg cctctatcag ctgcctcggg ggctcagggc ttcccgacct agcccagatt    2580
ccctctccga aagctacagg gctgagcgga gcagggggg gagtcgcccc ctggggcgcc    2640
gccgcctggc gcggaccaca gcgcgtcctc tccgtcccaa accctgggg gacacttgcg    2700 ccctcttcgt gaggaaaagc atcttggagc tgggttagga acttggggcg cccaggcagc    2760
ttcccctctc cttgcctccc tccacgtcgc gtttctggga ggacttgcga gcggttttgt    2820
tttcgttgct cccgtctatt tttattttcc agggatctga ctcatcccgt gctttgggcg    2880
tggagataag gtggagggc cggctccgg cgcgcgcgcg cgtgcgtgtc tgcgcgggcg    2940
tgtgtgtgtg tgtgtgtgtg tgtgtgtgtg tgtgtgtctg tgtcagagac ggcacaagag    3000
cgcgcggttt cccaacagcg gcgggagttt cggaagcctg gccggctcag cgtgacgtgt    3060
tcgcggcccc ccgtcccct cccattctcc ccctccccac cccagggtga cgcgcagccg    3120
gagtggaagc agagttttgg cgggcgagca gcgccttgca ggaaactgac tcatcactac    3180
tccctccagc ggtccgaggc tctgcccacg cacctcccac tccgcgcgtg atttcctgga    3240
ggccggcgcc ccctcccggc cctggcggga atagcacaca ggctttcccg cggagtgggg    3300
ctggccggcg cgaaccgccg cggctactcc tgggctcatc cgagatcaac ccctatgcca    3360
ttaccacccc ttcaaaggag cactcctag gttcaacagt attcactgag ctcttactgg    3420
aaattaaaat atggctgaag tctaaggcag gaaggccaat aaaggaggct atttttaatt    3480
gtttctaaaa caagggtttg cgtttctgag ttttctttgg gctgaaagtt attatgagca    3540
tgagagcaga ttttgatggg ggaggagagg cctatgagag ccataagaga aggaggggtg    3600
gtagaagagg agagggtgcc tgcctagatc ctagtcctgt cttgaactcc cgagagccag    3660
ggaatatcca gctccttgat gaagccctag gcgggcgcct cctccttgtg cctatgatgt    3720
```

```
attgagaccc agaatgtcca tttcaaacat accagtgtgt ctccgcttgg ctggcacccc    3780
aagagtgccc atctgaggaa ttgtgccaaa cacttgcttg aatcttcaat ttggattaag    3840
ttggtctcgg gaggcagggc ctcagcaatc tatattttga aaaaactccc taggtgcttt    3900
tctttctttc tttctttctt tctttctttc tttctttctt tctttctttc tttctttctt    3960
tcttctttt tctttctttc tttcttttc tttcttttct ttctttcttt ctttctttct    4020
ttcttctttt ctttctttct tccttttctct ttctctcttt cttttctttt ctctctttct    4080
ttcttttctt tcgacagagt tgcactctgt cacccaggct ggagtgcaat ggcaccatcc    4140
tggactcaag tagtcctcct gtttcagcct cccaagtaac cgggaccaca ggcgtgatcc    4200
ccccgccccc atgcccagat ttttttttt tttttttttt ttttgagatg cggtctcgct    4260
ctgtcaccca ggctggagtg cagtggcgtg atctcggctc actgcaagct ccgcctcccg    4320
ggttcacgcc attctcctgc ctcagcctcc cgagtagctg ggactacagg tgctgccatc    4380
atgcccggct aattttttt tgtatttta gtagagacgg gggtttcacc gtgttagcca    4440
ggatggtctc aatctcctga cctcgtgctc cgccctcctc ggcctcccaa agtgctggga    4500
ttacaggtgt gagacactgc acccaaccac ccagctaatt tttatttatt tttattttta    4560
gtagagacag ggtctcagct agttgcccag gctagtcttg gacccttggg ctcaaatgat    4620
tctcccacct ctgcctccca gagtattagg attacaggca taagccactg cccctggcct    4680
ccccaagtga ttgtgatggg cctctctggt taagaaacct caaaattaga gagggagtgg    4740
ggttcaatac tacagcacag gactcagggc aaacaggcct gggttcagat cctggctgtg    4800
ccacttatga actgtgtgat gttaggcaag ttacttaact tatctgagcc ttggttgcct    4860
cttctgtaaa aagggagcta atagatatcc actttttagg aggattgata ttttaaact    4920
gcttagaaca gcccccaaac ataaaaatat ataataaat cccaactcat gcctagcaga    4980
gggtggatag aggttatttg agggctctgt ccactgtact gggtgacccc tttatggggc    5040
agtggccttt ggccttttta gctgtatgac tcaggggcaa gtctcatatc tcttccatct    5100
cctgcccttt aaacttggtg tgaagttacc aagagcctcc tctcccaacc agctgggacg    5160
tgaaactgtg ggctccactg atcacaagca gtggggtgag gtggggtgga gcagatgtgg    5220
catgtgtccc gggcttcctg cctcatgagg actcagcaga gctttcaccc ccagaaactg    5280
caagttggga cttgtcccta ggaaaatcca gttgctgcca aggtcgtgca gtcactcagc    5340
cctggagtca agccagagca ggcaggtagg tgccagggct ccctcatggg caaactcact    5400
ctccgttttc cctctcctga agggggagga gaggagccag gtagaccagc cacctttaat    5460
tttctttttg cctgcaaaac ggtttccttg gacacaggca acacgaggca ggggctgcca    5520
ggtgtctaga cttcagatca cctgatgtgc ctggcaggat gtggctcagc ctgggagaaa    5580
tcatcccttg cgctgccccg cccggccccct ccttacccct aggccacccg cctgacgaca    5640
tccttgggaa aggccctcag cctacagcac ctgtcagctg ctgtctgaag gaggtagttg    5700
gcagggggaa gtgataggg ggaggctcag taaaactgaa ggcagagagg aataatcata    5760
cttctgtttt caatgcactt ctctatacga agtgctgctg gcacgttacc tacattaact    5820
cagttaattc tcatgtctat cctctgagac agtcactatt actatcccca ttttatagat    5880
gaggaaacta gagctcagac aagttaagtt gcttgcccag ggtcacctag taaaacctgg    5940
actccagccc aggtgatctg gctccagagc cctcctgctt aaccaccagg atacagcctt    6000
tcattcagct ctgttctgtc tgccttgctg catggactct gtgatcaatt tcttgagtat    6060
gtgtctgtag ccatgctctt taaacttgta catggcccca tttatggatg aggaaactga    6120
```

```
gacctagaga cattaagtgg cttttttaaag cttacgtagt aactggcaga gctaggacca    6180
caacccgggt gcttttttgcc ccaaagtccc gggtactttt acttggcaga gcagggttac    6240
cctacttggg gatctgggtc gggggactta ggaggctgga ggaactgtca gactgtttct    6300
tcttttggga attgaccttc tggccagggc tgcgattagg aaactgctgg actctggcaa    6360
ttcacacata tttgggggc attcacaccc atgaggaca cctctggggg gaaaacaaat      6420
tgattttagc tgataatacc tggtggcaaa caggaccctg gtccttgctc ttgcaataga    6480
cttgcctttg ttgacattag cttgcccttc agttgcctgc tctcccagtg accttggtgt    6540
gccaggctgg ctgagctctg ctggtggggg tcaggcctcc tgtgggaagg aagcaggaag    6600
accagctgga aggagtgaga gagaccctct ggtaggaaga cgtcacctga ggtgacacag    6660
caaagcccgg ccaggtaaca tagtgtctaa tctccgccgt gaccagggcc ttccttgtat    6720
ctctgctgca ggcgccatgt cagaaccggc tggggatgtc cgtcagaacc catgcggcag    6780
caaggcctgc cgccgcctct tcggcccagt ggacagcgag cagctgagcc gcgactgtga    6840
tgcgctaatg gcgggctgca tccaggaggc ccgtgagcga tggaacttcg actttgtcac    6900
cgagacacca ctggagggtg acttcgcctg ggagcgtgtg cggggccttg gcctgcccaa    6960
gctctacctt cccacggggc cccggcgagg ccgggatgag ttgggaggag gcaggcggcc    7020
tggcacctca cctgctctgc tgcaggggac agcagaggaa gaccatgtgg acctgtcact    7080
gtcttgtacc cttgtgcctc gctcagggga gcaggctgaa gggtcccag gtggacctgg     7140 agactctcag ggtcgaaaac ggcggcagac cagcatgaca ggtgcggaca tgtgcacgga    7200
aggactttgt aagggaccag gattctcaga atccatggtc caagggctga cctgtctggt    7260
cctggtccag catgctccag gtagaaggaa acaggcccag agaggggaag caacctccct    7320
gaggtcacac agcaagtagg cagcaaagac caactagcta acatttattg ggaatgttca    7380
ttatgccagg cccttttgcca agcttctaag gtagatttat ttagtcctta tagcaatgtt   7440
ataacataag acattcttgt caccctgccc gcctttcttt ttgagacagg tgtcttaact    7500
ctgttggcca gactggagtg cagtgatacg atcatggctc actgcagctt caaactcctg    7560
ggctcaagcg atcttcctac ctcagcctcc tgggtagctg ggaagctggg actatagttg    7620
tacaccacta cgcccggtta atttttttgag tttttgtaga gacaaggtct caccatgttg    7680
cccgggctgg tcttgaactc ctgagctcaa gcagtcctcc tgcctcagcc tcccaaagtg    7740
ttgtgattac aggcgtgagc caccatgccc agcccttgc catccttta gggcaaggaa       7800 accaggctca gagaggtaga gtgatttatc taaggtctca aagtgaattt gccgttgggt    7860
caagactaat tataataaca acaactactg acgtttatat gggcccggca ttgtgctgaa    7920
cactttcatg gattttgtaa cagaatccct agatcagcac tgtccagtaa ctctgcaggg    7980
atgggagtgt ccggtacagg ggccacgagc cacatacggc tgttgtgcat ttgacacaca    8040
gctcatgtga ctgaggaact gaattgttca ttttatttga ttgtagtctg tttaaacaag    8100
cacacagagc tagtagtggt tcctctgctg ggcagcttga cttagagcag acccatgggt    8160
gcgggtgcgg tgatggataa aatcacatct gtgaagcatg gtgggacact ccataatacc    8220
cctcaagaga cagagtggac gttccccgag ttcttcctgt tctcagcagt cggcccatt     8280 ggccccaggg aagggtgtcc tggccccca ctgtcttcct cagttgggca gctccgccgc     8340
gtcctcttct tcttggcctg gctgacttct gctgtctctc ctcagatttc taccactcca    8400
aacgccggct gatcttctcc aagaggaagc cctaatccgc ccacaggaag cctgcagtcc    8460
tggaagcgcg agggcctcaa aggcccgctc tacatcttct gccttagtct cagtttgtgt    8520
```

```
gtcttaatta ttatttgtgt tttaatttaa acacctcctc atgtacatac cctggccgcc    8580
ccctgccccc cagcctctgg cattagaatt atttaaacaa aaactaggcg gttgaatgag    8640
aggttcctaa gagtgctggg cattttttatt ttatgaaata ctatttaaag cctcctcatc    8700
ccgtgttctc cttttcctct ctcccggagg ttgggtgggc cggcttcatg ccagctactt    8760
cctcctcccc acttgtccgc tgggtggtac cctctggagg ggtgtggctc cttcccatcg    8820
ctgtcacagg cggttatgaa attcacccccc tttcctggac actcagacct gaattctttt    8880
tcatttgaga agtaaacaga tggcactttg aagggcctc accgagtggg ggcatcatca    8940
aaaactttgg agtcccctca cctcctctaa ggttgggcag ggtgaccctg aagtgagcac    9000
agcctagggc tgagctgggg acctggtacc ctcctggctc ttgataccc cctctgtctt     9060 gtgaaggcag ggggaaggtg gggtcctgga gcagaccacc ccgcctgccc tcatggcccc    9120
tctgacctgc actggggagc ccgtctcagt gttgagcctt ttccctcttt ggctccctg     9180 tacctttga ggagccccag ctaccttcct ctccagctg ggctctgcaa ttcccctctg      9240
ctgctgtccc tccccttgt cctttcccctt cagtacccctc tcagctccag gtggctctga   9300
ggtgcctgtc ccaccccccac ccccagctca atggactgga aggggaaggg acacacaaga   9360
agaagggcac cctagttcta cctcaggcag ctcaagcagc daccgccccc tcctctagct    9420
gtgggggtga gggtcccatg tggtggcaca ggccccccttg agtggggtta tctctgtgtt   9480
aggggtatat gatgggggag tagatctttc taggagggag acactggccc ctcaaatcgt    9540
ccagcgacct tcctcatcca ccccatccct ccccagttca ttgcactttg attagcagcg    9600
gaacaaggag tcagacattt taagatggtg gcagtagagg ctatggacag ggcatgccac    9660
gtgggctcat atgggctgg gagtagttgt ctttcctggc actaacgttg agcccctgga     9720
ggcactgaag tgcttagtgt acttggagta ttggggtctg accccaaaca ccttccagct    9780
cctgtaacat actggcctgg actgttttct ctcggctccc catgtgtcct ggttcccgtt    9840
tctccaccta gactgtaaac ctctcgaggg cagggaccac accctgtact gttctgtgtc    9900
tttcacagct cctcccacaa tgctgaatat acagcaggtg ctcaataaat gattcttagt    9960
gactttactt gtaatattac tattgtggtt attatacctt ataagaacaa ataaatgggc   10020
ttttgggaag gatttcataa ttaaataatt ttaaaaatta agcatttaaa tttagagaat   10080
gcagaaaact tagcaaacag aaagactgct gcaaaaaaca acagcaaaac aaaaactact   10140
gtcacacctc tgcaaagatc accaatgtca atattttggt ttgttgtgta atcttttttgt  10200 aaagaatata ttatagctta acatcattat tcatcagata aatgcaaatt aagataccac   10260
aataagatac caccatacac ttaccagaat gattaaaaaa gactgacagt gccaagcatt   10320
ggcaaggtta tggagcaact ggatctctta tttaaaaaaa ctgtttgggc cgggcgcagt   10380
ggctcacacc tagaatccca gtgcttcggg aggctgaggc aggagatcac ttgaggccaa   10440
gggttcaaga ccagcctggc caacatggtg aaatctctac taaaaataca aaaattagct   10500
gggcatggtg gtgcacgctt gtaatcccag ctacttggaa ggctgaggtg ggaggatcac   10560
ttgaacccag gaggcagagg ttgcagtcag ctgagatcat accactgtac tccagcctct   10620
tccagggtga cagtgagatt catctcaaat aaatacataa ataaaaaact gtttggtaat   10680
atcttctaaa gatgcctacc ttcatggcta ccctcatgacc cagtaattct attcctggac   10740
atgttctcga gagaaatgag ttcatatttc cactgaaaaa ggcataagaa tgttctacac   10800
agtggctcac acctataatc ccagcacttt gggaggctaa ggcaggagga cggcttgagc   10860
ccaagagtgt gagaccagtt tgggcaacat agcgagactc ttatctc                 10907
```

<210> SEQ ID NO 23
<211> LENGTH: 756
<212> TYPE: DNA
<213> ORGANISM: Homo sapiens

<400> SEQUENCE: 23

```
gctggaggat gtggctgcag agcctgctgc tcttgggcac tgtggcctgc agcatctctg      60
cacccgcccg ctcgcccagc cccagcacgc agccctggga gcatgtgaat gccatccagg     120
aggcccggcg tctcctgaac ctgagtagag acactgctgc tgagatgaat gaaacagtag     180
aagtcatctc agaaatgttt gacctccagg agccgacctg cctacagacc cgcctggagc     240
tgtacaagca gggcctgcgg ggcagcctca ccaagctcaa gggccccttg accatgatgg     300
ccagccacta caagcagcac tgccctccaa ccccggaaac ttcctgtgca acccagacta     360
tcacctttga aagtttcaaa gagaacctga aggactttct gcttgtcatc ccctttgact     420
gctgggagcc agtccaggag tgagaccggc agatgaggc tggccaagcc ggggagctgc     480
tctctcatga acaagagct agaaactcag gatggtcatc ttggagggac caaggggtgg     540
gccacagcca tggtgggagt ggcctggacc tgccctgggc cacactgacc ctgatacagg     600
catggcagaa gaatgggaat attttatact gacagaaatc agtaatattt atatatttat     660
atttttaaaa tatttattta tttatttatt taagttcata ttccatattt attcaagatg     720
ttttaccgta ataattatta ttaaaaatat gcttct                               756
```

<210> SEQ ID NO 24
<211> LENGTH: 4830
<212> TYPE: DNA
<213> ORGANISM: Homo sapiens

<400> SEQUENCE: 24

```
ccaggcttgt ccctgctacc cccacccagc cttttcctgag gcctcaggcc tgccaccaag      60
cccccagctc cttctccccg cagggaccca aacacaggcc tcaggactca acacagcttt     120
tccctccaac cccgttttct ctccctcaag gactcagctt tctgaagccc ctcccagttc     180
tagttctatc ttttttcctgc atcctgtctg gaagttagaa ggaaacagac cacagacctg     240
gtccccaaaa gaaatggagg caataggttt tgaggggcat ggggacgggg ttcagcctcc     300
agggtcctac acacaaatca gtcagtggcc cagaagaccc cctcggaat cggagcaggg      360
aggatgggga gtgtgagggg tatccttgat gcttgtgtgt ccccaacttt ccaaatcccc     420
gcccccgcga tggagaagaa accgagacag aaggtgcagg gcccactacc gcttcctcca     480
gatgagctca tgggtttctc caccaaggaa gtttttccgct ggttgaatga ttcttttcccc     540
gccctcctct cgccccaggg acatataaag gcagttgttg gcacacccag ccagcagacg     600
ctccctcagc aaggacagca gaggaccagc taagagggag agaagcaact acagacccc      660
cctgaaaaca accctcagac gccacatccc ctgacaagct gccaggcagg ttctcttcct     720
ctcacatact gacccacggc tccaccctct ctccccctgga aaggacacca tgagcactga     780
aagcatgatc cgggacgtgg agctggccga ggaggcgctc cccaagaaga caggggggcc     840
ccagggctcc aggcggtgct tgttcctcag cctcttctcc ttcctgatcg tggcaggcgc     900
caccacgctc ttctgcctgc tgcactttgg agtgatcggc ccccagaggg aagaggtgag     960
tgcctggcca gccttcatcc actctcccac ccaaggggaa atggagacgc aagagaggga    1020
gagagatggg atgggtgaaa gatgtgcgct gataggagg gatggagaga aaaaacgtg      1080
gagaaagacg gggatgcaga aagagatgtg gcaagagatg gggaagagag agagagaaag    1140
```

```
atggagagac aggatgtctg gcacatggaa ggtgctcact aagtgtgtat ggagtgaatg   1200
aatgaatgaa tgaatgaaca agcagatata taaataagat atggagacag atgtggggtg   1260
tgagaagaga gatggggggaa gaaacaagtg atatgaataa agatggtgag acagaaagag   1320
cgggaaatat gacagctaag gagagagatg ggggagataa ggagagaaga agatagggtg   1380
tctggcacac agaagacact cagggaaaga gctgttgaat gcctggaagg tgaatacaca   1440
gatgaatgga gagagaaaac cagacacctc agggctaaga gcgcaggcca gacaggcagc   1500
cagctgttcc tcctttaagg gtgactccct cgatgttaac cattctcctt ctccccaaca   1560
gttccccagg gacctctctc taatcagccc tctggcccag gcagtcagta agtgtctcca   1620
aacctctttc ctaattctgg gtttgggttt ggggtaggg ttagtaccgg tatgaagca    1680 gtgggggaaa tttaaagttt tggtcttggg ggaggatgga tggaggtgaa agtaggggg    1740 tattttctag gaagtttaag ggtctcagct ttttcttttc tctctcctct tcaggatcat   1800
cttctcgaac cccgagtgac aagcctgtag cccatgttgt aggtaagagc tctgaggatg   1860
tgtcttggaa cttggagggc taggatttgg ggattgaagc ccggctgatg gtaggcagaa   1920
cttggagaca atgtgagaag gactcgctga gctcaaggga agggtggagg aacagcacag   1980
gccttagtgg gatactcaga acgtcatggc caggtgggat gtgggatgac agacagagag   2040
gacaggaacc ggatgtgggg tgggcagagc tcgagggcca ggatgtggag agtgaaccga   2100
catggccaca ctgactctcc tctccctctc tccctccctc cagcaaaccc tcaagctgag   2160
gggcagctcc agtggctgaa ccgccgggcc aatgccctcc tggccaatgg cgtggagctg   2220
agagataacc agctggtggt gccatcagag ggcctgtacc tcatctactc ccaggtcctc   2280 ttcaaggcc aaggctgccc ctccacccat gtgctcctca cccacaccat cagccgcatc   2340
gccgtctcct accagaccaa ggtcaacctc ctctctgcca tcaagagccc ctgccagagg   2400
gagaccccag aggggctga ggccaagccc tggtatgagc ccatctatct gggaggggtc   2460
ttccagctgg agaagggtga ccgactcagc gctgagatca atcggcccga ctatctcgac   2520
tttgccgagt ctgggcaggt ctactttggg atcattgccc tgtgaggagg acgaacatcc   2580
aaccttccca aacgcctccc ctgccccaat ccctttatta ccccctcctt cagacaccct   2640
caacctcttc tggctcaaaa agagaattgg gggcttaggg tcggaaccca agcttagaac   2700
tttaagcaac aagaccacca cttcgaaacc tgggattcag gaatgtgtgg cctgcacagt   2760
gaagtgctgg caaccactaa gaattcaaac tggggcctcc agaactcact ggggcctaca   2820
gctttgatcc ctgacatctg gaatctggag accagggagc ctttggttct ggccagaatg   2880
ctgcaggact tgagaagacc tcacctagaa attgacacaa gtggacctta ggccttcctc   2940
tctccagatg tttccagact tccttgagac acggagccca gccctcccca tggagccagc   3000
tccctctatt tatgtttgca cttgtgatta tttattattt atttattatt tatttattta   3060
cagatgaatg tatttatttg ggagaccggg gtatcctggg ggacccaatg taggagctgc   3120
cttggctcag acatgttttc cgtgaaaacg gagctgaaca ataggctgtt cccatgtagc   3180
cccctggcct ctgtgccttc ttttgattat gttttttaaa atatttatct gattaagttg   3240
tctaaacaat gctgatttgg tgaccaactg tcactcattg ctgagcctct gctccccagg   3300
ggagttgtgt ctgtaatcgc cctactattc agtggcgaga aataaagttt gcttagaaaa   3360
gaaacatggt ctccttcttg gaattaattc tgcatctgcc tcttcttgtg ggtgggaaga   3420
agctccctaa gtcctctctc cacaggcttt aagatccctc ggacccagtc ccatccttag   3480
actcctaggg ccctggagac cctacataaa caaagcccaa cagaatattc cccatccccc   3540
```

```
aggaaacaag agcctgaacc taattacctc tccctcaggg catgggaatt tccaactctg    3600
ggaattccaa tccttgctgg gaaaatcctg cagctcaggt gagatttccg gctgttgcag    3660
ctggccagca gtccggagag agctggagag gagccgcatt ctcaggtacc tgaatcacac    3720
agccaaggga cttccagaga ttcgggtgtc taggcttcaa atcaccctgt cctaactctg    3780
caacctgaac cagccactta acctatctat ccaatgggga taggaatgtc caccacacat    3840
agggcatgtg agagaaggcc tgacctccat cagaggacct cactcagccc ttggcacagt    3900
gggcacttag tgaattctgg cttccttcaa ccagttttcca gctgttctat cccctccat    3960 tctctcagtg ggtgaaatcg aagagactga ggacaataaa gaacaaggaa ccgaactgcc    4020
ggacgtggtg gcatgcacct gtaatcctac cactttgcaa ggccaaggtg agaggatcgc    4080
ttgaacccag gagttccaga gcaacctggg caacatagtg agatcctgtc tctattttt     4140 aaaaaagaat gaaacatagg aataagatgt gggtgaagga ctcacatgcc ggcttggtcc    4200
cactggtctt tgtggtgaag gaggggagag gtgagaggtg ggtaatccgg aaagagaaaa    4260 gcacccctc cctggatgaa ggctcttctg gagagagtca aagacaaata agggtggggc     4320
gcagtggctc atgcctgtta tcccaacact ttggaggct gaggtgggag gaccacttga     4380
gcccactagt tcaagaccag cctgtgcaac atagcaagac cttgtttcta gaaaaaaaat    4440
taaagattag tcaggtgtag tggtgcatgc ctgtaatcct agctcctcag gaggctgagg    4500
caggaggatc actcaagccc aggagtttga ggttacagta agctatgatc atgccactgt    4560 accccccgtct gggtgacaga acgagaccct gtctcaaaaa aataataatt ccaaaaacaa    4620
atatggagac ggaaattgag ccccctaga ctgggagccc ccactgagtt cggaaattag      4680
gctttacctc cagccctggg gtgccaggca ggagaaaacc atgtggtagg ctgaggggt      4740 agggtgaccc attggggtga cctagatagg gccttgggtc accctctgcc tcctccagcc    4800
tgtggctgaa agtcagccat gaagtaatgg                                      4830

<210> SEQ ID NO 25
<211> LENGTH: 737
<212> TYPE: DNA
<213> ORGANISM: Homo sapiens

<400> SEQUENCE: 25
tacccacctc aggtagccta gtgatatttg caaaatccca atggcccggt ccttttcttt      60
actgatggcc gtgctggtac tcagctacaa atccatctgc tctctgggct gtgatctgcc    120
tcagacccac agcctgcgta ataggagggc cttgatactc ctggcacaaa tgggaagaat    180
ctctcctttc tcctgcttga aggacagaca tgaattcaga ttcccggagg aggagtttga    240
tggccaccag ttcagaagaa ctcaagccat ctctgtcctc catgagatga tccagcagac    300
cttcaatctc ttcagcacag aggactcatc tgctgcttgg gaacagagcc tcctagaaaa    360
attttccact gaactttacc agcaactgaa tgacctggaa gcatgtgtga tacaggaggt    420 tgggtggaa gagactcccc tgatgaatga ggacttcatc ctggctgtga ggaaatactt     480
ccaaagaatc actctttatc taacagagaa gaaatacagc cctgtgcct gggaggttgt     540 cagagcagaa atcatgagat ccttctcttt ttcaacaaac ttgaaaaaag gattaaggag    600
gaaggattga aaactggttc atcatggaaa tgattctcat tgactaatgc atcatctcac    660
actttcatga gttcttccat ttcaaagact cacttctata accaccacaa gttgaatcaa    720
aatttccaaa tgttttc                                                    737
```

```
<210> SEQ ID NO 26
<211> LENGTH: 5961
<212> TYPE: DNA
<213> ORGANISM: Homo sapiens

<400> SEQUENCE: 26
agcaaatgat caatgtgctt tgtgaatgaa gagtcaacat tttaccaggg cgaagtgggg      60
aggtacaaaa aaatttccag tccttgaatg gtgtgaagta aaagtgcctc aaagaatccc     120
accagaatgg cacaggtggg cataatgggt ctgtctcatc gtcaaaggac ccaaggagtc     180
taaaggaaac tctaactaca acacccaaat gccacaaaac cttagttatt aatacaaact     240
atcatccctg cctatctgtc accatctcat cttaaaaaac ttgtgaaaat acgtaatcct     300
caggagactt caattaggta taaataccag cagccagagg aggtgcagca cattgttctg     360
atcatctgaa gatcagctat tagaagagaa agatcagtta agtcctttgg acctgatcag     420
cttgatacaa gaactactga tttcaacttc tttggcttaa ttctctcgga acgatgaaa      480 tatacaagtt atatcttggc ttttcagctc tgcatcgttt tgggttctct tggctgttac     540
tgccaggacc catatgtaaa agaagcagaa aaccttaaga atatttttgt aagtatgact     600
ttttaatagt acttgtttgt ggttgaaaat gactgaatat cgacttgctg tagcatctct     660
gataggctgt catctcttgt aggcagtcat tttgagattt ggtgttattt tgttaattat     720
tgactagatg agttccttga ctaaataatc tagatattgt tttaaccttc tgctcagttt     780
gtatagagac ttaaaaggga tttatgaatt ttccaaaaga tgggcataat atgggtatga     840
agcataatga tgttaataat tttgtggtgg gaactcattc agttgtgata gtcaaggagt     900
atgcagattg aaaaaaatga ttggttatta gttttttgact tctcagactc taaggtcaag     960
attagcatta aaaaggtaat aggaaatgtt tacaaattaa agtcaaaaag gtccttaaag    1020
ctttggctta aaaaaataac tgataggtga ttttctccaa aaagtgattt caacattctg    1080
cttctctatc tatattactt gtgaagtatt ccggaacttc gttgctcact gggattttgg    1140
aagaattatg attctggcta aggaatgttt aaaaatttta agtgaatttt ttgagtttct    1200
tttaaaattt tattgatggt taatgaaaag tttttacatt ttaaatattt cattatttgt    1260
ttaaaactta gctgttataa ttatagctgt cataataata ttcagacatt cacaattgat    1320
tttattctta caacacaaaa tcaaatctca cacacacaca cacacacaca cactcgcaca    1380
tgtttggaac tatctttaa agctcgtata ataatacct acaggaaggc acagtagatg    1440
taatagaaac ctgtaccatt gggggggcagt atttttatagt ggggtggctt tgctgttttt    1500 tgttttttgta ttttttagcc tagcttgaaa atactttctt tagcttacta tagttttttgg    1560 gacctttgga gtatcagctt tgttgagctc atttgtgaca ttgcaattta atggttatat    1620
tgggaaataa aaaagctaaa agaacataat agtctttgtc tatatctcac ataagccttt    1680
tgggaatact tattgttaga actaagcaga agagttgaaa aggaaatcag tgaatattgt    1740
cacatctgag ttcaatgaaa cttgaaatat atttttaagg caatttatgg gctaattgta    1800
aaccaatttt ttctttttttt tttttagaat gcaggtcatt cagatgtagc ggataatgga    1860
actcttttct taggcatttt gaagaattgg aaagaggtaa gctgaatatt cccatttggc    1920
taattttcct gttgcttgct ttctgatgga taaattcaca tcatcctctg tttgtgctct    1980
ttccttccaa ggagagtgac agaaaaataa tgcagagcca aattgtctcc ttttacttca    2040
aactttttaa aaactttaaa gatgaccaga gcatccaaaa gagtgtggag accatcaagg    2100
aagacatgaa tgtcaagttt ttcaatagca acaaaagaa acgagatgac ttcgaaaagc    2160
tgactaatta ttcggtgagg ctatttaaat tctttctttg gtttcattgc cgagggtctt    2220
```

```
gcaaagcatt tattctccag aaagtagaca ttagctattt aacagttgct aaagctatga    2280
actcaactca tggctgaaac tctaccttac tatttccatt cgtgtttggg tgactttgca    2340
aagccagtaa gagaatcgct gaagtatgta atgtagagaa atgctggcat tgtaactatt    2400
gcgtaaagac aggtgagttg acaaattcca gtgaagagga agtaggtgag gaagaagcag    2460
ggagtactga gaagcagttc tctcattgtc ccttgctcat atgatggaaa ttctcttact    2520
ttgaatgaga ggctgtctgt cttaatggaa agagcagtgg gaggagctga gaagatgtgt    2580
gttctcctcc caactcagcc accaaggaac tgtgatgaat cacatggctg gctgggctca    2640
gtttcctcat cttaaaagga aactgttagg ttcactgtat aagtttgatg accttctttg    2700
ctccaaaact ctacaatgca aagaatagaa atgagaatg agatagaaga aagctacagt    2760 cttttgaatag gtaccaggga cacccactg caagtctcta gccaacctat cagattgtac    2820
tgcccaatta gaagcaagaa tggttgctgt ttgtttgttt ttagggaaaa atagatagaa    2880
tttataccct atgaaaagat tgttctatca actctctatc aactttcaga atatctcagc    2940
tggagaactc cttagactcc taagtcttac ctcatgaact tgtatcttta agttatggct    3000
tctataaaca gaaagataac gttgaggcat aaagacaaat catgttttc agaatgttt    3060 ctagaagaca aaggcctcta gattcctttg gggttgactt tgatataaat gggctcaaat    3120
gagagggacc agggtcttca agctagcatt tgtgttctta ggatatgtgc tcagctttca    3180
ctattgctgg gcctgcctct cactcctctc atgtaagccc ccagaaacag aaaggagaga    3240
catggcaaca ggtctccttt ggttataaac tagacactca gcacttgttt ctaatccagt    3300
ggtgcccctg gcttactgtt cagtcctgga taagtctctt agtttcttgg tgatgatttg    3360
aacattggaa agtaaaatct gtcacttgca aacacacagc ttgtcgaaaa ttttttctac    3420
tctgcaggaa ctgggcctta aaaaaatgaa aaaaaatctg tggtttcttc cttctggaag    3480
ctacaaacct cctgtttctt gatgggcaat cttgagtgag ctctattaat tattattctc    3540
tttggctcag ttgctaagct attttatgca tgttatgccc tttgacaatt agtctttagc    3600
tgtaatcccc cagccatcct cagaaatgtg gtgaggtagc catagtgttc ccaagattag    3660
aaaaatgtaa tggcagagcc aagaggaagg taaatggtcc acatcttatg aagcatcatc    3720
taaatggccc tattggttag agtgaggaga tgcaagtagt tcaatttgct tgcctagaag    3780
gcagggtact ggaaaagttg ttgcaattct taattttaaa ctttatatat cagtaagcca    3840
tatataaata tgattggggg tgtttatttt aaaatctatt atggaaattg agagactgac    3900
ctaatctggg agaaattaaa aattacagtt ttcactcgtt ttggatttgg tgttttctag    3960
ggtacctaac ctagatcagt ggttctcaaa cttaggtgga tgtcagaatc acctggggag    4020
cttagtgaat gcacagggca cagtccttcc acttcatgca cctggatctc tgaggtcttt    4080
gacaggtttc cggattaatc tgctatgcac aacagtgaga atcattgacc tatagttact    4140
catttgatgc atacaggaaa gactgaagta taaagtgata taattggtag attgatgata    4200
gagaggtcat agaaacagtc tcatcctcct ttagatgaga aaatagaagt tcagagaggt    4260
taagtagctg gctcaaggtc agaattattg catgcatgag attcaaaccc accttttat    4320 gctgactcca caaccaggag tctttttcact atataatttc aagaattcta tagaagtaga    4380
tttaaagata tgtgatggac tccaccacat tatagcacaa ctagaaatgt aattgtaatt    4440
tttagcttca actgctgaag aagtaaatat tgtatattaa ggtaatacgg tccatttttt    4500
aaaggaatac ttttatttc actgaccatc atgaccattag cagaatatcc tgatggctta    4560
tatgcctgaa attaattttg ctcttttctt tcccgatagg taactgactt gaatgtccaa    4620
```

| | | | | |
|---|---|---|---|---|
| cgcaaagcaa | tacatgaact | catccaagtg | atggctgaac | tgtcgccagc agctaaaaca | 4680 |
| gggaagcgaa | aaaggagtca | gatgctgttt | cgaggtcgaa | gagcatccca gtaatggttg | 4740 |
| tcctgcctgc | aatatttgaa | ttttaaatct | aaatctattt | attaatattt aacattattt | 4800 |
| atatggggaa | tatattttta | gactcatcaa | tcaaataagt | atttataata gcaacttttg | 4860 |
| tgtaatgaaa | atgaatatct | attaatatat | gtattattta | taattcctat atcctgtgac | 4920 |
| tgtctcactt | aatcctttgt | tttctgacta | attaggcaag | gctatgtgat tacaaggctt | 4980 |
| tatctcaggg | gccaactagg | cagccaacct | aagcaagatc | ccatgggttg tgtgtttatt | 5040 |
| tcacttgatg | atacaatgaa | cacttataag | tgaagtgata | ctatccagtt actgccggtt | 5100 |
| tgaaaatatg | cctgcaatct | gagccagtgc | tttaatggca | tgtcagacag aacttgaatg | 5160 |
| tgtcaggtga | ccctgatgaa | aacatagcat | ctcaggagat | ttcatgcctg gtgcttccaa | 5220 |
| atattgttga | caactgtgac | tgtacccaaa | tggaaagtaa | ctcatttgtt aaaattatca | 5280 |
| atatctaata | tatatgaata | aagtgtaagt | tcacaactac | ttatgctgtg ttggactttt | 5340 |
| tctaagtgag | acctggagtg | aaagaactac | ctattaatga | attagtaggg aggggagtct | 5400 |
| tcttagctgt | gaaaatttta | gagttgcatt | tggttccatt | aaatgtggta tttctttcca | 5460 |
| ctagcatttt | gttggctttc | gcttttccag | ttagcagctc | tttgaattat ctttctaaga | 5520 |
| tacagattta | attatgtcac | tattcaattc | agaggttctg | ctatggaatg tagttttaaac | 5580 |
| tgcttagctt | ggcacacaga | gatttatttc | tagccccttc | tccaccttcc tatttcctcc | 5640 |
| ttcgtttcag | aatcttcctc | tccctcatcc | aatgctggca | acaccagtg ggggtggagt | 5700 |
| agtgggtgta | agctctaggg | agaaggcttg | gattggaatc | caagttattc cattacaagt | 5760 |
| agtgtgacct | ttaatacatt | atgtatattg | tctaagtttc | agctttattg tctgaaaaag | 5820 |
| aaaaataatt | gtgtgttcct | cataatattg | tggtacgaat | tgattctttc actcaagaaa | 5880 |
| tatttactgg | agtacctact | acatgcctgg | tgctgttgta | gaccttgaga taccttactc | 5940 |
| aagcaaaaca | gccaaggatc | c | | | 5961 |

<210> SEQ ID NO 27
<211> LENGTH: 2430
<212> TYPE: DNA
<213> ORGANISM: Homo sapiens

<400> SEQUENCE: 27

| | | | | |
|---|---|---|---|---|
| catttcattg | gcgtttgagt | cagcaaagaa | gtcaagatgg | ccaaagttcc agacatgttt | 60 |
| gaagacctga | agaactgtta | cagtgaaaat | gaagaagaca | gttcctccat tgatcatctg | 120 |
| tctctgaatc | agaaatcctt | ctatcatgta | agctatggcc | cactccatga aggctgcatg | 180 |
| gatcaatctg | tgtctctgag | tatctctgaa | acctctaaaa | catccaagct taccttcaag | 240 |
| gagagcatgg | tggtagtagc | aaccaacggg | aaggttctga | agaagagacg gttgagttta | 300 |
| agccaatcca | tcactgatga | tgacctggag | gccatcgcca | atgactcaga ggaagaaatc | 360 |
| atcaagccta | ggtcagcacc | ttttagcttc | ctgagcaatg | tgaaatacaa ctttatgagg | 420 |
| atcatcaaat | acgaattcat | cctgaatgac | gccctcaatc | aaagtataat tcgagccaat | 480 |
| gatcagtacc | tcacggctgc | tgcattacat | aatctggatg | aagcagtgaa atttgacatg | 540 |
| ggtgcttata | agtcatcaaa | ggatgatgct | aaaattaccg | tgattctaag aatctcaaaa | 600 |
| actcaattgt | atgtgactgc | ccaagatgaa | gaccaaccag | tgctgctgaa ggagatgcct | 660 |
| gagatacccca | aaaccatcac | aggtagtgag | accaacctcc | tcttcttctg ggaaactcac | 720 |
| ggcactaaga | actatttcac | atcagttgcc | catccaaact | tgtttattgc cacaaagcaa | 780 |

| | |
|---|---|
| gactactggg tgtgcttggc aggggggcca ccctctatca ctgactttca gatactggaa | 840 |
| aaccaggcgt aggtctggag tctcacttgt ctcacttgtg cagtgttgac agttcatatg | 900 |
| taccatgtac atgaagaagc taaatccttt actgttagtc atttgctgag catgtactga | 960 |
| cccttgtaat tctaaatgaa tgtttacact ctttgtaaga gtggaaccaa cactaacata | 1020 |
| taatgttgtt atttaaagaa caccctatat tttgcatagt accaatcatt ttaattatta | 1080 |
| ttcttcataa caattttagg aggaccagag ctactgacta tggctaccaa aaagactcta | 1140 |
| cccatattac agatgggcaa attaaggcat aagaaaacta agaaatatgc acaatagcag | 1200 |
| ttgaaacaag aagccacaga cctaggattt catgatttca tttcaactgt ttgccttcta | 1260 |
| cttttaagtt gctgatgaac tcttaatcaa atagcataag tttctgggac ctcagtttta | 1320 |
| tcattttcaa aatggaggga ataataccta agccttcctg ccgcaacagt tttttatgct | 1380 |
| aatcagggag gtcattttgg taaaatactt cttgaagccg agcctcaaga tgaaggcaaa | 1440 |
| gcacgaaatg ttatttttta attattattt atatatgtat ttataaatat atttaagata | 1500 |
| attataatat actatattta tgggaacccc ttcatcctct gagtgtgacc aggcatcctc | 1560 |
| cacaatagca gacagtgttt tctgggataa gtaagtttga tttcattaat acagggcatt | 1620 |
| ttggtccaag ttgtgcttat cccatagcca ggaaactctg cattctagta cttgggagac | 1680 |
| ctgtaatcat ataataaatg tacattaatt accttgagcc agtaattggt ccgatctttg | 1740 |
| actcttttgc cattaaactt acctgggcat tcttgtttca ttcaattcca cctgcaatca | 1800 |
| agtcctacaa gctaaaatta gatgaactca actttgacaa ccatgagacc actgttatca | 1860 |
| aagttgagtt catctaattt tagcttgtag agacgggatt tcaccatctt ggccgtgctg | 1920 |
| gtctcgaact tctgacctcg tgatccaccc gcctcggcct cccaaagtgc tgggattaca | 1980 |
| ggcgtgagcc atcgcgcccg gcctggagtt tctactgtgc accaggcact accttttacat | 2040 |
| gtattgtttt atttaatcct cagtcagccg tgtttggtag gtgcagttag tatatttcca | 2100 |
| ttttcatctg cgcaaacaga ttcaggaact ttgtaattta cataaggtca cattcatcct | 2160 |
| aattcacaaa atcaagattt cacacctatt ccttttttctt tccagtgcct gtgcttttc | 2220 |
| tctcatacca aggagaagta ataagcctaa cgttttaaac ctcacaaaag tacatacaga | 2280 |
| aaagtaaata gcctaatttt gcaactaata caaatggcgc tgtacttctt tggtgatggt | 2340 |
| agatttataa tttttgaagt atggtagatt caaatgaacc actgaaaagg catttagttt | 2400 |
| cttgtcccaa ataaaaaaaa aaaaaaaaaa | 2430 |

<210> SEQ ID NO 28
<211> LENGTH: 5561
<212> TYPE: DNA
<213> ORGANISM: Homo sapiens

<400> SEQUENCE: 28

| | |
|---|---|
| cgaattcccc tatcacctaa gtgtgggcta atgtaacaaa gagggatttc acctacatcc | 60 |
| attcagtcag tctttggggg tttaaagaaa ttccaaagag tcatcagaag aggaaaaatg | 120 |
| aaggtaatgt ttttttcagac tggtaaagtc tttgaaaata tgtgtaatat gtaaaacatt | 180 |
| ttgacacccc cataatattt ttccagaatt aacagtataa attgcatctc ttgttcaaga | 240 |
| gttccctatc actctttaat cactactcac agtaacctca actcctgcca caatgtacag | 300 |
| gatgcaactc ctgtcttgca ttgcactaag tcttgcactt gtcacaaaca gtgcacctac | 360 |
| ttcaagttct acaagaaaaa cacagctaca actggagcat ttactgctgg atttacagat | 420 |
| gattttgaat ggaattaatg taagtatatt tccttttctta ctaaaattat tacatttagt | 480 |

```
aatctagctg gagatcattt cttaataaca atgcattata ctttcttaga attacaagaa    540
tcccaaactc accaggatgc tcacatttaa gttttacatg cccaagaagg taagtacaat    600
attttatgtt caatttctgt tttaataaaa ttcaaagtaa tatgaaaatt tgcacagatg    660
ggactaatag cagctcatct gaggtaaaga gtaactttaa tttgtttttt tgaaaaccca    720
agtttgataa tgaagcctct attaaaacag ttttacctat attttttaata tatatttgtg    780 tgttggtggg ggtgggagaa acataaaaa taatattctc tcactttatc gataagacaa    840
ttctaaacaa aaatgttcat ttatggtttc atttaaaaat gtaaaactct aaaatatttg    900
attatgtcat tttagtatgt aaaataccaa aatctatttc caaggagccc acttttaaaa    960
atcttttctt gttttaggaa aggtttctaa gtgagaggca gcataacact aatagcacag   1020
agtctggggc cagatatctg aagtgaaatc tcagctctgc catgtcctag ctttcatgat   1080
ctttggcaaa ttacctactc tgtttgtgat tcagtttcat gtctacttaa atgataact   1140 gtatatactt aatatggctt tgtgagaatt agtaagtaaa tgtaaagcac tcagaaccgt   1200
gtctggcata aggtaaatac catacaagca ttagctatta ttagtagtat taagataaa   1260 attttcactg agaaatacaa agtaaaattt tggactttat cttttttacca atagaacttg   1320 agatttataa tgctatatga cttattttcc aagattaaaa gcttcattag gttgttttg   1380 gattcagata gagcataagc ataatcatcc aagctcctag gctacattag gtgtgtaaag   1440
ctacctagta gctgtgccag ttaagagaga atgaacaaaa tctggtgcca gaaagagctt   1500
gtgccagggt gaatccaagc ccagaaaata ataggattta aggggacaca gatgcaatcc   1560
cattgactca aattctatta attcaagaga aatctgcttc taactaccct tctgaaagat   1620
gtaaaggaga cagcttacag atgttactct agtttaatca gagccacata atgcaactcc   1680
agcaacataa agatactaga tgctgttttc tgaagaaaat ttctccacat tgttcatgcc   1740
aaaaacttaa acccgaattt gtagaatttg tagtggtgaa ttgaaagcgc aatagatgga   1800
catatcaggg gattggtatt gtcttgacct acctttccca ctaaagagtg ttagaaagat   1860
gagattatgt gcataattta ggggtggtag aattcatgga aatctaagtt tgaaaccaaa   1920
agtaatgata aactctattc atttgttcat ttaaccctca ttgcacattt acaaaagatt   1980
ttagaaacta ataaaaatat ttgattccaa ggatgctatg ttaatgctat aatgagaaag   2040
aaatgaaatc taattctggc tctacctact tatgtggtca aattctgaga tttagtgtgc   2100
ttatttataa agtggagatg atacttcact gcctacttca aaagatgact gtgagaagta   2160
aatgggccta ttttggagaa aattcttta aattgtaata taccatagaa atatgaaata   2220
ttatatataa tatagaatca agaggcctgt ccaaaagtcc tcccaaagta ttataatctt   2280
ttatttcact gggacaaaca ttttaaaat gcatcttaat gtagtgattg tagaaaagta   2340
aaaatttaag acatatttaa aaatgtgtct tgctcaaggc tatattgaga gccactacta   2400
catgattatt gttacctagt gtaaaatgtt gggattgtga tagatggcat ccaagagttc   2460
cttctctctc aacattctgt gattcttaac tcttagacta tcaaatatta taatcataga   2520
atgtgatttt tatgccttcc acattctaat ctcatctggt tctaatgatt ttctatgcag   2580
attggaaaag taatcagcct acatctgtaa taggcattta gatgcagaaa gtctaacatt   2640
ttgcaaagcc aaattaagct aaaaccagtg agtcaactat cacttaacgc tagtcatagg   2700
tacttgagcc ctagttttc cagttttata atgtaaactc tactggtcca tctttacagt   2760
gacattgaga acagagagaa tggtaaaaac tacatactgc tactccaaat aaaataaatt   2820
ggaaattaat ttctgattct gacctctatg taaactgagc tgatgataat tattattcta   2880
```

```
ggccacagaa ctgaaacatc ttcagtgtct agaagaagaa ctcaaacctc tggaggaagt    2940
gctaaattta gctcaaagca aaactttca cttaagaccc agggacttaa tcagcaatat     3000
caacgtaata gttctggaac taaaggtaag gcattacttt atttgctctc ctggaaataa    3060
aaaaaaaaaa gtaggggaa aagtaccaca ttttaaagtg acataacatt tttggtattt     3120
gtaaagtacc catgcatgta attagcctac attttaagta cactgtgaac atgaatcatt    3180
tctaatgtta aatgattaac tggggagtat aagctactga gtttgcacct accatctact    3240
aatggacaag cctcatccca aactccatca cctttcatat aaacacaaaa ctgggagtga    3300
gagagaagtg actgagttga gtttcacaga aacgcaggca agattttatt atatatttt    3360 caagttcctt cacagatcat ttactggaat agccaatact gagttacctg aaaggctttt    3420
caaatggtgt ttccttatca tttgatggaa ggactaccca taagagattt gtcttaaaaa    3480
aaaaaactgg agccattaaa atggccagtg gactaaacaa acaacaatct ttttagaggc    3540
aatcccactt tcagaatctt aagtattttt aaatgcacag gaagcataaa atatgcaagg    3600
gactcaggtg atgtaaaaga gattcacttt tgtcttttta tatcccgtct cctaaggtat    3660
aaaattcatg agttaatagg tatcctaaat aagcagcata agtatagtag taaaagacat    3720
tcctaaaagt aactccagtt gtgtccaaat gaatcactta ttagtggact gtttcagttg    3780
aattaaaaaa atacattgag atcaatgtca tctagacatt gacagattca gttccttatc    3840
tatggcaaga gttttactct aaaataatta acatcagaaa actcattctt aactcttgat    3900
acaaatttaa gacaaaacca tgcaaaaatc tgaaaactgt gtttcaaaag ccaaacactt    3960
tttaaaataa aaaaatccca agatatgaca atatttaaac aattatgctt aagaggatac    4020
agaacactgc aacagttttt taaaagagaa tacttattta aagggaacac tctatctcac    4080
ctgcttttgt tcccagggta ggaatcactt caaatttgaa aagctctctt ttaaatctca    4140
ctatatatca aaatagttgc ctccttagct tatcaactag aggaagcgtt taaatagctc    4200 cttttcagcag agaagcctaa tttctaaaaa gccagtccac agaacaaaat ttctaatgtt    4260
taaagctttt aaaagttggc aaattcacct gcattgatac tatgatgggg tagggatagg    4320
tgtaagtatt tatgaagatg ttcattcaca caaatttacc caaacaggaa gcatgtccta    4380
cctagcttac tctagtgtag ctcgtttcgt ctttggggaa aatataagga gattcactta    4440
agtagaaaaa taggagactc taatcaagat ttagaaaaga agaaagtata atgtgcatat    4500
caattcatac atttaactta cacaaatata ggtgtacatt cagaggaaaa gcgatcaagt    4560
ttatttcaca tccagcattt aatatttgtc tagatctatt tttatttaaa tctttatttg    4620
cacccaattt agggaaaaaa ttttgtgtt cattgactga attaacaaat gaggaaaatc      4680
tcagcttctg tgttactatc atttggtatc ataacaaaat acgcaatttt ggcattcatt    4740
ttgatcattt caagaaaatg tgaataatta atatgtttgg taagcttgaa aataaaggca    4800
acaggcctat aagcttcaa ttgggaataa ctgtatataa ggtaaactac tctgtactt     4860 aaaaaattaa catttttctt ttatagggat ctgaaacaac attcatgtgt gaatatgctg    4920
atgagacagc aaccattgta gaattctga acagatggat tacctttgt caaagcatca      4980 tctcaacact gacttgataa ttaagtgctt cccacttaaa acatatcagg ccttctattt    5040
atttaaatat ttaaatttta tatttattgt tgaatgtatg gtttgctacc tattgtaact    5100
attattctta atcttaaaac tataaatatg gatcttttat gattcttttt gtaagcccta    5160
ggggctctaa aatggtttca cttatttatc ccaaaatatt tattattatg ttgaatgtta    5220
aatatagtat ctatgtagat tggttagtaa aactatttaa taaatttgat aaatataaac    5280
```

```
aagcctggat atttgttatt ttggaaacag cacagagtaa gcatttaaat atttcttagt    5340
tacttgtgtg aactgtagga tggttaaaat gcttacaaaa gtcactcttt ctctgaagaa    5400
atatgtagaa cagagatgta gacttctcaa aagcccttgc tttgtccttt caagggctga    5460 tcagacccctt agttctggca tctcttagca gattatattt tccttcttct taaaatgcca    5520
aacacaaaca ctcttgaaac tcttcataga tttggtgtgg c                        5561
```

<210> SEQ ID NO 29
<211> LENGTH: 674
<212> TYPE: DNA
<213> ORGANISM: Homo sapiens

<400> SEQUENCE: 29

```
gatccaaaca tgagccgcct gcccgtcctg ctcctgctcc aactcctggt ccgccccgga      60
ctccaagctc ccatgaccca gacaacgtcc ttgaagacaa gctgggttaa ctgctctaac    120
atgatcgatg aaattataac acacttaaag cagccacctt tgcctttgct ggacttcaac    180
aacctcaatg gggaagacca agacattctg atggaaaata accttcgaag gccaaacctg    240
gaggcattca cagggctgt caagagttta cagaacgcat cagcaattga gagcattctt    300
aaaaatctcc tgccatgtct gcccctggcc acggccgcac ccacgcgaca tccaatccat    360
atcaaggacg tgactggaa tgaattccgg aggaaactga cgttctatct gaaaacccctt   420 gagaatgcgc aggctcaaca gacgactttg agcctcgcga tcttttagtc caacgtccag    480
ctcgttctct gggccttctc accacagcgc tcgggacat caaaaacagc agaacttctg    540
aaacctctgg gtcatctctc acacattcca ggaccagaag catttcacct tttcctgcgg    600
catcagatga attgttaatt atctaatttc tgaaatgtgc agctcccatt tggccttgtg    660
cggttgtgtt ctca                                                       674
```

<210> SEQ ID NO 30
<211> LENGTH: 9900
<212> TYPE: DNA
<213> ORGANISM: Homo sapiens

<400> SEQUENCE: 30

```
gaattcaata aaaacaagc agggcgcgtg gtggggcact gactaggagg gctgatttgt      60
aagttggtaa gactgtagct cttttttccta attagctgag gatgtgttta ggttccattc   120
aaaaagtggg cattcctggc caggcatggt ggctcacacc tgtaatctca gagctttggg    180
agactgaggt aggaggatca cttgagccca ggaatttgag atgagcctag caacatagt    240 gagactctta tctctatcaa aaaataaaaa taaaaatgag ccaggcatgg tgcggtggac    300
cacgcaccta ctgctagggg ggctgaggtg ggaggatcat tgagcctggg aggttgaggc    360
tgcagtgatc cctgatcaaa cattgcattt cagcctgggt gacagagtga gacccctgtct   420 cagaaaaaaa aaaaaaagt cattcctgaa acctcagaat agacctacct tgccaagggc    480
ttccttatgg gtaaggacct tatgaccctg ctgggaccca actaggcct cacctgatac    540 gacctgtcct tctcaaaaca ctaaacttgg agaacattg tccccagtg ctgggtagg      600 agagtctgcc tgttattctg cctctatgca gagaaggagc cccagatcat cttttccatg    660
acaggacagt ttccaagatg ccacctgtac ttggaagaag ccaggttaaa atacttttca    720
agtaaaactt tcttgatatt actctatctt tccccaggag gactgcatta caacaaattc    780
ggacacctgt ggcctctccc ttctatgcaa agcaaaagc cagcagcagc cccaagctga    840
taagattaat ctaaagagca aattatggtg taatttccta tgctgaaact ttgtagttaa    900
```

```
tttttttaaaa aggtttcatt ttcctattgg tctgatttca caggaacatt ttacctgttt      960
gtgaggcatt ttttctcctg aagagaggt gctgattggc cccaagtgac tgacaatctg       1020
gtgtaacgaa aatttccaat gtaaactcat ttccctcgg tttcagcaat tttaaatcta       1080
tatatagaga tatctttgtc agcattgcat cgttagcttc tcctgataaa ctaattgcct      1140
cacattgtca ctgcaaatcg acacctatta atgggtctca cctcccaact gcttcccct      1200
ctgttcttcc tgctagcatg tgccggcaac tttgtccacg gacacaagtg cgatatcacc      1260
ttacaggaga tcatcaaaac tttgaacagc ctcacagagc agaaggtgag tacctatctg      1320
gcaccatctc tccagatgtt ctggtgatgc tctcagtatt tctaggcatg aaaacgttaa      1380
cagctgctag agaagttgga actggtggtt ggtggcagtc cagggcacac agcgaggctt      1440
ctccctgcca ctctttttc tgagggtttg taggaagttt cctcagttgg agggagtgag      1500
agctgctcat caaggacttc tctgtccggt tggaggttaa ctctgtctct tgctctctca      1560
tttctgcctg gaccaagact ctgtgcaccg agttgaccgt aacagacatc tttgctgcct      1620
ccaaggtaag aagccgtccc acggtctgtt ttagcaaatg gggagatcca tccccaaatg      1680
tctgaacaag aaacttgtct aatggaaaac gagcgggccc aaattaactc taaggtgtta      1740
gatgttttca aagaacgaga agtctgatct ttactcttaa gcatgttttg gtctttctgg      1800
tttcacttga tttagaagac atgtaataga aagcttacat gctgtagtcc tgactcagat      1860
cctggtcaaa gaaaagccct cttgggtttt acttagcttt ggcatagtgc ctggaacgta      1920
ggaggcactc aataaatgcc tgttaatga gagaatttt ctggcccata catttctgaa        1980
aaaccaaata ctctcacaga aacagatatt gagatgacag gttgagggag ctttcatttt      2040
gtctaagaga cttcctatgg caacagaaaa ggtatcgcca gagcccctcc tcttccacag      2100
cctggccacc taacagccct ctggttccgg ggctgccgtc cagagctctc agcttgctct      2160
ggccggccga actcccctcc agctcggtct ggaaccatcc tgctgggcag cgtccagcac      2220
atccctgctt cgggctgcct gggcacctcg cctctctgcc tcctgtgctg cctcacccc       2280
accctctat ctgtagtggg agggagatag atttgacagc tgatagtgca ttttctctga      2340
caaacacatg actacagccg tatcaatagt tttgtgcatt tcagttcctg ttttcatgga      2400
aacacacggc tgagaatgaa agccccaaag cctcaatttc acagtggtct cctaactacc      2460
tgctttccat gcaaactagg gagatgatat ggccaggagt gaagccctgt gtgttgggca      2520
gggtcacact ccagcaccca gaccatagaa cagggcccat cctgcttcat gagggaaact      2580
gctcttcggg cctttagctg gactatctca tttcattagt tatcccggga gtccgataca      2640
ggatgagatt ctgaagggca aatacacact ttttttttt ttttgagata gggtcttgtt       2700
ctgtcaccca ggctggagtg cagtggtgcg atttcagctc atagcagcct ccacctccca      2760
ggctcaagct atcttcctac ctcagcctcc caagtagccg ggacgacagg tgtgcaccac      2820
cacgcctggc taatttttgt atttttttgt agagatggag tcttgccatt ttgcccaggc      2880
ttgtctcgaa cttctgggct caagcaatcc gtccacctcg gcctctcaaa gtgctgggat      2940
tagccactgc acctgggcaa cagtttatgt gtgtgtgtgt gtgtgtgtgt atatatgtgt      3000
gtgtgtgtat atatatgtgt gtatgtatat atgtgtatgt atatgtgtgt gtgtgtgtgt      3060
gtgtgtgtgt gtgtataaaa tctccaagtc catccaaccg agatggctcc tactagaagc      3120
caagagtcca ccgggttgag cactgggtct ctggaggcct gtcggactgc tgagaaggct      3180
ctaacaaagc caagggaagg gccacctcac tagaagccag gcctggagga agggtgaggg      3240
ctgagggctg gaggtaagac tgcctgtggt tttagaccca ggctctgcca ctgactagct      3300
```

```
gtgtggctgg ccttcagaca tcttcacagc tctctgcacc tcagtttcca catgtgaaga    3360
tatgaaagtg attctgaagg tgattgcaag gttgattgga atccagctct tgagttagtg    3420
caaagtgtta ttgtgagatg atataaccac gattaaaagc aagaacaggt gcagagaagc    3480
gatgattcta agaaggaggg gaccgggttg gaaaggatca aaccatccag gatgccgagt    3540
ctggggcaat ccatctgggc tgtttctgga agaccccccgg gtgcaggcca ggacactgct    3600
gccctcccgt ccttaactcc cctcttcact cagtcctcac tcacctccct ctcacacaca    3660
caaacatctc ctagaataat ccccactgcc tgccttcact cttacccgtc tcatttgcct    3720
cccctgaact tcatcctcct ggagttcacg atctcactct tcactctttt cttcccctcg    3780
aagattcagc actgcttact tacatgttaa gatatttcag aacagtgaaa tgttgctatt    3840
ttcaaaaacc tacaaaggtg gtatgcagag gaaaaggtac ttctttgtgt tcccaaagaa    3900
aacatctttc caaaatccag cctattgatt ttatttcttc gggggaacaa gaattttagt    3960
atctctaagt tgggtagcat tctactcttg gcagttgctg gaaagaaggc actggtctag    4020
gtcctgggct tcacaggtaa cacctgtcag ggtgtctatg aagtcaaggc tgtctgagga    4080
acagcaaagt gggaagaagc aagctggctg gctgatgaag ggtttcttgg gtggacaagt    4140
agttggagcg atttcctatt taccaaagag agctaaagtt cataattcta cagagagttc    4200
cataatgaac ctcaaatacc tctgttttt gaaggagttt ctcatataca gcactagctg    4260
actatcctgg gcaggatggg agataatgaa tgcagtgcca atcgggctgg atttatatgg    4320
tcctagtgag gctggtcaag aaccgagtta gaactctcac agagtcactg cccacagaag    4380
aaatctccca agtggctgtt tcctgacatt cccgggaggc aggcctcctt ctgagtcact    4440
ccctaagcag ttctgaactg tgaggtcagc caggctgtcc aagtgcactc cctgagccac    4500
tggcagacac actcagcagc cagagctaga caggcaggtg gtaggagtcc agggccacgg    4560
cagggatgga gtgtcgcccc ctcgctgcga taccagagca agtaaaacgt taaggccttg    4620
cactaaagct gcccttagga tgcattcttt taaagttttt ccatttaatg cagactcttt    4680
tcaattctta ttttatcctt gtttcctta gaaagtcctt tgaaaaatat ctttagaggg    4740 tttttttccta tactatgtgg ccatatacgg gtcaaaatta agtttaattt ccaggctcca    4800
agccagcgtt tcagaaaaat ctcaccaagg tttgtggtaa aagaagcaaa gggctgactt    4860
tttggttttc ttgaatctca ctgttccctc tgcagcagca tgcatgtctg cccacctcca    4920
gacacacagg caccatctgc cgccccccat cagcccgtgt cccttccacc tcgactcgcc    4980
tacaaagccc agagaggtct gtttcttggc ccccagagcc caaagatact gacacactct    5040
tacatttcca actagaatca ggaacgagga gtgactctca gtcagttcat taagtaaatg    5100
tctttctaac cgctctgccc atgggacatc acgccccaca ggggaaaggg gaagcttctg    5160
tagcctggga ttctggtgcc tcagtctggg tctagacttt cctgaaaaaa cgttaaaata    5220
tgaactgcat tcctagaatt tagcctacat aaataagaga tgaacacaaa gatttctata    5280
gtttactcac tgccgcttat ttacagaagc aaaaatctgc cacgataggg gcctgacaaa    5340
tgacagtacc actgtgcaat gcgtttctac gcagctctca atcccatgtt ctctaatacc    5400
accgaaggct taggaaatgc ttatggtata tgtaaagagt aaagaagtta caaacagtat    5460
caacagttga cccctatttt aaaaagtatt tttgaaaagt gtgacgatat ttaccaaaat    5520
attaacgagc aatagttacc tctggctggt gggatgagtg aatgtatttt tgttgaatat    5580
atgttacctt tatagtaaat atatgttatc ttgatcatca gaaaaaaaaa tatgtaagaa    5640
cttgaaagct gcttggacag cgctgctgat agaaaccccct gagcatcttg tcactgttct    5700
```

```
tctgattcag agggtctggg tggggcaggg gtggtctgag attctgtatt tctaagaagc   5760
tcccagtgat gtccatgctg ctgtccatgg accacacttt gagtatcaag ggaccagagc   5820
atgtcggggg agaggctggg gatagctttc tttatctgaa ctggataaag gaactgggct   5880
caagctaaga accctctcca ggttctgcat ctttgttctt cagtgaaaaa tgagaggaca   5940
caccaggcca ggttcagact gagacacaat ccctctcctg ggttcccaat gacttgtctc   6000
ttgtccattc ccttctctaa ggctaagggc cccccaggaa gagccatgtg gccagaccct   6060
cacagttgct ggcattccaa ggagattctc actccgcatc attggtccaa aggccccttt   6120
acagaagctc tgcccaaggc tcagatcaat ggcacctgct cccagagctc ctctgatctc   6180
ccaggacacc tttccctgat ctgtgcactt atctcttgct gcctggcaaa atgtcttagc   6240
tcctcacttg ggccatgtgc tgctctcctc tcccatgggg agagccacac ggagagtgct   6300
ggccaaagca gcagagttca ggccaaagga tgtgcactca tttattcaac aggcatgcag   6360
gatttccagg gaaagctgga ttttaaaacc tctgggaaca agagcagaac ctgactgaga   6420
gctcatgtgg gcacttttca tagcagaata gctcatgagg tatagagaca cggacgcaga   6480
acgtgggctg tagcgacaga tggtcctgca ttctagtccc cactgtgcct tttcctcatg   6540
ggatgacttt attcaggtac cctttcggca aaatcctcca agagaaagga aactgggagg   6600
ttctggggag aaggctgctg cgtttgcaat gggagaggt tgttgacaga ggtttatgtc    6660
tgtggcaagc agccttcctt cagtggaata cttgaagaca ggtctgtagt tgagcaaact   6720
cacctccatt tgtcctcctg gaaagaagaa atcaagagga aaaatctctc tcccatcctc   6780
caaatggagc tggcacattg ctatctgtgg catttgtctt tccagaacac aactgagaag   6840
gaaaccttct gcagggctgc gactgtgctc cggcagttct acagccacca tgagaaggac   6900
actcgctgcc tgggtgcgac tgcacagcag ttccacaggc acaagcagct gatccgattc   6960
ctgaaacggc tcgacaggaa cctctgggc ctggcgggct tggtaagctg cactgtattc    7020
ctggcaagcc ggccgcgtgg ctcctggtgg acagcagcct cacttctaaa cactccttag   7080
gagctgcagc acccttggtc aacccattca ttcattcact cattcaataa gtatttgctg   7140
aagttccaca agtgctgggt gtggttctag gtgctgagga cgtgtcacta aagacagcag   7200
gccgagtccc tgttctcatg gaatgttcta atgggagagt tagaaaaaca aacatgtaaa   7260
atgatggcca gcagtgatac gtgctacaaa gaaaaacata gaaataaaga acataagagt   7320
catgggggag ggggctgact taggagctgg tgacattatc tgagcagata tttgaattga   7380
gggagcaggc cacatgacta actagggaga ccattccagg gagaaggagg aggtatgcaa   7440
aggccttagg atggaaatga actaacttcc tgtatttaaa gaccagtagg aaggccagtg   7500
tggctggatc agagtgagtg aggggtagtt tccaggacag cagatcacac aaggccttta   7560
gattccacca cgagtatgga gggaacacct gcagagcttt gggcaggaca agactgtac    7620
aatctgattt acgtgattta aaagggtcag tctggctact gtgtggtaaa taggctgaaa   7680
gggggaaagc atagaagcaa gatggcctgt gggaggcta ccacagtaaa ccaggctaga    7740
gatgatggtg gcgtggacag aatgaagcaa gatggcctgt gggaggcta ccacagtaaa    7800
ccaggctaga gatgatggtg gcgtggacag aatgaagcaa gatggcctgt gggaggcta    7860
ccacagtaaa ccaggctaga gatgatggtg gcgtggacaa atgagcagt tgaggtgaac    7920
agatttggga tatgactaaa aataaaacca gaagatttgc tgacagatcg gttgtagggg   7980
gtaagataca ggggaggaaa agatgacctc tttgttcctg cccaaacccc tctgcgatg    8040
gtcagtactg tttacagaga gatgaaagac tggcggcaag gcagggctgg aggttcagca   8100
```

| | |
|---|---|
| gaagatcaag agttcaattt tgtacatcgt acatgtaagg tggctcttgg atagccaagt | 8160 |
| gaaggtgttg agaagatggt tagaaaagtc tggaacttag gggagaggtc agaacttgca | 8220 |
| atacaaaaag gagagtcctt agatagatac tgctgaaaat ctgaatgaca gaaagggaga | 8280 |
| gatcaaagga ctgagcctga gatcaacaca tggaggtcag gagaggagga tccagccaag | 8340 |
| gggcctgagg aggagtgacc agtgaggcag gagaacatgg agagtgggcg gtaccccagg | 8400 |
| aagccggtga ggacactcaa ggagggaggg ttgactgtgt caaatgtact gaaaggacag | 8460 |
| gtcaggtgag gaccaagaaa ggcccctggg tttggctgat ggaggccatg ggtgaggctg | 8520 |
| atgtaaatgg agaggcagga aggaaagccc agctggagtg ggctcaccga ggatagggtg | 8580 |
| gcgagaggag acaaagaagg aacagtgagg gcagacaact ctttgaagat gtttagctat | 8640 |
| aaggctgcag agaaactgag cccacagctg cagggtggtt atggagtgag ggaagctctt | 8700 |
| ttaaggttgg gggtataccc agcatgttaa tgcacctggg ggaatggtcc agtggagcag | 8760 |
| gaagaactga agagagcaga aagaggaaga atcattaggg ggcagaagtc cttgtagccc | 8820 |
| agagtggatg ttatctaata tcgagtggag gaattaattg gctttagagg agaacaagga | 8880 |
| catgtatccc ctctctgggc ctatcacctt gtagacaatg ggataggtca tgggatagga | 8940 |
| acttggcaca acacatgttc tctcttttaa ttctctccat tatcttatga agcaggcaag | 9000 |
| taggcaaaca attgtcccaa cttacaaaa gaaactgaag cttttataaa ttaagtagta | 9060 |
| catcctaagc aatacaatta ataaatggta gagctgagat tcaaactgaa gcagtggcct | 9120 |
| gggggtagca tctggaatcc ttcccacctt tagggctgct gtgctgcggt gctgctgttt | 9180 |
| aatggcacag agggccagat gactgaatct ctctcagcag tccaggcagt catgcagaag | 9240 |
| gcccagtaga gcaccgggca ggtctgagcc agcatcttca agttccaccc tgtgagcaag | 9300 |
| cacttagctg tgacacactt ctcgagagac tggactcccc cccgcgcaac ccacccaaaa | 9360 |
| gcagataggt aatggtatac agtaaccatt tctagaagtg taagtagtat gcacccaaaa | 9420 |
| taggcaaaac ctgctggcct agtgatagag acaactccca gtcaggctag actggaggcc | 9480 |
| ttggttttat aagtgttcag gtgacaagtg ccacagtagg cttgatcaag tagacaggca | 9540 |
| ggcaagacaa atgcttacca atgcaagcta atgaaatgtt tcttttgcag aattcctgtc | 9600 |
| ctgtgaagga agccaaccag agtacgttgg aaaacttctt ggaaaggcta aagacgatca | 9660 |
| tgagagagaa atattcaaag tgttcgagct gaatatttta atttatgagt ttttgatagc | 9720 |
| tttatttttt aagtatttat atatttataa ctcatcataa aataaagtat atatagaatc | 9780 |
| taacagcaat ggcatttaat gtattggcta tgtttacttg acaaatgaaa ttatggtttg | 9840 |
| caacttttag ggaaatcaat ttagtttacc aagagactat aaatgctatg gagccaaaac | 9900 |

<210> SEQ ID NO 31
<211> LENGTH: 1102
<212> TYPE: DNA
<213> ORGANISM: Homo sapiens

<400> SEQUENCE: 31

| | |
|---|---|
| cagagaagct ctatctcccc tccaggagcc cagctatgaa ctccttctcc acaagcgcct | 60 |
| tcggtccagt tgccttctcc ctggggctgc tcctggtgtt gcctgctgcc ttccctgccc | 120 |
| cagtaccccc aggagaagat tccaaagatg tagccgcccc acacagacag ccactcacct | 180 |
| cttcagaacg aattgacaaa caaattcggt acatcctcga cggcatctca gccctgagaa | 240 |
| aggagacatg taacaagagt aacatgtgtg aaagcagcaa agaggcactg gcagaaaaca | 300 |
| acctgaacct tccaaagatg gctgaaaaag atggatgctt ccaatctgga ttcaatgagg | 360 |

```
agacttgcct ggtgaaaatc atcactggtc ttttggagtt tgaggtatac ctagagtacc      420
tccagaacag atttgagagt agtgaggaac aagccagagc tgtgcagatg agtacaaaag      480
tcctgatcca gttcctgcag aaaaaggcaa agaatctaga tgcaataacc acccctgacc      540
caaccacaaa tgccagcctg ctgacgaagc tgcaggcaca gaaccagtgg ctgcaggaca      600
tgacaactca tctcattctg cgcagcttta aggagttcct gcagtccagc tgagggctc       660 ttcggcaaat gtagcatggg cacctcagat tgttgttgtt aatgggcatt ccttcttctg      720
gtcagaaacc tgtccactgg gcacagaact tatgttgttc tctatggaga actaaaagta      780
tgagcgttag gacactattt taattatttt taatttatta atatttaaat atgtgaagct      840
gagttaattt atgtaagtga tatttatatt ttaagaagta ccacttgaaa cattttatgt      900
attagttttg aaataataat ggaaagtggc tatgcagttt gaatatcctt tgtttcagag      960
ccagatcatt tcttggaaag tgtacgctta cctcaaataa atggctaact tatacatatt     1020 tttaagaaa tatttatatt gtatttatat aatgtataaa atggttttta taccaataaa     1080
tggcatttta aaaaattcag ca                                              1102
```

<210> SEQ ID NO 32
<211> LENGTH: 1589
<212> TYPE: DNA
<213> ORGANISM: Homo sapiens

<400> SEQUENCE: 32

```
gaattcctct ggtcctcatc caggtgcgcg ggaagcaggt gcccaggaga gagggataa       60 tgaagattcc atgctgatga tcccaaagat tgaacctgca gaccaagcgc aaagtagaaa     120
ctgaaagtac actgctggcg gatcctacgg aagttatgga aaaggcaaag cgcagagcca     180
cgccgtagtg tgtgccgccc cccttgggat ggatgaaact gcagtcgcgg cgtgggtaag     240
aggaaccagc tgcagagatc accctgccca acacagactc ggcaactccg cggaagacca     300
gggtcctggg agtgactatg gcggtgagag gcttgctcct gctccagttg cggtcatcat     360
gactacgccc gcctcccgca gaccatgttc catgtttctt ttaggtatat ctttggactt     420
cctcccctga tccttgttct gttgccagta gcatcatctg attgtgatat tgaaggtaaa     480
gatggcaaac aatatgagag tgttctaatg gtcagcatcg atcaattatt ggacagcatg     540
aaagaaattg gtagcaattg cctgaataat gaatttaact ttttttaaaag acatatctgt     600 gatgctaata aggaaggtat gttttttattc cgtgctgctc gcaagttgag gcaatttctt     660
aaaatgaata gcactggtga ttttgatctc cacttattaa aagtttcaga aggcacaaca     720
atactgttga actgcactgg ccaggttaaa ggaagaaaac cagctgccct gggtgaagcc     780
caaccaacaa agagtttgga agaaaataaa tctttaaagg aacagaaaaa actgaatgac     840
ttgtgtttcc taaagagact attacaagag ataaaaactt gttggaataa attttgatg     900 ggcactaaag aacactgaaa aatatggagt ggcaatatag aaacacgaac tttagctgca     960
tcctccaaga atctatctgc ttatgcagtt tttcagagtg gaatgcttcc tagaagttac    1020
tgaatgcacc atggtcaaaa cggattaggg catttgagaa atgcatattg tattactaga    1080
agatgaatac aaacaatgga aactgaatgc tccagtcaac aaactatttc ttatatatgt    1140
gaacatttat caatcagtat aattctgtac tgatttttgt aagacaatcc atgtaaggta    1200
tcagttgcaa taatacttct caaacctgtt taaatatttc aagacattaa atctatgaag    1260
tatataatgg tttcaaagat tcaaaattga cattgcttta ctgtcaaaat aattttatgg    1320
ctcactatga atctattata ctgtattaag agtgaaaatt gtcttcttct gtgctggaga    1380
```

| | |
|---|---:|
| tgttttagag ttaacaatga tatatggata atgccggtga gaataagaga gtcataaacc | 1440 |
| ttaagtaagc aacagcataa caaggtccaa gatacctaaa agagatttca agagatttaa | 1500 |
| ttaatcatga atgtgtaaca cagtgccttc aataaatggt atagcaaatg ttttgacatg | 1560 |
| aaaaaaggac aatttcaaaa aaataaaat | 1589 |

<210> SEQ ID NO 33
<211> LENGTH: 8868
<212> TYPE: DNA
<213> ORGANISM: Homo sapiens

<400> SEQUENCE: 33

| | |
|---|---:|
| ccctccaaaa tctatttgca taagcacaca cacacacaca cacacacaca ccccagcagt | 60 |
| tcttgcctgc ccagattcct ctgcagctaa agtgatgaaa cttactgggc ggagcttcct | 120 |
| aaaaagatta ttagggtctc ctgggttggt gtgcctttaa acctttggac tttaccacct | 180 |
| cctatctctc ctatctcctt gcaacaaagg ttaggagaac aagaatgcac aaaaaacggg | 240 |
| tcctggatga catctgagtg cctgctttgg gcttcttgat gagtgagaca gaaaataaaa | 300 |
| tacaaccccc tcttttaaaa gccatgctta ctcaggtttt ccttcatttg cagctaaata | 360 |
| cagaaatgag agaatatttt ggagcaggga tggaagaaga gaggtattcc ccttcccaca | 420 |
| accttctgat ttcccactac atcccccact ggaaaaattc atttaaaatc agtataataa | 480 |
| gcatttgatt agatgcctac tatgcatctg ggcttgaggg caaactggac tcagccttttt | 540 |
| ggcctcaaga agctcacagt gtgagagtgg catttgtgtc ctcttaaatt cacaggacta | 600 |
| aattgtccca ggctacattc tatccatcca taggtgcctg ccttctcact tccctctctt | 660 |
| catggctctt gccttgtagg aaaatccaaa cccaaatgtg gtgacatgtg agtgttggca | 720 |
| ttcatgtctc agacatgacc tatgggcttg ggacttttcc ccgtgtaccc cacgtgactt | 780 |
| ttcacgatga acaggtatct ccaaaaactt cgagaaatag gagtcctgtt tgtgtgttct | 840 |
| tgttgctttg tcaatatata gagagcacag ggtcatctta taattctaaa aatgttcatt | 900 |
| atctatctct tcgacagaaa tactatgaga catacttgat taggagaagc cgttatctcc | 960 |
| atatgctaaa tgaggacttg caccagggaa cttgcccatg gttctctcca accacttaaa | 1020 |
| ttctgaaatt ttgaaatgag agtggacagt aatttcaaat caatgggaaa agaatcaaat | 1080 |
| cttcagcaaa tggcttgaga taattagcta cacatttcag aacaaataaa gaagtcagat | 1140 |
| ccgggccggg cacagtggct catgctgtaa tctcagcact ctgggaggcc aaggcgggcg | 1200 |
| gatcataagg tcaggagatc gagaccatcc tggttaacac agtgaaaccc cgtctctaat | 1260 |
| aaaaatacaa aagaaaataa aaaaacttag ccgggcgtgg tgccagcgcc tgtagtccca | 1320 |
| gctactcggg agcgtgaggc aggagaatgg cttgaactcg ggaggcagag cttgcagtga | 1380 |
| gctgagatca tgccactgca ctccagcctg ggcaacagag cgagactctg tctcaaaaaa | 1440 |
| aaaaaagct agtcagatcc taacctcaac cctatttaac agattataga tgaagaaggt | 1500 |
| acaaatggct tttacatacc tcccttctcc ctgacatttt gtatgtgtgt gtgtgtgtat | 1560 |
| ttacacacac atctcatata aggaaattga agggaggctg cctgcatccc tgagtcactc | 1620 |
| tccctctcct tctgaatgct tacctgtgcc cagaccacct ccttagcctc gcaccctcca | 1680 |
| ggcttacagg gcactcttct atgcccatcc caagtatagc tgataccttc caagggccag | 1740 |
| acttggtgct aagtaccaag tacgcaaaga ttaataaaac aatgtcctgt ttcagggagc | 1800 |
| tcaaagctga ttcggcaggg catggtgtgt acatgaatga taaccacgta gggttgcagg | 1860 |
| tttcctagtg aggtaagcac aaggcaagat gggaaacaaa ggaaggaggg gttcacagcc | 1920 |

```
tcacccagag tccagaaccc ctggcctgcc tggtgcccat gctgagtcca cttctggaac    1980
acccagctca gagaggggt  tagacctgca ggctaacaca gacacagccc agaaaaccca    2040
ggagccgagg gggaaggaga aaggtgcaag aaggggaaac ccaggtcctg gtccccttct    2100
ctctgcttcc tggcagcaga actcagacag aacccttaag ccagtctaag tctggcagga    2160
ccagtaagtt ctgagttagc tccatactag tttctagcag gctctttctc acttcctgat    2220
tcttaggttt ctacattgac actccctgaa gagttgggaa gagacaccac agtccctga     2280 ccctgatcca taggtcacac agcagggaca tccacagggt gacgtgggcc ctctcatccc    2340
tccctcccac tcacttcacg ctggctgggc cccaaggtgt ttgcacccct tgcagtgagt    2400
gaccttctct agtgcagcaa gctcagaacc tgctgccact ggagttgtcc cattgctgat    2460
gcagaaaggt gaagaactag cagaacactg gaaatgccct ccatctgggt ccatggctac    2520
ttaagctcaa tgctccctgg caggcaggag acaggtgct  attgccctgt gggacagat     2580 gaaaaacaga cacaggagg  atgagtgatt tgccctgact atagagtggc agggccaagc    2640
agagcccagg cctcctgcac ctaggtcaat gttcctccca gttacagtct aaactggaat    2700
gcaggcaaag cccctgtgga aggggaaggt gaaggctcaa tcaaaggatc cccagagact    2760
ttccagatat ctgaagaagt cctgatgtca ctgccccggt ccttccccag gtagagcaac    2820
actcctcgct gcaacccaac tggctcccct taccttctac acacacacac acacacacac    2880
acacacacac acacacacc  acacaaatcc aagacaacac tactaaggct ctttgggag     2940 ggggaagtag ggataggtaa gaggaaagta agggacctcc tatccagcct ccatggaatc    3000
ctgacttctt ttccttgtta tttcaacttc ttccacccca tcttttaaac tttagactcc    3060
agccacagaa gcttacaact aaaagaaact ctaaggccaa tttaatccaa ggtttcattc    3120
tatgtgctgg agatggtgta cagtagggtg aggaaaccaa attctcagtt agcactggtg    3180 taccctttgta caggtgatgt aacatctctg tgcctcagtt tgctcactat aaaatagaga    3240
cggtaggggt catggtgagc actacctgac tagcatataa gaagctttca gcaagtgcag    3300
actactctta cccacttccc ccaagcacag ttggggtggg ggacagctga agaggtggaa    3360
acatgtgcct gagaatccta atgaaatcgg ggtaaaggag cctggaacac atcctgtgac    3420
cccgcctgtc ctgtaggaag ccagtctctg gaaagtaaaa tggaagggct gcttgggaac    3480
tttgaggata tttagcccac cccctcattt ttacttgggg aaactaaggc ccagagacct    3540
aaggtgactg cctaagttag caaggagaag tcttgggtat tcatcccagg ttgggggac     3600 ccaattattt ctcaatccca ttgtattctg gaatgggcaa tttgtccacg tcactgtgac    3660
ctaggaacac gcgaatgaga acccacagct gagggcctct gcggacagaa cagctgttct    3720
ccccaggaaa tcaactttt  ttaattgaga agctaaaaaa ttattctaag agaggtagcc    3780
catcctaaaa atagctgtaa tgcagaagtt catgttcaac caatcatttt tgcttacgat    3840
gcaaaaattg aaaactaagt ttattagaga ggttagagaa ggaggagctc taagcagaaa    3900
aaatcctgtg ccgggaaacc ttgattgtgg cttttttaatg aatgaagagg cctccctgag    3960
cttacaatat aaagggggga cagagaggtg aaggtctaca catcagggg  ttgctcttgc    4020 aaaaccaaac cacaagacag acttgcaaaa gaaggcatgc acagctcagc actgctctgt    4080
tgcctggtcc tcctgactgg ggtgagggcc agcccaggcc agggcaccca gtctgagaac    4140
agctgcaccc acttcccagg caacctgcct aacatgcttc gagatctccg agatgccttc    4200
agcagagtga agactttctt tgtgagtatg attccttcct gtcctttctc tcttcctggg    4260
actgcctgaa ctagacattc tcctggaact ataagaaccc tcctcctgcg cctccacctc    4320
```

```
catccccaac acctattccc ccaaacttaa attcttaaga agaaatccta gatcaagcca   4380
tgggttggtc agttaagcta agccagatag atacagtaaa tgtcaggaca cacctgcctt   4440
ataaagtaaa tgcgttcttt ctcgtgctga gaaacttata acgcactcct gctgcgcgcc   4500
tatatcattt attggctagg agaagtaaag aaaggtctga tgtcgaggtg aagatgctcc   4560
ccagtccttg cagcaaggga aatttaaatt gcctctgctt agagcgtttc cagcctgaaa   4620
gaccagtggt ttagggaagc actctaccat gagggaaacc tgcattagaa ggagcttctt   4680
aaatccctgg gatctttcca agctaaactg agtgtctaca gtgggagaa agaaaagcag    4740
agaacaggac atgaggggct caaggccccg aagggttgac ataggtgtcc cttaaagcct   4800
aatgtacgtc cgcagaaaga agaccaggac tgagtcaagc ttctgctttc ccttgaaaat   4860
caggccagat ttttaaaata acttgactct agaggaggag gactgattta agtgatcgtg   4920
tcccatactg ttgaatcctc tgttttaaa ctccccttt gtattatatt tggccagagc     4980
caatttgtat taaaaaaaaa aaaatctcta atgaaaggg catcaaaaat accgcatttc    5040
agttatttcc ccaaacctaa agttcattct ccttttcctt cctgcagcaa atgaaggatc   5100
agctggacaa cttgttgtta aaggagtcct tgctggagga ctttaaggtg agagcagggg   5160
cgggggtgct gggggagtgt gcagcatgat taagggaagg gaggctctgc ttcctgattg   5220
tgcagggaat tgggttttgtt tccttggctt gaaaggagaa gtgggaagat gttaactcag   5280
cacatcagca gcagagggtt tacaaagggc tcagtcttcg ggggaggctt ctggtaagga   5340
ggatcgcatg aacaagctgt cctcttaagc tagttgcagc agccctcctc ccagccacct   5400
ccgccaatct ctcactcacc ttcggctcct gccccagggt tacctgggtt gccaagcctt   5460
gtctgagatg atccagtttt acctggagga ggtgatgccc caagctgaga accaagaccc   5520
agacatcaag gcgcatgtga actccctggg ggagaacctg aagaccctca ggctgaggct   5580
acggcgctgt gtaagtagca gatcagttct ttcccttgca gctgccccca aaataccatc   5640
tcctacagac cagcagggac actcacatcc acagacacag caaagagaca cagctgcaag   5700
cgatcgtgta aatgaggaaa gactcctgag tcatagtctc ttctcatttc tctttgagca   5760
ggcgttgggg gtggctgcta ggcatttaca tgtgaaattt gcaaacagct tcctgttatt   5820
tgtgagtcat ttgtgggtta ttaactactc ccctctctct tcataaaagg agcccagagc   5880
ttcagtcagg cctccactgc ctctttgtac tagacctggg cggggagcta aggttcccaa   5940
agcagaggga aacatcattc acctctttta atctcaatgt ttgaaagcaa agctctaaga   6000
agggcccaat tgactgacag gatttcccct ggcattttag aagggacaag ggggctattc   6060
atccccaggc tagtgtctat gagtaattcc tccaggaatt tatttctcca actgaaatga   6120
tgccgtcact actaatggtt tcccctgttc tgtcaccaat attggaaaat cagttggtgt   6180
ctatttgtag gacaaggcta tgtgaagggt ttggtcccag tagcttccct cctcagatgc   6240
ttagttagtg ttcctccggt ggctgtgact gacggggggg agaacaggag agagaggcag   6300
aaaaggacag gctgaagaat gcctcgctca gcactgcagg agatactgta gagttctggg   6360
ggaggaagga atcccaagac cctgggttgt catccaagcc ttgcaaacat cttggagtga   6420
gtcctggaga aatacattta actcccaggg ccatggaagc agggctcagt tctctctccc   6480
agctgtgagg cgaggatttg gataaatctg gcctcctcat gatgcaccag cttgtcccta   6540
agcgtgatgg acatggagct ggaagccagg atcaccaaca cttttctcttt tcttccacag   6600
catcgatttc ttccctgtga aaacaagagc aaggccgtgg agcaggtgaa gaatgccttt   6660
aataaggtag agagggtctc agagcacaac ccatgcccac tccccaaccc caaagcatgg   6720
```

```
aaggtggtgg gactcaatag gccccattct tcattgagag agtgtgggaa cctacaatgg    6780
tatgacctct cagccattag gagctgctgc cttgattgta tttgttttct gttaagttgt    6840
ctttgggggt tctaaatgac tgctcgcttg cctttgcagg cttgcgggtc agggctggcc    6900
gcccaggtga acacagatga gctgcatgct ggggagagtg acaaaggaaa cagaaagtac    6960
agaaagtagc ttgttgggaa tctagtctga acccacacgt gcaggaagct ggcacattaa    7020
atgtgcacat tacaaataca cctggggtg cagcccagat ctcccctagg acctcagaat    7080
gagcaggaag ctggattgct cacttaacct ggagttggtt caagcccgct ttccatctgc    7140
ccttcgcacc tgcggaggtg cctgagaatg tcagtttccc aaacgaaatg gggtttcaca    7200
cttccaactg tgcgtgaact ttttcagtct gatttcccag aaaccgtgcg gcctatgtcc    7260
tcctcgtggg ctggggacag acactgcaca gagtgccaac atcaggggt gtgaatttct    7320 catagtaggt cagggcggca gggagggcct gctcagtgtg ttggtgggag aacacagaca    7380
tttaaaaggc tccctcctct cctctcaccg tcttgctttc gaagcgcttc ctctaatgtc    7440
ttttcatcaa actctgcata atcatcatgt gaatacgtga cctttaaaat tgttgaaaag    7500
gcatcatttt gaagacagtg ctttgcaaaa tgaatgctac cccaattgct aggggaggc    7560 ctggaggaga tgaaaggtca atgcacagcc tttcccaagg cagctaggcc tatcctctgg    7620
tttacttccc agcgtgaggg agaacaagca acctctgcac tcaaggtcat gcccatccat    7680
gagcatgagg gaggggagcc tatttagtcc ccagaaagga ttttaactgt atgtttctta    7740
gctccaagag aaaggcatct acaaagccat gagtgagttt gacatcttca tcaactacat    7800
agaagcctac atgacaatga agatacgaaa ctgagacatc agggtggcga ctctatagac    7860
tctaggacat aaattagagg tctccaaaat cggatctggg gctctgggat agctgaccca    7920
gccccttgag aaaccttatt gtacctctct tatagaatat ttattacctc tgatacctca    7980
accccatttt ctatttattt actgagcttc tctgtgaacg atttagaaag aagcccaata    8040
ttataatttt tttcaatatt tattatttc acctgttttt aagctgtttc catagggtga    8100
cacactatgg tatttgagtg ttttaagata aattataagt tacataaggg aggaaaaaaa    8160
atgttctttg gggagccaac agaagcttcc attccaagcc tgaccacgct ttctagctgt    8220
tgagctgttt tccctgacct ccctctaatt tatcttgtct ctgggcttgg ggcttcctaa    8280
ctgctacaaa tactcttagg aagagaaacc agggagcccc tttgatgatt aattcacctt    8340
ccagtgtctc ggagggattc ccctaacctc attcccaac cacttcattc ttgaaagctg    8400
tggccagctt gttatttata acaacctaaa tttggttcta ggccgggcgc ggtggctcac    8460
gcctgtaatc ccagcacttt gggaggctga ggcgggtgga tcacttgagg tcaggagttc    8520
ctaaccagcc tggtcaacat ggtgaaaccc cgtctctact aaaaatacaa aaattagccg    8580
ggcatggtgg cgcgcacctg taatcccagc tacttgggag gctgaggcaa gagaattgct    8640
tgaacccagg agatggaagt tgcagtgagc tgatatcatg cccctgtact ccagcctggg    8700
tgacagagca agactctgtc tcaaaaaaat aaaaataaaa ataaatttgg ttctaataga    8760
actcagtttt aactagaatt tattcaattc ctctgggaat gttacattgt ttgtctgtct    8820
tcatagcaga ttttaatttt gaataaataa atgtatctta ttcacatc                 8868
```

<210> SEQ ID NO 34
<211> LENGTH: 1444
<212> TYPE: DNA
<213> ORGANISM: Homo sapiens

<400> SEQUENCE: 34

-continued

| | |
|---|---|
| tttcattttg ggccgagctg gaggcggcgg ggccgtcccg gaacggctgc ggccgggcac | 60 |
| cccgggagtt aatccgaaag cgccgcaagc cccgcgggcc ggccgcaccg cacgtgtcac | 120 |
| cgagaagctg atgtagagag agacacagaa ggagacagaa agcaagagac cagagtcccg | 180 |
| ggaaagtcct gccgcgcctc gggacaatta taaaaatgtg gcccctggg tcagcctccc | 240 |
| agccaccgcc ctcacctgcc gcggccacag gtctgcatcc agcggctcgc cctgtgtccc | 300 |
| tgcagtgccg gctcagcatg tgtccagcgc gcagcctcct ccttgtggct accctggtcc | 360 |
| tcctggacca cctcagtttg gccagaaacc tccccgtggc cactccagac ccaggaatgt | 420 |
| tcccatgcct tcaccactcc caaaacctgc tgagggccgt cagcaacatg ctccagaagg | 480 |
| ccagacaaac tctagaattt taccccttgca cttctgaaga gattgatcat gaagatatca | 540 |
| caaaagataa aaccagcaca gtggaggcct gtttaccatt ggaattaacc aagaatgaga | 600 |
| gttgcctaaa ttccagagag acctctttca taactaatgg gagttgcctg gcctccagaa | 660 |
| agacctcttt tatgatggcc ctgtgcctta gtagtattta tgaagacttg aagatgtacc | 720 |
| aggtggagtt caagaccatg aatgcaaagc ttctgatgga tcctaagagg cagatctttc | 780 |
| tagatcaaaa catgctggca gttattgatg agctgatgca ggccctgaat ttcaacagtg | 840 |
| agactgtgcc acaaaaatcc tcccttgaag aaccggattt ttataaaact aaaatcaagc | 900 |
| tctgcatact tcttcatgct ttcagaattc gggcagtgac tattgataga gtgatgagct | 960 |
| atctgaatgc ttcctaaaaa gcgaggtccc tccaaaccgt tgtcattttt ataaaacttt | 1020 |
| gaaatgagga aactttgata ggatgtggat taagaactag ggaggggggaa agaaggatgg | 1080 |
| gactattaca tccacatgat acctctgatc aagtattttt gacatttact gtggataaat | 1140 |
| tgttttaag ttttcatgaa tgaattgcta agaagggaaa atatccatcc tgaaggtgtt | 1200 |
| tttcattcac tttaatagaa gggcaaatat ttataagcta tttctgtacc aaagtgtttg | 1260 |
| tggaaacaaa catgtaagca taacttattt taaaatattt atttatataa cttggtaatc | 1320 |
| atgaaagcat ctgagctaac ttatatttat ttatgttata tttattaaat tatttatcaa | 1380 |
| gtgtatttga aaatatttt taagtgttct aaaaataaaa gtattgaatt aaagtgaaaa | 1440 |
| aaaa | 1444 |

<210> SEQ ID NO 35
<211> LENGTH: 2347
<212> TYPE: DNA
<213> ORGANISM: Homo sapiens

<400> SEQUENCE: 35

| | |
|---|---|
| ctgtttcagg gccattggac tctccgtcct gcccagagca agatgtgtca ccagcagttg | 60 |
| gtcatctctt ggttttccct ggttttttctg gcatctcccc tcgtggccat atgggaactg | 120 |
| aagaaagatg tttatgtcgt agaattggat tggtatccgg atgcccctgg agaaatggtg | 180 |
| gtcctcacct gtgacacccc tgaagaagat ggtatcacct ggaccttgga ccagagcagt | 240 |
| gaggtcttag gctctggcaa aaccctgacc atccaagtca agagtttgg agatgctggc | 300 |
| cagtacacct gtcacaaagg aggcgaggtt ctaagccatt cgctcctgct gcttcacaaa | 360 |
| aaggaagatg gaatttggtc cactgatatt ttaaaggacc agaaagaacc caaaaataag | 420 |
| acctttctaa gatgcgaggc caagaattat tctggacgtt tcacctgctg gtggctgacg | 480 |
| acaatcagta ctgatttgac attcagtgtc aaaagcagca gaggctcttc tgaccccaa | 540 |
| gggggtgacgt gcgagctgc tacactctct gcagagagag tcagagggga caacaaggag | 600 |
| tatgagtact cagtggagtg ccaggaggac agtgcctgcc cagctgctga ggagagtctg | 660 |

```
cccattgagg tcatggtgga tgccgttcac aagctcaagt atgaaaacta caccagcagc    720
ttcttcatca gggacatcat caaacctgac ccacccaaga acttgcagct gaagccatta    780
aagaattctc ggcaggtgga ggtcagctgg gagtaccctg acacctggag tactccacat    840
tcctacttct ccctgacatt ctgcgttcag gtccagggca agagcaagag agaaaagaaa    900
gatagagtct tcacggacaa gacctcagcc acggtcatct gccgcaaaaa tgccagcatt    960
agcgtgcggg cccaggaccg ctactatagc tcatcttgga gcgaatgggc atctgtgccc   1020
tgcagttagg ttctgatcca ggatgaaaat tggaggaaaa gtggaagat attaagcaaa    1080 atgtttaaag acacaacgga atagacccaa aaagataatt tctatctgat ttgctttaaa   1140 acgtttttt aggatcacaa tgatatcttt gctgtatttg tatagttaga tgctaaatgc    1200
tcattgaaac aatcagctaa tttatgtata gattttccag ctctcaagtt gccatgggcc    1260
ttcatgctat ttaaatattt aagtaattta tgtatttatt agtatattac tgttatttaa    1320
cgtttgtctg ccaggatgta tggaatgttt catactctta tgacctgatc catcaggatc    1380
agtccctatt atgcaaaatg tgaatttaat tttatttgta ctgacaactt ttcaagcaag    1440
gctgcaagta catcagtttt atgacaatca ggaagaatgc agtgttctga taccagtgcc    1500
atcatacact tgtgatggat gggaacgcaa gagatactta catggaaacc tgacaatgca    1560
aacctgttga agatccag gagaacaaga tgctagttcc catgtctgtg aagcttcct    1620 ggagatggtg ttgataaagc aatttagggc cacttacact tctaagcaag tttaatcttt    1680
ggatgcctga attttaaaag ggctagaaaa aaatgattga ccagcctggg aaacataaca    1740
agaccccgtc tctacaaaaa aaatttaaaa ttagccaggc gtggtggctc atgcttgtgg    1800
tcccagctgt tcaggaggat gaggcaggag gatctcttga gcccaggagg tcaaggctat    1860
ggtgagccgt gattgtgcca ctgcatacca gcctaggtga cagaatgaga ccctgtctca    1920 aaaaaaaaa tgattgaaat taaaattcag ctttagcttc catggcagtc ctcaccccca    1980
cctctctaaa agacacagga ggatgacaca gaaacaccgt aagtgtctgg aaggcaaaaa    2040
gatcttaaga ttcaagagag aggacaagta gttatggcta aggacatgaa attgtcagaa    2100
tggcaggtgg cttcttaaca gccctgtgag aagcagacag atgcaaagaa atctggaat    2160 cccttcta ttagcatgaa tgaacctgat acacaattat gaccagaaaa tatggctcca    2220
tgaaggtgct acttttaagt aatgtatgtg cgctctgtaa agtgattaca tttgtttcct    2280
gtttgtttat ttatttattt attttttgcat tctgaggctg aactaataaa aactcttctt    2340
tgtaatc                                                              2347
```

<210> SEQ ID NO 36
<211> LENGTH: 1202
<212> TYPE: DNA
<213> ORGANISM: Homo sapiens

<400> SEQUENCE: 36

```
tgtccggcgc cccccgggag ggaactgggt ggccgcaccc tcccggctgc ggtggctgtc     60
gccccccacc ctgcagccag gactcgatgg agaatccatt ccaatatatg gccatgtggc    120
tctttggagc aatgttccat catgttccat gctgctgctg acgtcacatg gagcacagaa    180
atcaatgtta gcagatagcc agcccataca agatcgtatt gtattgtagg aggcatcgtg    240
gatggatggc tgctggaaac cccttgccat agccagctct tcttcaatac ttaaggattt    300
accgtggctt tgagtaatga gaatttcgaa accacatttg agaagtattt ccatccagtg    360
ctacttgtgt ttacttctaa acagtcattt tctaactgaa gctggcattc atgtcttcat    420
```

```
tttgggctgt tcagtgcag ggcttcctaa aacagaagcc aactgggtga atgtaataag    480
tgatttgaaa aaaattgaag atcttattca atctatgcat attgatgcta ctttatatac    540
ggaaagtgat gttcacccca gttgcaaagt aacagcaatg aagtgctttc tcttggagtt    600
acaagttatt tcacttgagt ccggagatgc aagtattcat gatacagtag aaaatctgat    660
catcctagca acaacagtt tgtcttctaa tgggaatgta acagaatctg gatgcaaaga    720
atgtgaggaa ctggaggaaa aaatattaa agaattttg cagagttttg tacatattgt    780
ccaaatgttc atcaacactt cttgattgca attgattctt tttaaagtgt ttctgttatt    840
aacaaacatc actctgctgc ttagacataa caaaacactc ggcatttaaa atgtgctgtc    900
aaaacaagtt tttctgtcaa gaagatgatc agaccttgga tcagatgaac tcttagaaat    960
gaaggcagaa aaatgtcatt gagtaatata gtgactatga acttctctca gacttacttt   1020
actcattttt ttaatttatt attgaaattg tacatatttg tggaataatg taaaatgttg   1080
aataaaaata tgtacaagtg ttgtttttta agttgcactg atattttacc tcttattgca   1140
aaatagcatt tgtttaaggg tgatagtcaa attatgtatt ggtggggctg ggtaccaatg   1200
ct                                                                 1202

<210> SEQ ID NO 37
<211> LENGTH: 306
<212> TYPE: DNA
<213> ORGANISM: Homo sapiens

<400> SEQUENCE: 37
atcgtcaacc tcaaggacga gctgctgttt cccagctggg aggctctgtt ctcaggctct     60
gagggtccgc tgaagcccgg ggcacgcatc ttctcctttg acggcaagga cgtcctgagg    120
caccccaccc ggccccagaa gagcgtgtgg catggctcgg accccaacgg gcgcaggctg    180
accgagagct actgtgagac gtggcggacg gaggctccct cggccacggg ccaggcctcc    240
tcgctgctgg ggggcaggct cctggggcag agtgccgcga gcagccatca cgcctacatc    300
gtgcta                                                             306

<210> SEQ ID NO 38
<211> LENGTH: 1062
<212> TYPE: DNA
<213> ORGANISM: Homo sapiens

<400> SEQUENCE: 38
tcagagtgca agactgggaa tggaaagaac tacagaggga cgatgtccaa aacaaaaaat     60
ggcatcacct gtcaaaaatg gagttccact tctccccaca gacctagatt ctcacctgct    120
acacacccct cagagggact ggaggagaac tactgcagga atccagacaa cgatccgcag    180
gggccctggt gctatactac tgatccagaa aagagatatg actactgcga cattcttgag    240
tgtgaagagg aatgtatgca ttgcagtgga gaaaactatg acggcaaaat tccaagacc    300
atgtctggac tggaatgcca ggcctggac tctcagagcc acacgctca tggatacatt    360
ccttccaaat ttccaaacaa gaacctgaag aagaattact gtcgtaaccc cgataggag    420
ctgcggcctt ggtgtttcac caccgacccc aacagcgct gggaactttg cgacatcccc    480
cgctgcacaa cacctccacc atcttctggt cccacctacc agtgtctgaa gggaacaggt    540
gaaaactatc gcgggaatgt ggctgttacc gttccgggc acacctgtca gcactggagt    600
gcacagaccc tcacacaca taacaggaca ccagaaaact tccctgcaa aaatttggat    660
gaaaactact gccgcaatcc tgacggaaaa agggcccat ggtgccatac aaccaacagc    720
```

| | |
|---|---|
| caagtgcggt gggagtactg taagataccg tcctgtgact cctccccagt atccacggaa | 780 |
| caattggctc ccacagcacc acctgagcta acccctgtgg tccaggactg ctaccatggt | 840 |
| gatggacaga gctaccgagg cacatcctcc accaccacca caggaaagaa gtgtcagtct | 900 |
| tggtcatcta tgacaccaca ccggcaccag aagacccag aaaactaccc aaatgctggc | 960 |
| ctgacaatga actactgcag gaatccagat gccgataaag gcccctggtg ttttaccaca | 1020 |
| gaccccagcg tcaggtggga gtactgcaac ctgaaaaaat gc | 1062 |

<210> SEQ ID NO 39
<211> LENGTH: 738
<212> TYPE: DNA
<213> ORGANISM: Homo sapiens

<400> SEQUENCE: 39

| | |
|---|---|
| ccaggtttga aaggaaaacg tggagacagt ggatcacctg caacctggac aacgagaggc | 60 |
| tttgtcttca cccgacacag tcaaaccaca gcaattcctt catgtccaga ggggacagtg | 120 |
| ccactctaca gtgggttttc ttttcttttt gtacaaggaa atcaacgagc ccacggacaa | 180 |
| gaccttggaa ctcttggcag ctgcctgcag cgatttacca caatgccatt cttattctgc | 240 |
| aatgtcaatg atgtatgtaa ttttgcatct cgaaatgatt attcatactg gctgtcaaca | 300 |
| ccagctctga tgccaatgaa catggctccc attactggca gagcccttga gccttatata | 360 |
| agcagatgca ctgtttgtga aggtcctgcg atcgccatag ccgttcacag ccaaaccact | 420 |
| gacattcctc catgtcctca cggctggatt tctctctgga aaggattttc attcatcatg | 480 |
| ttcacaagtg caggttctga gggcaccggg caagcactgg cctcccctgg ctcctgcctg | 540 |
| gaagaattcc gagccagccc atttctagaa tgtcatggaa gaggaacgtg caactactat | 600 |
| tcaaattcct acagtttctg gctggcttca ttaaacccag aaagaatgtt cagaaagcct | 660 |
| attccatcaa ctgtgaaagc tggggaatta gaaaaaataa taagtcgctg tcaggtgtgc | 720 |
| atgaagaaaa gacactga | 738 |

<210> SEQ ID NO 40
<211> LENGTH: 2780
<212> TYPE: DNA
<213> ORGANISM: Homo sapiens

<400> SEQUENCE: 40

| | |
|---|---|
| cccgggagcc cagtgcagca gcttccccga tgggtcctgg tcatgcggct tctgccctgt | 60 |
| gggcttcttg ggcaatggca cccactgtga ggacctggac gagtgtgccc tggtccccga | 120 |
| catctgcttc tccaccagca aggtgcctcg ctgtgtcaac actcagcctg gcttccactg | 180 |
| cctgccctgc ccgccccgat acagagggaa ccagcccgtc ggggtcggcc tggaagcagc | 240 |
| caagacggaa aagcaagtgt gtgagcccga aacccatgc aaggacaaga cacacaactg | 300 |
| ccacaagcac gcggagtgca tctacctggg tcacttcagc gaccccatgt acaagtgcga | 360 |
| gtgccagaca ggctacgcgg gcgacgggct catctgcggg gaggactcgg acctggacgg | 420 |
| ctggcccaac ctcaatctgg tctgcgccac caacgccacc taccactgca tcaaggataa | 480 |
| ctgcccccat ctgccaaatt ctgggcagga agactttgac aaggacggga ttggcgatgc | 540 |
| ctgtgatgat gacgatgaca atgacggtgt gaccgatgag aaggacaact gccagctcct | 600 |
| cttcaatccc cgccaggctg actatgacaa ggatgaggtt ggggaccgct gtgacaactg | 660 |
| cccttacgtg cacaaccctg cccagatcga cacagacaac aatggagagg gtgacgcctg | 720 |
| ctccgtggac attgatgggg acgatgtctt caatgaacga gacaattgtc cctacgtcta | 780 |

| | | | |
|---|---|---|---|
| caacactgac cagagggaca cggatggtga cggtgtgggg gatcactgtg acaactgccc | 840 |
| cctggtgcac aaccctgacc agaccgacgt ggacaatgac cttgttgggg accagtgtga | 900 |
| caacaacgag gacatagatg acgacggcca ccagaacaac caggacaact gcccctacat | 960 |
| ctccaacgcc aaccaggctg accatgacag agacggccag ggcgacgcct gtgaccctga | 1020 |
| tgatgacaac gatggcgtcc ccgatgcagg ggacaactgc cggcttgtgt tcaacccaga | 1080 |
| ccaggaggac ttggacggtg atggacgggg tgatatttgt aaagatgatt ttgacaatga | 1140 |
| caacatccca gatattgatg atgtgtgtcc tgaaaacaat gccatcagtg agacagactt | 1200 |
| caggaacttc cagatggtcc ccttggatcc caaagggacc acccaaattg atcccaactg | 1260 |
| ggtcattcgc catcaaggca aggagctggt tcagacagcc aactcggacc ccggcatcgc | 1320 |
| tgtaggtttt gacgagtttg ggtctgtgga cttcagtggc acattctacg taaacactga | 1380 |
| ccgggacgac gactatgctg gcttcgtctt tggttaccag tcaagcagcc gcttctatgt | 1440 |
| ggtgatgtgg aagcaggtga cgcagaccta ctgggaggac cagcccacgc gggcctatgg | 1500 |
| ctactccggc gtgtccctca aggtggtgaa ctccaccacg gggacgggcg agcacctgag | 1560 |
| gaacgcgctg tggcacacgg ggaacacgcc ggggcaggtg cgaaccttat ggcacgaccc | 1620 |
| caggaacatt ggctggaagg actacacggc ctataggtgg cacctgactc acaggcccaa | 1680 |
| gaccggctac atcagagtct tagtgcatga aggaaaacag gtcatggcag actcaggacc | 1740 |
| tatctatgac caaacctacg ctggcgggcg gctgggtcta tttgtcttct ctcaagaaat | 1800 |
| ggtctatttc tcagacctca gtacgaatgc cagagatatt taaacaagat ttgctgcatt | 1860 |
| tccggcaatg ccctgtgcat gccatggtcc ctagacacct cagttcattg tggtccttgc | 1920 |
| ggcttctctc tctagcagca cctcctgtcc cttgacctta actctgatgg ttcttcacct | 1980 |
| cctgccagca accccaaacc caagtgcctt cagaggataa atatcaatgg aactcagaga | 2040 |
| tgaacatcta acccactaga ggaaaccagt ttggtgatat atgagacttt atgtggagtg | 2100 |
| aaaattgggc atgccattac attgcttttt cttgtttgtt taaaaagaat gacgtttaca | 2160 |
| tataaaatgt aattacttat tgtatttatg tgtatatgga gttgaaggga atactgtgca | 2220 |
| taagccatta tgataaatta agcatgaaaa atattgctga actacttttg gtgcttaaag | 2280 |
| ttgtcactat tcttgaatta gagttgctct acaatgacac acaaatcccg ctaaataaat | 2340 |
| tataaacaag ggtcaattca aatttgaagt aatgttttag taaggagaga ttagaagaca | 2400 |
| acaggcatag caaatgacat aagctaccga ttaactaatc ggaacatgta aaacagttac | 2460 |
| aaaaataaac gaactctcct cttgtcctac aatgaaagcc ctcatgtgca gtagagatgc | 2520 |
| agtttcatca agaacaaac atccttgcaa atgggtgtga cgcggttcca gatgtggatt | 2580 |
| tggcaaaacc tcatttaagt aaaaggttag cagagcaaag tgcggtgctt tagctgctgc | 2640 |
| ttgtgccgtt gtggcgtcgg ggaggctcct gcctgagctt ccttccccag ctttgctgcc | 2700 |
| tgagaggaac cagagcagac gcacaggccg gaaaaggcgc atctaacgcg tatctaggct | 2760 |
| ttggtaactg cggacaagcc | 2780 |

<210> SEQ ID NO 41
<211> LENGTH: 966
<212> TYPE: DNA
<213> ORGANISM: Aequorea victoria

<400> SEQUENCE: 41

| | |
|---|---|
| tacacacgaa taaagataaa caaagatgag taaaggagaa gaacttttca ctggagttgt | 60 |
| cccaattctt gttgaattag atggtgatgt taatgggcac aaattttctg tcagtggaga | 120 |

```
gggtgaaggt gatgcaacat acggaaaact taccettaaa tttatttgca ctactggaaa      180
actacctgtt ccatggccaa cacttgtcac tactttctct tatggtgttc aatgcttttc      240
aagataccca gatcatatga aacagcatga cttttttcaag agtgccatgc ccgaaggtta     300
tgtacaggaa agaactatat ttttcaaaga tgacgggaac tacaagacac gtgctgaagt     360
caagtttgaa ggtgataccc ttgttaatag aatcgagtta aaaggtattg attttaaaga     420
agatggaaac attcttggac acaaattgga atacaactat aactcacaca atgtatacat     480
catggcagac aaacaaaaga tggaatcaa agttaacttc aaaattagac acaacattga     540
agatggaagc gttcaactag cagaccatta tcaacaaaat actccaattg gcgatggccc     600
tgtccttta ccagacaacc attacctgtc cacacaatct gccctttcga agatcccaa      660
cgaaaagaga gaccacatgg tccttcttga gtttgtaaca gctgctggga ttacacatgg     720
catggatgaa ctatacaaat aaatgtccag acttccaatt gacactaaag tgtccgaaca     780
attactaaaa tctcagggtt cctggttaaa ttcaggctga gatattattt atatatttat     840
agattcatta aaattgtatg aataatttat tgatgttatt gatagaggtt attttcttat     900
taaacaggct acttggagtg tattcttaat tctatattaa ttacaatttg atttgacttg     960
ctcaaa                                                                 966

<210> SEQ ID NO 42
<211> LENGTH: 2387
<212> TYPE: DNA
<213> ORGANISM: Photinus pyralis

<400> SEQUENCE: 42
ctgcagaaat aactaggtac taagcccgtt tgtgaaaagt ggccaaaccc ataaatttgg       60
caattacaat aaagaagcta aaattgtggt caaactcaca acattttta ttatatacat      120
tttagtagct gatgcttata aaagcaatat ttaaatcgta aacaacaaat aaaataaaat     180
ttaaacgatg tgattaagag ccaaaggtcc tctagaaaaa ggtatttaag caacggaatt     240
cctttgtgtt acattcttga atgtcgctcg cagtgacatt agcattccgg tactgttggt     300
aaaatggaag acgccaaaaa cataaagaaa ggcccggcgc cattctatcc tctagaggat     360
ggaaccgctg gagagcaact gcataaggct atgaagagat acgccctggt tcctggaaca     420
attgctttg tgagtatttc tgtctgattt ctttcgagtt aacgaaatgt tcttatgttt     480
ctttagacag atgcacatat cgaggtgaac atcacgtacg cggaatactt cgaaatgtcc     540
gttcggttgg cagaagctat gaaacgatat gggctgaata caaatcacag aatcgtcgta     600
tgcagtgaaa actctcttca attctttatg ccggtgttgg gcgcgttatt tatcggagtt     660
gcagttgcgc ccgcgaacga catttataat gaacgtaagc accctcgcca tcagaccaaa     720
gggaatgacg tatttaattt ttaaggtgaa ttgctcaaca gtatgaacat ttcgcagcct     780
accgtagtgt ttgtttccaa aaggggttg caaaaaattt tgaacgtgca aaaaaaatta     840
ccaataatcc agaaaattat tatcatggat tctaaaacgg attaccaggg atttcagtcg     900
atgtacacgt tcgtcacatc tcatctacct cccggtttta tgaatacga ttttgtacca     960
gagtccttg atcgtgacaa acaattgca ctgataatga attcctctgg atctactggg     1020
ttacctaagg gtgtggccct tccgcataga actgcctgcg tcagattctc gcatgccagg     1080
tatgtcgtat aacaagagat taagtaatgt tgctacacac attgtagaga tcctatttt      1140
ggcaatcaaa tcattccgga tactgcgatt ttaagtgttg ttccattcca tcacggtttt     1200
ggaatgttta ctacactcgg atatttgata tgtggatttc gagtcgtctt aatgtataga      1260
```

```
                                                                -continued
tttgaagaag agctgttttt acgatccctt caggattaca aaattcaaag tgcgttgcta    1320
gtaccaaccc tattttcatt cttcgccaaa agcactctga ttgacaaata cgatttatct    1380
aatttacacg aaattgcttc tgggggcgca cctctttcga aagaagtcgg ggaagcggtt    1440
gcaaaacggt gagttaagcg cattgctagt atttcaaggc tctaaaacgg cgcgtagctt    1500
ccatcttcca gggatacgac aaggatatgg gctcactgag actacatcag ctattctgat    1560
tacacccgag ggggatgata aaccgggcgc ggtcggtaaa gttgttccat tttttgaagc    1620
gaaggttgtg gatctggata ccgggaaaac gctgggcgtt aatcagagag gcgaattatg    1680
tgtcagagga cctatgatta tgtccggtta tgtaaacaat ccggaagcga ccaacgcctt    1740
gattgacaag gatggatggc tacattctgg agacatagct tactgggacg aagacgaaca    1800
cttcttcata gttgaccgct tgaagtcttt aattaaatac aaaggatatc aggtaatgaa    1860
gatttttaca tgcacacacg ctacaatacc tgtaggtggc ccccgctgaa ttggaatcga    1920
tattgttaca acacccaac atcttcgacg cgggcgtggc aggtcttccc gacgatgacg    1980
ccggtgaact tcccgccgcc gttgttgttt tggagcacgg aaagacgatg acggaaaaag    2040
agatcgtgga ttacgtcgcc agtaaatgaa ttcgttttac gttactcgta ctacaattct    2100
tttcataggt caagtaacaa ccgcgaaaaa gttgcgcgga ggagttgtgt tgtggacga    2160 agtaccgaaa ggtcttaccg gaaaactcga cgcaagaaaa atcagagaga tcctcataaa    2220
ggccaagaag ggcggaaagt ccaaattgta aaatgtaact gtattcagcg atgacgaaat    2280
tcttagctat tgtaatatta tatgcaaatt gatgaatggt aattttgtaa ttgtgggtca    2340
ctgtactatt ttaacgaata ataaaatcag gtataggtaa ctaaaaa               2387
```